United States Patent
Madsen et al.

(10) Patent No.: US 6,177,443 B1
(45) Date of Patent: Jan. 23, 2001

(54) 4,5,6,7-TETRAHYDRO-THIENO[3, 2-C] PYRIDINE DERIVATIVES, THEIR PREPARATION AND USE

(75) Inventors: Peter Madsen, Bagsvaerd; Jane Marie Lundbeck, Glostrup; Niels Westergarrd, Vaerlose; Lars Naerum, Hellerup; Annemarie Reinhardt Varming, Charlottenlund; Helle Demuth, Horsholm; Morten Heide, Holte, all of (DK)

(73) Assignee: Novo Nordisk A/S, Bagsvared (DK)

( * ) Notice: Under 35 U.S.C. 154(b), the term of this patent shall be extended for 0 days.

(21) Appl. No.: 09/035,464

(22) Filed: Mar. 5, 1998

Related U.S. Application Data

(60) Provisional application No. 60/041,641, filed on Mar. 27, 1997, and provisional application No. 60/067,809, filed on Dec. 8, 1997.

(30) Foreign Application Priority Data

Mar. 7, 1997 (DK) .................................................. 0249/97
Nov. 27, 1997 (DK) .................................................. 1365/97

(51) Int. Cl.[7] ........................ A61K 31/44; A61K 31/47; C07D 217/02; C07D 217/06
(52) U.S. Cl. ........................ 514/301; 514/307; 546/114; 546/144; 546/146; 546/150
(58) Field of Search .................................... 514/301, 307; 546/114, 144, 146, 150

(56) References Cited

U.S. PATENT DOCUMENTS 4,681,888  7/1987  Esanu .................................... 514/301

FOREIGN PATENT DOCUMENTS

| | | |
|---|---|---|
| 0 088 250 | 9/1983 | (EP) . |
| 0 157 324 | 10/1985 | (EP) . |
| WO 87/05295 | 9/1987 | (WO) . |
| WO 96/34870 | 11/1996 | (WO) . |

OTHER PUBLICATIONS

Chemical Abstracts 77:5364, Saito et al, 1972.*
Chemical Abstracts 77:96746, Paul et al, 1972.*

* cited by examiner

Primary Examiner—D. Margaret Seaman
(74) Attorney, Agent, or Firm—Steven T. Nelson; Valetta Gregg, Esq.

(57) ABSTRACT

The present invention relates to pharmaceutical compositions comprising a pharmaceutically acceptable carrier or diluent and a compound of formula I

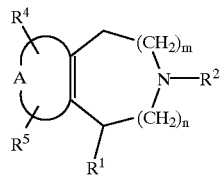

wherein A together with the double bond of formula I is benzene or thiophene; $R^1$ is optionally substituted $C_{1-6}$ alkyl or optionally substituted aryl; $R^2$ is optionally substituted $C_{1-6}$-alkyl, optionally substituted aralkyl, or —$COR^3$, wherein $R^3$ is optionally substituted $C_{1-6}$-alkyl, optionally substituted aralkyl, or optionally substituted aryl; $R^4$ and $R^5$ independently are hydrogen, halogen, perhalomethyl, optionally substituted $C_{1-6}$-alkyl, hydroxy, optionally substituted $C_{1-6}$-alkoxy, nitro, cyano, amino, optionally substituted mono- or optionally substituted di-$C_{1-6}$-alkylamino, acylamino, $C_{1-6}$-alkoxycarbonyl, carboxy or carbamoyl; n is 0, and m is 1, and methods of treating or preventing a disease of the endocrinologic system.

45 Claims, No Drawings

4,5,6,7-TETRAHYDRO-THIENO[3,2-C] PYRIDINE DERIVATIVES, THEIR PREPARATION AND USE

CROSS-REFERENCE TO RELATED APPLICATIONS

This application claims priority of U.S. provisional application Ser. Nos. 60/041,641 and 60/067,809 filed on Mar. 27, 1997 and Dec. 8, 1997, respectively, and of Danish application nos. 0249/97 and 1365/97 filed Mar. 7, 1997 and Nov. 27, 1997, respectively, the contents of which are fully incorporated herein by reference.

FIELD OF THE INVENTION

The present invention relates to 4,5,6,7-tetrahydro-thieno [3,2-c]pyridine derivatives, to methods for their preparation, to compositions comprising the compounds, to the use of these compounds as medicaments and their use in therapy, e.g. to their use for treatment of humain and animal disorders. The invention relates to modulation of the activity of molecules with glucose-6-phosphate recognition units, including glucose-6-phosphatases (G-6-Pases) in in vitro systems, microorganisms, eukaryotic cells, whole animals and human beings, especially in the treatment of diseases related to glucose metabolic pathways.

BACKGROUND OF THE INVENTION

Glucose is the major energy substrate in mammals and regulation of blood glucose levels within a narrow range seems to be of crucial importance to devoid serious physiological complications as seen in diabetes (DeFronzo, Bonadonna, & Ferrannini. 1992). Blood glucose homeostasis is maintained by dietary intake of carbohydrates, the uptake of glucose by peripheral tissues and the brain, and storage or release of glucose from the liver. The liver therefore seems to play a major role in the homeostatic regulation of blood glucose levels, Gluconeogenesis and glycogenolysis are the two metabolic pathways from which glucose can be produced in the liver. These pathways are under tight hormonal control. Insulin resistance and insulin deficiency have a substantial impact on glucose production in the liver (Consoli. 1992; DeFronzo, Bonadonna, & Ferrannini. 1992; Clore, Stillman, Stevens, Blackard, Levy, & Richmond. 1996). Glucose-6-phosphatase (G-6-Pase) catalyses the terminal step in the above mentioned pathways by converting glucose-6-phosphate (G-6-P) to glucose, and is largely situated in the liver, with some expression in the kidney after prolonged fasting. The G-6-Pase is a multicomponent system comprising of the G-6-Pase catalytic enzyme with its active site located at the luminal site of the endoplasmic reticulurn (microsomal fraction), a specific transporter TI which mediates entry of G-6-P into the luminal compartment, and transporter T2 and T3 which mediates export to the cytosol of inorganic phosphate and glucose, respectively (Nordlie, Bode, & Foster. 1993; Sukalski & Norcllie. 1989). It has been shown that the rate of hydrolysis of G-6-P and the hepatic glucose output were increased under diabetic conditions (Lyall, Grant, Scott, & Burchell. 1992; DeFronzo, Bonadonna, & Ferrannini. 1992). The increased activity could mainly be accounted for by increased G-6-Pase catalytic enzyme protein (Argaud, Zhang, Pan, Maitra, Pilkis, 4& Lange. 1996; Burchell & Cain. 1985). This makes G-6-Pase enzyme a potential target in control of excess glucose production seen in diabetes.

BIBLIOGRAPHY

Argaud, D., Zhang, Q., Pan, W., Maitra, S., Pilkis, S. J., & Lange, A. (1996). Regulation of rat liver glucose-6-phosphatase gene expression in different nutritional and hormonal states,. *Diabetes,* 45:1563–1571.

Arion, J. M., Lange, A. J., & Walls, H. E. (1980). Microsomal membrane integrity and the interactions of phlorizin with the glucose-6-phosphatase system. *J Biol Chem,* 255:10387–10395.

Burchell, A., & Cain, D. I. (1985). Rat hepatic microsomal glucose-6-phosphatase protein levels are increased in streptozotocin-induced diabetes. *Diabetologia,* 28: (852). 856 Clore, J. N., Stillman, J. S., Stevens, W., Blackard, W. G., Levy, J., & Richmond, V. A. (1996). Chronic hyperinsulinemia supresses glucose-6-phosphatase mRNA. *Diabetes,* 44 (suppl 1):253A Consoli, A. (1992). Role of liver in pathophysiology of NIDDM. *Diabetes Care,* 15:430–441.

DeFronzo, R. A., Bonadonna, R. C., & Ferrannini, E. (1992). Pathogenesis of NIDDM: A Balanced overview. *Diabetes Care,* 15:318–368.

Lyall, H., Grant, A., Scott, H. M., & Burchell, A. (1992). Regulation of the hepatic microsomal glucose-6-phosphatase enzyme. *Biochem Soc Trans,* 20, 271S (abstract).

Nordlie, R. C., Bode, A. M., & Foster, J. D. (1993). Recent advances in hepatic glucose 6-phosphatase regulation and function. *Proc Soc Exp Biol Med,* 203:274–285.

Sukalski, K. A., & Nordlie, R. C. (1989). Glucose-6-phosphatase: Two concepts of membrane function relationship. In A. Meister (Ed.), *Advances in Enzymology and related areas of molecular biology.* (pp. 93–117). New York: John Wiley and Sons.

DESCRIPTION OF THE INVENTION

The present invention relates to compounds of the general formula I:

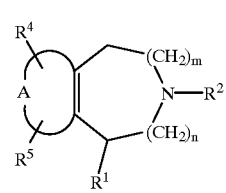

(I)

wherein

A together with the double bond of formula I forms a cyclic system selected from the group consisting of benzene, thiophene, furan, pyridine, pyrimidine, pyrazine, pyridazine, pyrrole, indole, pyrazole, imidazole, oxazole, isoxazole or thiazole, $R^1$ is $C_{1-6}$-alkyl, or aryl, optionally substituted with one or more substituents, $R^2$ is $C_{1-6}$-alkyl, aralkyl, or $COR^3$ optionally substituted with one or more substituents, $R^3$ is $C_{1-6}$-alkyl, aralkyl, or aryl, optionally substituted with one or more substituents, $R^4$ and $R^5$ independently are hydrogen, halogen, perhalomethyl, optionally substituted $C_{1-6}$-alkyl, hydroxy, optionally substituted $C_{1-6}$-alkoxy, nitro, cyano, amino, optionally substituted mono- or di-$C_{1-6}$-alkylamino, acylamino, $C_{1-6}$-alkoxycarbonyl, carboxy or carbamoyl, n is 0, 1, or 2, and m is 0, 1,or 2, or a salt thereof with a pharmaceutically acceptable acid or base, or any optical isomer or mixture of optical isomers, including a racemic mixture, or any tautomeric form.

Within its scope the invention includes all isomers of compounds of formula I, some of which are optically active, and also their mixtures including racemic mixture thereof.

The scope of the invention also includes all tautomeric forms of the compounds of formula I.

The compounds according to the invention may optionally exist as pharmaceutically acceptable salts including pharmaceutically acceptable acid addition salts, such as hydrochloric, hydrobromic, hydroiodic, phosphoric, sulfuric, acetic, trifluoroacetic, trichloroacetic, oxalic, maleic, pyruvic, malonic, succinic, citric, tartaric, fumaric, mandelic, benzoic, cinnamic, methanesulfonic, ethanesulfonic, picric and the like, and include the pharmaceutically acceptable salts listed in Journal of Pharmaceutical Science, 66, 2 (1977) and incorporated herein by reference; pharmaceutically acceptable metal salts, such as lithium, sodium, potassium, or magnesium salts and the like; or—optionally alkylated—ammonium salts; or amine salts of the compounds of this invention, such as the sodium, potassium, $C_{1-6}$-alkylamine, di ($C_{1-6}$-alkyl) amine, tri ($C_{1-6}$-alkyl) amine and the four (4) corresponding omegahydroxy analogues (e.g. methylamine, ethylamine, propylamine, dimethylamine, diethylamine, dipropylamine, trimethylamine, triethylamine, tripropylamine, di(hydroxyethyl)amine, and the like; Also intended as pharmaceutically acceptable acid addition salts are the hydrates which the present compounds are able to form. The acid addition salts may be obtained as the direct products of compound synthesis. In the alternative, the free base may be dissolved in a suitable solvent containing the appropriate acid, and the salt isolated by evaporating the solvent or otherwise separating the salt and solvent. The compounds of this invention may form solvates with standard low molecular weight solvents using methods known to the skilled artisan.

The term "$C_{1-6}$-alkyl" as used herein, alone or in combination, refers to a straight or branched, saturated or unsaturated hydrocarbon chain. The $C_{1-6}$-alkyl residues include aliphatic hydrocarbon residues, unsaturated aliphatic hydrocarbon residues, alicyclic hydrocarbon residues. Examples of the aliphatic hydrocarbon residues include saturated aliphatic hydrocarbon residues having 1 to 6 carbon atoms such as methyl, ethyl, n-propyl, isopropyl, n-butyl, isobutyl, sec.butyl, tert.butyl, n-pentyl, isopentyl, neopentyl, tert.pentyl, n-hexyl, isohexyl. Example of the unsaturated aliphatic hydrocarbon residues include those having 2 to 6 carbon atoms such as ethenyl, 1-propenyl, 2-propenyl, 1-butenyl, 2-butenyl, 3-butenyl, 2-methyl-1-propenyl, 1-pentenyl, 2-pentenyl, 3-pentenyl, 4-pentenyl, 3-methyl-2-butenyl, 1-hexenyl, 3-hexenyl, 2,4-hexadienyl, 5-hexenyl, ethynyl, 1-propionyl, 2-propionyl, 1-butynyl, 2-butynyl, 3-butynyl, 1-pentynyl, 2-pentynyl, 3-pentynyl, 4-pentynyl, 1-hexynyl, 3-hexynyl, 2,4-hexadiynyl, 5-hexynyl. Examples of the alicyclic hydrocarbon residue include saturated alicyclic hydrocarbon residues having 3 to 6 carbon atoms such as cyclopropyl, cyclobutyl, cyclopentyl, cyclohexyl; and $C_{5-6}$ unsaturated alicyclic hydrocarbon residues having 5 to 6 carbon atoms such as 1-cyclopentenyl, 2-cyclopentenyl, 3-cyclopentenyl, 1-cyclohexenyl, 2-cyclohexenyl, 3-cyclohexenyl.

The terms "lower alkyl" and "lower alkoxy" mean $C_{1-6}$-alkyl and $C_{1-6}$-alkoxy, respectively.

The term "aryl" as used herein refers to an aryl which can be optionally substituted or a heteroaryl which can be optionally substituted and includes phenyl, biphenyl, indene, fluorene, naphthyl (1-naphthyl, 2-naphthyl), anthracene (1-anthracenyl, 2-anthracenyl, 3-anthracenyl), pyrrolyl (2-pyrrolyl), pyrazolyl (e.g. 3-pyrazolyl, 4-pyrazolyl and 5-pyrazolyl), imidazolyl (1-imidazolyl, 2-imidazolyl, 4-imidazolyl, 5-imidazolyl), triazolyl (1,2,3-triazol-1-yl, 1,2,3-triazol-2-yl 1,2,3-triazol-4-yl, 1,2,4-triazol-3-yl), oxazolyl (2-oxazolyl, 4-oxazolyl, 5-oxazolyl), thiazolyl (2-thiazolyl, 4-thiazolyl, 5-thiazolyl), pyridyl (2-pyridyl, 3-pyridyl, 4-pyridyl), pyrimidinyl (2-pyrimidinyl, 4-pyrimidinyl, 5-pyrimidinyl, 6-pyrimidinyl), pyrazinyl, pyridazinyl (3-pyridazinyl, 4-pyridazinyl, 5-pyridazinyl), quinolyl (2-quinolyl, 3-quinolyl, 4quinolyl, 5-quinolyl, 6-quinolyl, 7-quinolyl, 8-quinolyl), isoquinolyl (1-isoquinolyl, 3-isoquinolyl, 4-isoquinolyl, 5-isoquinolyl, 6-isoquinolyl, 7-isoquinolyl, 8-isoquinolyl), benzo[b]furanyl (2-benzo[b]furanyl, 3-benzo[b]furanyl, 4-benzo[b]furanyl, 5-benzo[b]furanyl, 6-benzo[b]furanyl, 7-benzo[b]furanyl), 2,3-dihydro-benzo[b]furanyl (2-(2,3-dihydro-benzo[b]furanyl), 3-(2,3-dihydrobenzo[b]furanyl), 4-(2,3-dihydro-benzo[b]furanyl), 5-(2,3-dihydro-benzo[b]furanyl), 6-(2,3-dihydro-benzo[b]furanyl), 7-(2,3-dihydro-benzo[b]furanyl), benzo[b]thiophenyl (2-benzo[b]thiophenyl, 3-benzo[b]thiophenyl, 4-benzo[b]thiophenyl, 5-benzo[b]thiophenyl, 6-benzo[b]thiophenyl, 7-benzo[b]thiophenyl), 2,3-dihydro-benzo[b]thiophenyl (2-(2,3-dihydrobenzo[b]thiophenyl), 3-(2,3-dihydro-benzo[b]thiophenyl), 4-(2,3-dihydro-benzo[b]thiophenyl), 5-(2,3-dihydro-benzo[b]thiophenyl), 6-(2,3-dihydro-benzo[b]thiophenyl), 7-(2,3-dihydrobenzo[b]thiophenyl), indolyl (1-indolyl, 2-indolyl, 3-indolyl, 4-indolyl, 5-indolyl, 6-indolyl, 7-indolyl), indazole (1-indazolyl, 3-indazolyl, 4-indazolyl, 5-indazolyl, 6-indazolyl, 7-indazolyl), benzimidazolyl (1-benzimidazolyl, 2-benzimidazolyl, 4-benzimidazolyl, 5-benzimidazolyl, 6-benzimidazolyl, 7-benzimidazolyl, 8-benzimidazolyl), benzoxazolyl (1-benzoxazolyl, 2-benzoxazolyl), benzothiazolyl (1-benzothiazolyl, 2-benzothiazolyl, 4-benzothiazolyl, 5-benzothiazolyl, 6-benzothiazolyl, 7-benzothiazolyl), carbazolyl (1-carbazolyl, 2-carbazolyl, 3-carbazolyl, 4-carbazolyl), 5H-dibenz[b,f]azepine (5H-dibenz[b,f]azepin-1-yl, 5H-dibenz[b,f]azepine-2-yl, 5H-dibenz[b,f]azepine-3-yl, 5H-dibenz[b,f]azepine-4-yl, 5H-dibenz[b,f]azepine-5-yl), 10,11-dihydro-5H-dibenz[b,f]azepine (10,11-dihydro-5H-dibenz[b,f]azepine-1 -yl, 10,11-dihydro-5H-dibenz[b,f] azepine-2-yl, 10,11-dihydro-5H-dibenz[b,f]azepine-3-yl, 10,11-dihydro-5H-dibenz[b,f]azepine-4-yl, 10,11-dihydro-5H-dibenz[b,f]azepine-5-yl), furanyl (e.g. 2-furanyl, 3-furanyl, 4-furanyl and 5-furanyl), thienyl (e.g. 2-thienyl, 3-thienyl, 4-thienyl and 5-thienyl) optionally substituted with one or more substituents.

The term "optionally substituted" as used herein means an aryl residue as defined above or a $C_{1-6}$-alkyl residue as defined above that may be unsubstituted or may have 1 or more preferably 1 to 5 substituents, which are the same as or different from one another. Examples of these substituents include, halogen (fluorine, chlorine, bromine, iodine), hydroxyl, cyano, nitro, trifluoromethyl, carbamoyl, $C_{1-4}$-acyl (e.g. acetyl, propionyl, isopropionyl), $C_{1-6}$-alkoxy (e.g. methoxy, ethoxy, propoxy, isopropoxy, butoxy, and tert.butoxy), $C_{1-6}$-alkyl as defined above, $C_{1-6}$-alkoxycarbonyl (e.g. ones having 2 to 6 carbon atoms such as methoxycarbonyl, ethoxycarbonyl, and propoxycarbonyl), $C_{1-6}$-alkanoyloxy (e.g. ones having 2 to 6 carbon atoms such as acetyloxy, propionyloxy, isopropionyloxy), $C_{1-4}$-alkylthio (e.g. ones having 1 to 4 carbon atoms such as methylthio, ethylthio, propylthio, and isopropylthio), $C_{1-4}$-alkylsulphinyl (e.g. ones having 1–4 carbon atoms such as methylsulphinyl and ethylsulphinyl), $C_{1-4}$-alkylsulphonyl (e.g. ones having 1–4 carbonatoms such as methylsulphonyl and ethylsulphonyl), $C_{1-4}$-alkylamino (e.g. one having 1 to 4 carbon atoms such as methylamino, ethylylamino, dimethylamino, and 1-pyrrolidinyl), aminoalkyl (e.g. one having an amino containing group connected to a $C_{1-4}$-alkyl group as defined above, such as 2-dimethylaminoethyl and 1-pyrrolidinylmethyl), aminoalkoxy (e.g. one having an amino containing group connected via a $C_{1-6}$-alkyl group as defined above to an oxygen atom, such as 2-dimethylaminoethoxy, 2-(4-morpholinyl) ethoxy and 1-pyrrolidinylmethoxy), aryl as defined above (e.g. phenyl and 4-pyridinyl), aryloxy (e.g. phenyloxy), and aralkyloxy (e.g. benzyloxy).

The term "halogen" as used herein means fluorine, chlorine, bromine or iodine.

The term "perhalomethyl" as used herein means trifluoromethyl, trichloromethyl, tribromomethyl or triiodomethyl.

The term "perhalomethoxy" as used herein means trifluoromethoxy, trichloromethoxy, tribromomethoxy or triiodomethoxy.

The term "aralkyl" as used herein refers to an optionally substituted aryl residue as defined above, connected to an optionally substituted $C_{1-8}$alkyl as defined above. Examples of the aralkyl residue include benzyl, 2-phenylethyl, 2-phenylethenyl, 3-(2-pyridyl)propyl, 3-phenylpropyl, 1-naphtylmethyl, 2-(1-naphtyl)ethyl and the like.

The term "$C_{1-6}$-alkoxy" as used herein, alone or in combination, refers to a straight or branched monovalent substituent comprising a $C_{1-6}$-alkyl group linked through an ether oxygen having its free valence bond from the ether oxygen and having 1 to 6 carbon atoms e.g. methoxy, ethoxy, propoxy, isopropoxy, butoxy, pentoxy.

The term "carbamoyl" as used herein refers to a carbamoyl which can be optionally substituted by one or two residues selected from the list consisting of optionally substituted $C_{1-6}$-alkyl as defined above, optionally substituted aryl as defined above and optionally substituted aralkyl as defined above.

In a preferred embodiment the invention relates to compounds of general formula (I) in which A is selected from benzene or thiophene.

In another preferred embodiment the invention relates to compounds of general formula (I), wherein $R^1$ is optionally substituted phenyl.

In another preferred embodiment the invention relates to compounds of general formula (I), wherein each one of $R^1$, $R^2$, and $R^3$ is substituted with one or more substituents.

In another preferred embodiment the invention relates to compounds of general formula (I), wherein the substituents of $R^1$ is halogen, perhalomethyl, perhalomethoxy, or $C_{1-6}$-alkoxy.

In another preferred embodiment the invention relates to compounds of general formula (I), wherein the substituents of $R^1$ are selected from the group consisting of hydrogen, halogen, perhalomethyl, perhalomethoxy, or $C_{1-6}$-alkoxy.

In another preferred embodiment the invention relates to compounds of general formula (I), wherein the substituents of $R^1$ are selected from from the group consisting of chloro, trifluoromethyl, methoxy, trifluoromethoxy.

In another preferred embodiment the invention relates to compounds of general formula (I), wherein $R^1$ is selected from the group consisting of phenyl, 4-chlorophenyl, 4-trifluoromethylphenyl, and 4-trifluoromethoxyphenyl.

In another preferred embodiment the invention relates to compounds of general formula (I), wherein $R^1$ is 2,3-dihydrobenzofuran or 4-methoxyphenyl.

In another preferred embodiment the invention relates to compounds of general formula (I), wherein $R^2$ is $COR^3$ or $(CH_2)_q$-aryl, and q is 0, 1, 2, 3, 4, 5, or 6.

In another preferred embodiment the invention relates to compounds of general formula (I), wherein $R^3$ is selected from the group consisting of phenyl, 3-methoxyphenyl, 4-methoxyphenyl, 4-chlorophenyl, 4-trifluoromethylphenyl, 4-(2-dimethylaminoethoxy)phenyl, or 4-(2-morpholin-4-ylethoxy)phenyl.

In another preferred embodiment the invention relates to compounds of general formula (I), wherein $R^3$ is selected from the group consisting of 4-methylphenyl, 3,4-dimethoxyphenyl, 4-ethoxyphenyl, 4-fluorophenyl, 4-trifluoromethylphenyl, dimethylaminophenyl, 4-(2-carboxyethenyl)phenyl, 4-(2-dimethylaminoethoxy)phenyl, 4-(2-morpholin-4-ylethoxy)phenyl, 1H-indol-5-yl, 3-chloro-4-methoxyphenyl, and 1 H-benzimidazol-5-yl.

In another preferred embodiment the invention relates to compounds of general formula (I), wherein $R^4$ and $R^5$ independently is hydrogen, chloro, or methoxy.

In another preferred embodiment the invention relates to compounds of general formula (I), wherein n is 0 or 1 and m is 0 or 1.

In another preferred embodiment the invention relates to compounds of general formula (I), wherein n is 0 and m is or 1.

In a another preferred embodiment the invention relates to compounds of general formula (Ia):

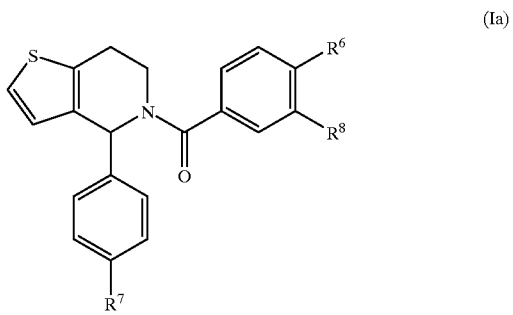

(Ia)

wherein $R^7$ is hydrogen, halogen, preferably chloro, methoxy, perhalomethoxy, preferably trifluoromethoxy, perhalomethyl, preferably trifluoromethyl, diloweralkylamino, preferably dimethylamino, or nitro, and $R^6$ and $R^8$ independently are hydrogen, hydroxy, halogen, preferably chloro, bromo or fluoro, methyl, tert-butyl, phenyl, dimethylamino, methoxy, ethoxy, 2-dimethylaminoethoxy, 2-carboxyethenyl, 2-morpholin-4-ylethoxy, perhalomethyl, preferably trifluoromethyl, perhalomethoxy, preferably trifluoromethoxy, carboxy, cyano, methylthio, methylsulfonyl, acetamido, nitro, acetyl, acetoxy, or hydroxymethyl.

In another preferred embodiment the invention relates to compounds of general formula (Ia)::

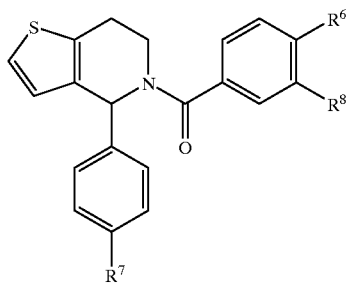

(Ia)

wherein $R^7$ is halogen, perhalomethyl, or perhalomethoxy and $R^6$ and $R^8$ independently are hydrogen, methoxy, ethoxy, hydroxy, fluoro, chloro, bromo, iodo, methyl, trifluoromethyl, dimethylamino, 2-carboxyethenyl, 2-dimethylaminoethoxy, or 2-morpholin-4-ylethoxy.

$R^7$ is preferably selected from the group consisting of chloro, methoxy and trifluoromethyl, more preferably trifluoromethoxy.

Preferably, $R^6$ and $R^8$ are independently hydrogen, methoxy, chloro, trifluoromethyl, 2-dimethylaminoethoxy, or 2-morpholin-4-ylethoxy.

In another preferred embodiment the invention relates to compounds of general formula (Ib):

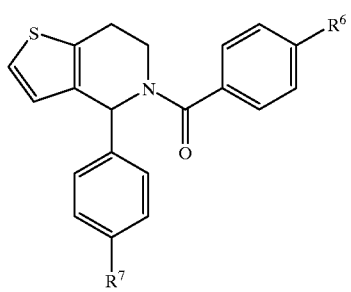

(Ib)

wherein $R^7$ is as described above, and $R^6$ is hydroxy, halogen, preferably chloro or fluoro, methyl, dimethylamino, methoxy, ethoxy, perhalomethyl, preferably trifluoromethyl, perhalomethoxy, preferably trifluoromethoxy, cyano, methylthio, acetyl, acetoxy, or hydroxymethyl.

In another preferred embodiment the invention relates to compounds of general formula (Ic):

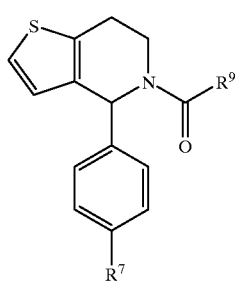

(Ic)

wherein $R^7$ is as defined above, and $R^9$ is 4-pyridyl, 5-hydroxypyrazin-2-yl, 5-chloro-6-hydroxypyridin-3-yl, 2-chloropyridin-3-yl, benzofuran-2-yl, benzothiophen-2-yl-, 7-methoxybenzofuran-2-yl, indolyl, preferably 1H-indol-5-yl, benzimidazol, preferably 1H-benzimidazol-5-yl or thienyl, preferably 5-chlorothiophen-2-yl.

In another preferred embodiment the invention relates to compounds of general formula (Ic):

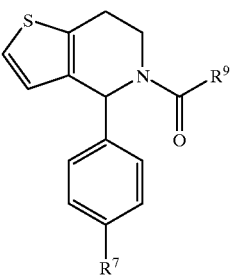

(Ic)

wherein $R^7$ is as defined above and $R^9$ is indolyl, preferably 1H-indol-5-yl or benzimidazol, preferably 1H-benzimidazol-5-yl.

In the compounds of formula (IC) $R^9$ is preferably benzothiophen-2-yl, indolyl, preferably 1H-indol-5-yl, or benzimidazol, preferably 1H-benzimidazol-5-yl.

In another preferred embodiment the invention relates to compounds of general formula (Id):

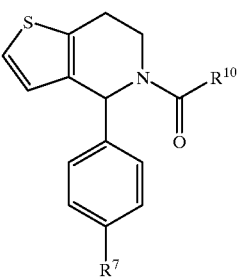

(Id)

wherein $R^7$ is as defined above, and $R^{10}$ is optionally substituted aralkyl as defined above, preferably 2-(4-methoxyphenyl)-ethenyl, 2-(3-methoxyphenyl)-ethenyl, 2-(4-chlorophenyl)-ethenyl, 2-(4-fluorophenyl)-ethenyl, 2-(4-trifluoromethylphenyl)-ethenyl, 2-(4-methoxyphenyl)-ethyl, 2-(4-chlorophenyl)-ethyl, 4-chlorobenzyl, 4-methoxybenzyl, 2-(2-furyl)-ethenyl, 2-(4,5-dimethyl-2-furyl)-ethenyl, 2-(5-methyl-2-furyl)-ethenyl, 2-(3-furyl)-ethenyl, 2-(2-thienyl)-ethenyl, or 2-(3-thienyl)-ethenyl.

In another preferred embodiment the invention relates to compounds of general formula (Id):

(Id)

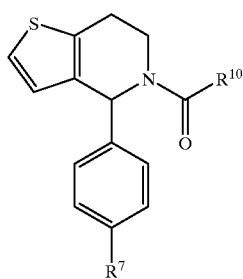

wherein $R^7$ is as defined above, and $R^{10}$ is 4-methoxyphenyl-2-ethenyl.

In the compounds of formula (Id) $R^7$ is preferably as defined above and $R^{10}$ is optionally substituted aralkyl as defined above, preferably 2-(4-methoxyphenyl)-ethenyl, 2-(2-furyl)-ethenyl, 2-(5-methyl-2-furyl)-ethenyl, 2-(3-furyl)-ethenyl, or 2-(3-thienyl)-ethenyl.

In another preferred embodiment the invention relates to compounds of general formula (Ie):

(Ie)

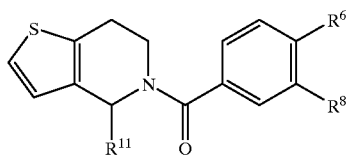

wherein $R^{11}$ is pyridyl, preferably 4-pyridyl, and
$R^6$ and $R^8$ independently are hydrogen, hydroxy, halogen, preferably chloro, bromo or fluoro, methyl, tert-butyl, phenyl, dimethylamino, methoxy, ethoxy, 2-dimethylaminoethoxy, 2-carboxyethenyl, 2-morpholin-4-ylethoxy, perhalomethyl, preferably trifluoromethyl, perhalomethoxy, preferably trifluoromethoxy, carboxy, cyano, methylthio, methylsulfonyl, acetamido, nitro, acetyl, acetoxy, or hydroxymethyl.

In another preferred embodiment the invention relates to compounds of general formula (If):

(If)

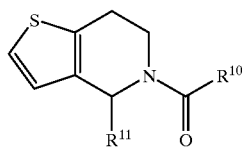

wherein $R^{10}$ is optionally substituted aralkyl as defined above, preferably 2-(4-methoxyphenyl)-ethenyl, 2-(3-methoxyphenyl)-ethenyl, 2-(4-chlorophenyl)-ethenyl, 2-(4-fluorophenyl)-ethenyl, 2-(4-trifluoromethylphenyl)ethenyl, 2-(4-methoxyphenyl)-ethyl, 2-(4-chlorophenyl)-ethyl, 4-chlorobenzyl, 4-methoxybenzyl, 2-(2-furyl)-ethenyl, 2-(4,5-dimethyl-2-furyl)-ethenyl, 2-(5-methyl-2-furyl)-ethenyl, 2-(3-furyl)-ethenyl, 2-(2-thienyl)-ethenyl, or 2-(3-thienyl)-ethenyl, and $R^{11}$ is pyridyl, preferably 4-pyridyl.

In another preferred embodiment the invention relates to compounds of general formula (Ig):

(Ig)

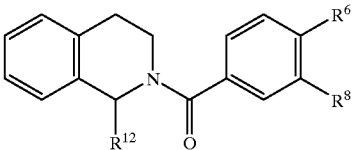

wherein $R^{12}$ is aryl or aralkyl, and
$R^6$ and $R^8$ independently are hydrogen, hydroxy, halogen, preferably chloro, bromo or fluoro, methyl, tert-butyl, phenyl, dimethylamino, methoxy, ethoxy, 2-dimethylaminoethoxy, 2-carboxyethenyl, 2-morpholin-4-ylethoxy, perhalomethyl, preferably trifluoromethyl, perhalimethoxy, preferably trifluoromethoxy, carboxy, cyano, methylthio, methylsulfonyl, acetamido, nitro, acetyl, acetoxy, or hydroxymethyl.

In another preferred embodiment the invention relates to compounds of general formula (Ih):

(Ih)

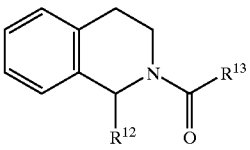

wherein $R^{12}$ is aryl, preferably 4-trifluoromethoxyphenyl, or aralkyl, preferably benzyl, and
$R^{13}$ is aralkyl as defined above, preferably 2-(4-methoxyphenyl)-ethenyl, 2-(3-methoxyphenyl)-ethenyl, 2-(4-chlorophenyl)-ethenyl, 2-(4-fluorophenyl)-ethenyl, 2-(4-trifluoromethylphenyl)-ethenyl, 2-(4-methoxyphenyl)-ethyl, 2-(4-chlorophenyl)-ethyl, 4-chlorobenzyl, 4-methoxybenzyl, 2-(2-furyl)-ethenyl, 2-(4,5dimethyl-2-furyl)-ethenyl, 2-(5-methyl-2-furyl)-ethenyl, 2-(3-furyl)ethenyl, 2-(2-thienyl)-ethenyl, or 2-(3-thienyl)-ethenyl.

The most preferred compounds of the invention are:
(+)-[4-(4-Chlorophenyl)-4,5,6,7-tetrahydro-thieno[3,2-c]pyridin-5-yl]-(4-methoxyphenyl)-methanone, (compound No. 1),
(−)-[4-(4-Chlorophenyl)4,5,6,7-tetrahydro-thieno[3,2-c]pyridin-5-yl]-(4-methoxyphenyl)-methanone, (compound No. 2),
(+)-[4-(4-Methoxyphenyl)-4,5,6,7-tetrahydro-thieno[3,2-c]pyridin-5-yl]-(4-trifluoromethylphenyl)-methanone, (compound No. 3),
(−)-[4-(4-Methoxyphenyl)4,5,6,7-tetrahydro-thieno[3,2-c]pyridin-5-yl]-(4-trifluoromethylphenyl)-methanone, (compound No. 4),
[4-(4-Trifluoromethylphenyl)4,5,6,7-tetrahydro-thieno[3,2-c]pyridin-5-yl]-(4-methoxyphenyl)-methanone, (compound No. 5),
(+)-[4-(4-Trifluoromethylphenyl)4,5,6,7-tetrahydro-thieno[3,2-c]pyridin-5-yl]-(4-methoxyphenyl)-methanone, (compound No. 6),
(−)-[4-(4-Trifluoromethylphenyl)-4,5,6,7-tetrahydro-thieno[3,2-c]pyridin-5-yl]-(4-methoxyphenyl)-methanone, (compound No. 7),
[4-(4-Trifluoromethylphenyl)-4,5,6,7-tetrahydro-thieno[3,2-c]pyridin-5-yl]-(3-methoxyphenyl)-methanone, (compound No. 8), (+)-[4-(4-Trifluoromethylphenyl)4,5,6,7-tetrahydro-thieno[3,2-c]pyridin-5-yl]-(3-methoxyphenyl)-methanone, (compound No. 9), (−)-[4-(4-Trifluoromethylphenyl)4,5,6,7-tetrahydro-thieno[3,2-c]pyridin-5-yl]-(3-methoxyphenyl)-methanone, (compound No. 10),

[4-(4-Chlorophenyl)4,5,6,7-tetrahydro-thieno[3,2-c]pyridin-5-yl]-phenyl-methanone, (compound No. 11), (+)-[4-(4-Chlorophenyl)4,5,6,7-tetrahydro-thieno[3,2-c]pyridin-5-yl]-phenyl-methanone, (compound No. 12), (−)-[4-(4-Chlorophenyl)4,5,6,7-tetrahydro-thieno[3,2-c]pyridin-5-yl]-phenyl-methanone, (compound No. 13), (4-(2-Dimethylaminoethoxy)phenyl)-[4-(4-trifluoromethylphenyl)4,5,6,7-tetrahydrothieno[3,2-c]pyridin-5-yl]-methanone, (compound No. 14), (+)-(4-(2-Dimethylaminoethoxy)phenyl)-[4-(4-trifluoromethylphenyl)-4,5,6,7-tetrahydrothieno[3,2-c]pyridin-5-yl]-methanone, (compound No. 15), (−)-(4-(2-Dimethylaminoethoxy)phenyl)-[4-(4-trifluoromethylphenyl)4,5,6,7-tetrahydrothieno[3,2-c]pyridin-5-yl]-methanone, (compound No. 16),

[4-(4-Chlorophenyl)4,5,6,7-tetrahydro-thieno[3,2-c]pyridin-5-yl]-(4-(2-[2-morpholin-4-ylethoxy)phenyl]-methanone, (compound No. 17), (+)-[4-(4-Chlorophenyl)4,5,6,7-tetrahydro-thieno[3,2-c]pyridin-5-yl]-(4-(2-[2-morpholin-4-ylethoxy)phenyl]-methanone, (compound No. 18), (−)-[4-(4-Chlorophenyl)-4,5,6,7-tetrahydro-thieno[3,2-c]pyridin-5-y]-(4-(2-[2-morpholin-4-ylethoxy)phenyl]-methanone, (compound No. 19),

[4-(4-Trifluoromethylphenyl)4,5,6,7-tetrahydro-thieno[3,2-c]pyridin-5-yl]-(4-dimethylaminophenyl)-methanone, (compound No 20), 3-{4-[4-(4-Chlorophenyl)4,5,6,7-tetrahydro-thieno[3,2-c]pyridine-5-carbonyl]phenyl}acrylic acid, (compound No 21), (4-Chlorophenyl)-[4-(4-chlorophenyl)4,5,6,7-tetrahydro-thieno[3,2-c]pyridin-5-yl]-methanone, both the racemate, the two pure enantiomers, and mixtures thereof (compound No 22),

[4-(4-Trifluoromethylphenyl)4,5,6,7-tetrahydro-thieno[3,2-c]pyridin-5-yl]-(4-methoxyphenyl)-methanone, (compound No. 24),

[4-(4-Trifluoromethylphenyl)4,5,6,7-tetrahydro-thieno[3,2-c]pyridin-5-yl]-(4-methoxyphenyl)-methanone, (compound No. 25),

[4-(2-Dimethylaminoethoxy)-phenyl]-[4-(4-trifluoromethylphenyl)-4,5,6,7-tetrahydrothieno[3,2-c]pyridin-5-yl]-methanone, (compound No. 26),

[4-(2-Dimethylaminoethoxy)-phenyl]-[4-(4-trifluoromethylphenyl)-4,5,6,7-tetrahydrothieno[3,2-c]pyridin-5-yl]-methanone, (compound No. 27),

[4-(4-Chlorophenyl)-4,5,6,7-tetrahydro-thieno[3,2-c]pyridin-5-yl]-[4-(2-morpholin-4-ylethoxy)phenyl]-methanone, (compound No. 28),

[4-(4-Chlorophenyl)-4,5,6,7-tetrahydro-thieno[3,2-c]pyridin-5-yl]-[4-(2-morpholin-4-ylethoxy)phenyl]-methanone, (compound No. 29),

[4-(4-Trifluoromethoxyphenyl)-4,5,6,7-tetrahydro-thieno[3,2-c]pyridin-5-yl]-(4-methoxyphenyl)-methanone, (compound No. 30),

[4-(4-Trifluoromethoxyphenyl)-4,5,6,7-tetrahydro-thieno[3,2-c]pyridin-5-yl]-(4-methoxyphenyl)-methanone, (compound No. 31),

[4-(4-Trifluoromethoxyphenyl)-4,5,6,7-tetrahydro-thieno[3,2-c]pyridin-5-yl]-(4-methoxyphenyl)-methanone, (compound No. 32),

[4-(4-Chlorophenyl)-4,5,6,7-tetrahydro-thieno[3,2-c]pyridin-5-yl]-(1H-indol-5-yl)-methanone, (compound No. 33), (1H-Indol-5-yl)-[4-(4-trifluoromethoxyphenyl)4,5,6,7-tetrahydro-thieno[3,2-c]pyridin-5-yl]-methanone, (compound No. 34),

[4-(4-Chlorophenyl)-4,5,6,7-tetrahydro-thieno[3,2-c]pyridin-5-yl]-(4-fluorophenyl)-methanone, (compound No. 35),

[4-(4-Trifluoromethoxyphenyl)-4,5,6,7-tetrahydro-thieno[3,2-c]pyridin-5-yl]-(4-fluorophenyl)-methanone, (compound No. 36),

[4-(4-Chlorophenyl)-4,5,6,7-tetrahydro-thieno[3,2-c]pyridin-5-yl]-[4-(2-dimethylaminoethoxy)phenyl]-methanone, (compound No. 37),

[4-(2-Dimethylaminoethoxy)phenyl]-[4-(4-trifluoromethoxyphenyl)4,5,6,7-tetrahydro-thieno[3,2-c]pyridin-5-yl]-methanone, (compound No. 38),

[7-Chloro-1-(2,3-dihydrobenzofuran-7-yl)-8-methoxy-1,2,4,5-tetrahydrobenzo[d]azepin-3-yl]-[4-(2-dimethylaminoethoxy)-phenyl]-methanone, (compound No. 39),

[4-(3,4-Dimethoxyphenyl)-4,5,6,7-tetrahydro-thieno[2,3-c]pyridin-6-yl]-[4-(2-dimethylaminoethoxy)-phenyl]-methanone, (compound No. 40), (3,4-Dimethoxyphenyl)-[4-(4-trifluoromethoxyphenyl)4,5,6,7-tetrahydro-thieno[3,2-c]pyridin-5-yl]methanone, (compound No. 41), (3-Chloro-4-methoxyphenyl)-[4-(4-trifluoromethoxyphenyl)-4,5,6,7-tetrahydro-thieno[3,2-c]pyridin-5-yl]methanone, (compound No. 42), (4-Ethoxyphenyl)-[4-(4-trifluoromethoxyphenyl)4,5,6,7-tetrahydro-thieno[3,2-c]pyridin-5-yl]methanone, (compound No. 43), (4-Methylphenyl)-[4-(4-trifluoromethoxyphenyl)4,5,6,7-tetrahydro-thieno[3,2-c]pyridin-5-yl]methanone, (compound No. 44), 3-(4-Methoxyphenyl)-1-[4-(4-trifluoromethoxyphenyl)-4,5,6,7-tetrahydro-thieno[3,2-c]pyridin-5-yl] propenone, (compound No. 45), (1H-Benzimidazol-5-yl)-[4-(4-trifluoromethoxyphenyl)-4,5,6,7-tetrahydro-thieno[3,2-c]pyridin-5-yl] methanone, (compound No. 46), and salts thereof with a pharmaceutically acceptable acid.

The compounds of the present invention are normoglycaemic agents (i.e. compounds that are able to normalise blood glucose levels from hyper-/hypoglycemic conditions) that interact with the glucose-6-phosphatase catalytic enzyme activity, and hence make them useful in the treatment and prevention of various diseases of the endocrinological system, especially ailments related to carbohydrate metabolism and especially the glucose metabolism, e.g. hyperglycaemia, diabetes mellitus, and especially non-insulin dependent diabetes mellitus (NIDDM) including long-term complications, such as retinopathy, neuropathy, nephropathy, and micro- and macroangiopathy, and hypoglycaemia resulting from, e.g., glycogen storage disease (von Gierke's Disease all types). Moreover, the present compounds are useful in the prophylactic treatment of hyperlipidaemia, hypertension, liver and bile diseases, and atherosclerosis associated with diabetes. The present compounds are especially useful in the treatment of diseases associated with an increased or reduced activity of the glucose-6-phosphatase complex, e.g. the G-6-Pase catalytic enzyme.

Accordingly, in another aspect the invention relates to a compound of the general formula I, Ia, Ib, Ic or a pharmaceutically acceptable acid addition salt or other salt as defined above thereof for use as a therapeutically acceptable substance, preferably for use as a therapeutically acceptable substance in the treatment of hyperglycaemia and treatment or prevention of diabetes.

Furthermore, the invention also relates to the use of the inventive compounds of formula I, Ia, Ib, and Ic as medicaments useful for treating hyperglycaemia and treating or preventing diabetes.

In yet another aspect, the present invention relates to methods of preparing the above mentioned compounds. Methods of preparing compounds of general formula I comprises:

Method A:

When $R^2$ is $COR^3$:

Reacting a compound of formula X with a compound of formula Y to form compounds of general formula Ib:

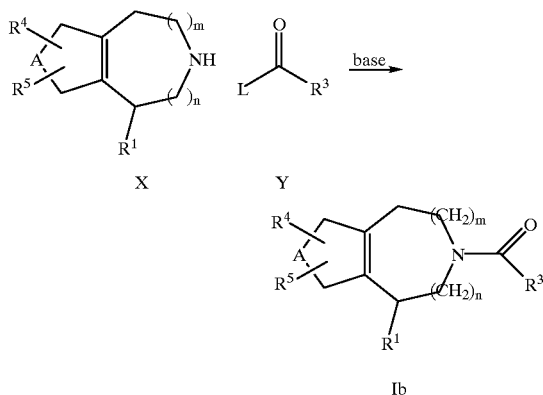

wherein $R^1$, $R^3$, $R^4$, $R^5$, n, and m are as defined above and L is a leaving group and are selected from fluorine, chlorine, bromine, iodine, 1-imidazolyl, 1,2,4-triazolyl, 1-benzotriazolyloxy, 1-(4-aza benzotriazolyl)oxy, pentafluorophenoxy, N-succinyloxy 3,4-dihydro-4-oxo-3-(1,2,3-benzotriazinyl)oxy, $R^3COO$ where $R^3$ is as defined above, or any other leaving group known to act as a leaving group in acylation reactions. The base can be either absent (i.e. compound X acts as a base) or triethylamine, N-ethyl-N,N.-diisopropylamine, N-methylmorpholine, 2,6-lutidine, 2,2,6,6-tetramethylpiperidine, potassium carbonate, caesium carbonate or any other base known to be useful in acylation reactions.

Method B:

When $R^2$ is optionally substituted $C_{1-6}$ alkyl or aralkyl:

a) Reacting a compound of formula X with a compound of formula Z in an alkylation reaction to form compounds of general formula I:

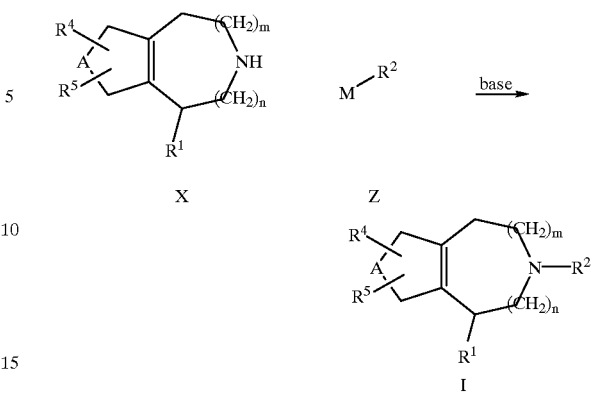

wherein $R^1$, $R^2$, $R^4$, $R^5$, n, and m are as defined above, M is a leaving group and is selected from chlorine, bromine, iodine, methanesulfonyloxy, trifluoromethanesulfonyloxy, p-toluenesulfonyloxy or any other group known to act as a leaving group in alkylation reactions. The base can be either absent (i.e. compound X acts as a base) or triethylamine, N-ethyl-N,N.-diisopropylamine, N-methylmorpholine, 2,6-lutidine, 2,2,6,6-tetramethylpiperidine, potassium carbonate, sodium carbonate, caesium carbonate or any other base known to be useful in alkylation reactions.

Method C:

Reacting a compound of formula X with an aldehyde of formula Zz in a reductive alkylation reaction to form compounds of general formula I:

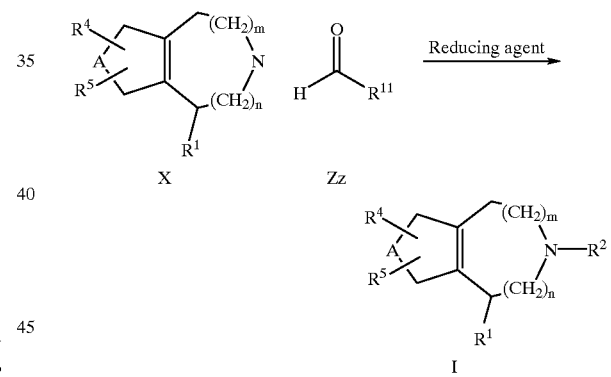

wherein $R^1$, $R^2$, $R^4$, $R^5$, n, and m are as defined above, $R^{11}$ is as defined for $R^2$ but one (1) carbon atom shorter. The reducing agent can be selected from the following list: $NaCNBH_3$, $NaBH(OAc)_3$, diborane, $BH_3$ complexes (eg. with tetrahydrofuran or dimethylsulfide), metallic sodium, or $H_2$/catalyst or any reductant known to be effective in the reductive alkylation reaction.

Or the compounds of formulae I, Ia, Ib, and Ic may be prepared by art-recognized procedures from known compounds or readily preparable intermediates.

The starting materials are either known compounds or compounds which may be prepared in analogy with the preparation of known compounds or in analogy with known methods as described by e.g. Tupper D. E. et al., *J. Heterocyclic Chem.*, 33, 1123–9 (1996), Stokker G. E., Tetrahedron Lett., 37, 5453–6 (1996), Nakagawa, M. et al., *Chem. Pharmn. Bull.*, 41, 287–91 (1993), Singh H. et al., *Heterocycles,* 23, 107–10 (1985), Skinner W. A. et al., *Can. J. Chem.*, 43, 2251–3 (1965). P. Kumar et al., *J. Heterocyclic*

Chem., 19, 677–9 (1982), L. K. Lukanov et al., *Synthesis*, 1987, 204–6, A. L. Stanley & S. P. Stanforth, *J. Heterocyclic Chem.*, 31, 1399–1400 (1994), A. K. Bose et al., *J. Org. Chem.*, 56, 6968–70 (1991), K. Kementani et al., *Heterocycles*, 3, 311–41 (1975), E. Domonguez et al., *Tetrahedron*, 43, 1943–8 (1987), J. B. Bremner et al., Aust. J. Chem., 41, 1815–26 (1988), M. J. O'Donnel et al., *Tetrahedron. Lett.*, 23, 4259–62 (1982).

Pharmacological Methods

The ability of compounds to inhibit glucose-6-phosphatase (G-6-Pase) catalytic enzyme activity from pig liver microsomes was tested in the following way:

Pig liver microsomes were prepared in a buffer containing 250 mM sucrose, 1 mM EDTA, 25 mM HEPES and 250 mg/l Bacitrazin (pH 7.5) essentially as described by Arion et al., 1980 (Arion, Lange, & Walls. 1980). Microsomes were kept at −80° C. until use.

Prior to measurement microsomes were treated with Triton X-100 (0.04%) ("disrupted microsomes"). G-6-Pase activity were assayed for 6 mn at 30° C. in a total volume of 325 $\mu$L containing 0.5 mM glucose-6-phosphate, 30 mM MES (pH 6.5), test compound and disrupted microsomes (0.05 mg). The reaction was terminated by addition of 100 $\mu$L Sigma phosphorus reagent (cat no 360-3C). This mixture was allowed to stand for 2 min, where the absorbance (A) was measured at 340 nm. All values were corrected for blank. The inhibitory effect was expressed as percent of control value, i.e. $IC_{50}$ is the concentration of a compound that produces 50% inhibition.

The compounds of the invention are preferably characterized by having a glucose-6-phosphatase inhibitory activity corresponding to an $IC_{50}$ or a $K_i$ value of less than 100 $\mu$M, Pmore preferably less than 10 $\mu$M, even more preferably less than 1 $\mu$M, still more preferably less than 100 nM.

The compounds according to the invention are effective over a wide dosage range. In general satisfactory results are obtained with dosages from about 0.05 to about 1000 or 5000 mg, preferably from about 0.1 to about 500 mg, per day. A most preferable dosage is about 5 mg to about 200 mg per day. The exact dosage will depend upon the mode of administration, form in which the compound is administered, the subject to be treated and the body weight of the subject to be treated, and the preference and experience of the physician or veterinarian in charge.

The dosage unit of the pharmaceutical compositions according to the invention typically contains from 0.05 mg to 1000 mg, preferably from 0.1 mg to 100 mg, or, preferably from 5 mg to 200 mg per day of the active ingredient, which is, preferably, a novel 4,5,6,7-tetrahydro-thieno[3,2-c]pyridine derivative as described herein or a pharmaceutically acceptable salt thereof with a pharmaceutically acceptable acid or base, or any optical isomer or mixture of optical isomers, including a racemic mixture, or any tautomeric form thereof; or the active ingredient is a previously described 4,5,6,7-tetrahydro-thieno[3,2-c]pyridine derivative or a pharmaceutically acceptable salt thereof with a pharmaceutically acceptable acid or base, or any optical isomer or mixture of optical isomers, including a racemic mixture, or any tautomeric form thereof.

The route of administration may be any route, which effectively transports the active compound to the appropriate or desired site of action, such as oral, nasal, pulmonary, transdermal or parenteral e.g. rectal, depot, subcutaneous, intravenous, intraurethral, intramuscular, intrapulmonary, intranasal, ophthalmic solution or an ointment, the oral route being preferred.

Optionally, the pharmaceutical composition of the invention may comprise a compound of formula I combined with one or more compounds exhibiting a different activity, e.g., a plasma lipid lowering compounds, sulphonylurea like compounds, or other oral agents useful in the treatment of diabetes, or other pharmacologically active material.

Pharmaceutical compositions containing a compound of the present invention may be prepared by conventional techniques, e.g. as described in *Remington: The Science and Practise of Pharmacy*, 19th Ed. 1995. The compositions may appear in conventional forms, for example capsules, tablets, aerosols, solutions, suspensions or topical applications.

Typical compositions include a compound of formula I or a pharmaceutically acceptable acid addition salt or metal salt thereof, associated with a pharmaceutically acceptable excipient which may be a carrier or a diluent or be diluted by a carrier, or enclosed within a carrier which can be in form of a capsule, sachet, paper or other container. In making the compositions, conventional techniques for the preparation of pharmaceutical compositions may be used. For example, the active compound will usually be mixed with a carrier, or diluted by a carrier, or enclosed within a carrier which may be in the form of a ampoule, capsule, sachet, paper, or other container. When the carrier serves as a diluent, it may be solid, semi-solid, or liquid material which acts as a vehicle, excipient, or medium for the active compound. The active compound can be adsorbed on a granular solid container for example in a sachet. Some examples of suitable carriers are water, salt solutions, alcohols, polyethylene glycols, polyhydroxyethoxylated castor oil, gelatine, lactose, amylose, magnesium stearate, talc, silicic acid, fatty acid monoglycerides and diglycerides, pentaerythritol fatty acid esters, hydroxymethylcellulose and polyvinylpyrrolidone. Similarly, the carrier or diluent may include any sustained release material known in the art, such as glyceryl monostearate or glyceryl distearate, alone or mixed with a wax. The formulations may also include wetting agents, emulsifying and suspending agents, preserving agents, sweetening agents or flavouring agents. The formulations of the invention may be formulated in any galenic dosage form so as to provide quick, sustained, or delayed release of the active ingredient after administration to the patient by employing procedures well known in the art. The pharmaceutical preparations can be sterilized and mixed, if desired, with auxiliary agents, emulsifiers, salt for influencing osmotic pressure, buffers and/or coloring substances and the like, which do not deleteriously react with the active compounds.

For administration, preferably nasal administration, the preparation may contain a compound of formula I, Ia, Ib or Ic dissolved or suspended in a liquid carrier, in particular an aqueous carrier, for aerosol application. The carrier may contain additives such as solubilizing agents, e.g. propylene glycol, surfactants, absorption enhancers such as lecithin (phosphatidylcholine) or cydodextrin, or preservatives such as parabenes. For parenteral application, particularly suitable are injectable solutions or suspensions, preferably aqueous solutions with the active compound dissolved in polyhydroxylated castor oil. Tablets, dragees, or capsules having talc and/or a carbohydrate carrier or binder or the like are particularly suitable for oral application. Preferable carriers for tablets, dragees, or capsules include lactose, com starch, and/or potato starch. A syrup or elixir can be used in cases where a sweetened vehicle can be employed.

A typical tablet, appropriate for use in this method, may be prepared by conventional tableting techniques and contains:

| Core: | |
|---|---|
| Active compound (as free compound or salt thereof) | 5.0 mg |
| Colloidal silicon dioxide (Aerosil) | 1.5 mg |
| Cellulose, microcryst. (Avicel) | 70 mg |
| Modified cellulose gum (Ac-Di-Sol) | 7.5 mg |
| Magnesium stearate | Ad. |
| Coating: | |
| HPMC approx. | 9 mg |
| *Mywacett 9-40 T approx. | 0.9 mg |

*Acylated monoglyceride used as plasticizer for film coating.

Due to their high degree of activity, the compounds of the invention may be administered to a mammal in need of such treatment, prevention, elimination, alleviation or amelioration of various diseases as mentioned above and especially of diseases of the endocrinological system such as hyperinsulinaemia and diabetes. Such mammals include both domestic animals, e.g. household pets, and non-domestic animals such as wildlife. Preferably the mammal is a human.

EXAMPLES

The process for preparing compounds of formula I, Ia, Ib, and/or Ic and preparations containing them is further illustrated in the following examples which, however, are not to be construed as limiting.

Example 1

Preparation of [4-(4-Trifluoromethylphenyl)-4,5,6,7-tetrahydro-thieno[3,2-c]pyridin-5-yl]-(4-methoxyphenyl)-methanone, (compound No. 5)

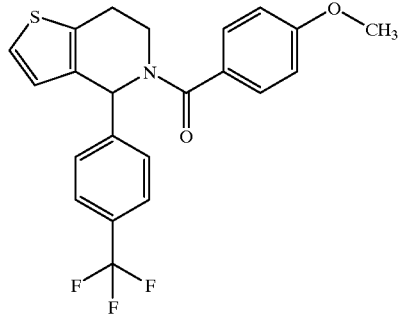

4-(4-Trifluoromethylphenyl)-4,5,6,7-tetrahydro-thieno[3,2-c]pyridine (100 mg, 0.35 mmol) was dissolved in dichloromethane (0.5 mL) and triethylamine (0.5 mL) was added. To this solution p-anisoyl chloride (60 mg, 0.35 mmol) dissolved in dichloromethane (0.5 ml) was added in one portion. The mixture was filtered and evaporated to afford 148 mg (100%) of the title compound.

MS (electrospray): m/z 418 (M+1)

HR-MS: Calculated for $C_{22}H_{18}F_3NO_2S$: 417.1010, Found: 417.0999.

Example 2

Preparation of [4-(4-Trifluoromethylphenyl)4,5,6,7-tetrahydro-thieno[3,2-c]pyridin-5-yl]-(3-methoxyphenyl)-methanone, (compound No. 8)

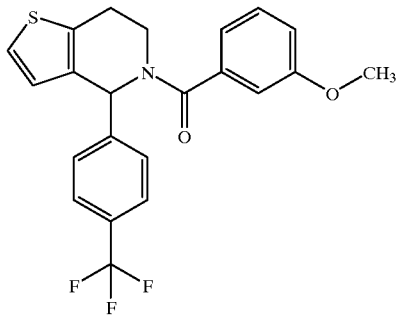

4-(4-Trifluoromethylphenyl)-4,5,6,7-tetrahydro-thieno[3,2-c]pyridine (100 mg, 0.35 mmol) was dissolved in dichloromethane (1 mL) and diisopropylethylamine (0.5 mL) was added. To this solution m-anisoyl chloride (50 μL, 0.35 mmol) was added. The mixture was shaken overnight and evaporated to afford the title compound.

MS (electrospray): m/z 418 (M+1)

HR-MS: Calculated for $C_{22}H_{18}F_3NO_2S$: 417.1010, Found: 417.1020.

Example 3

Preparation of [4-(4-Chlorophenyl)-4,5,6,7-tetrahydro-thieno[3,2-c]pyridin-5-yl]-phenyl-methanone, (compound No 11)

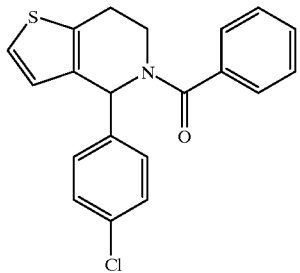

Benzoic acid (46 mg, 0.38 mmol) and 1-hydroxybenzotriazole (55 mg, 0.41 mmol) were dissolved in a mixture of dichloromethane (1 mL) and N,N-dimethylformamide (0.5 mL). N-(3-Dimethylaminopropyl)-N'-ethylcarbodiimide hydrochloride (79 mg, 0.41 mmol) was added and the mixture was shaken 0.5 hour at room temperature. 4-(4-Chlorophenyl)4,5,6,7-tetrahydro-thieno[3,2-c]pyridine (100 mg, 0.38 mmol) dissolved in dichloromethane (0.5 ml) was added and the mixture was shaken at 1000 rpm for 3 hours. Water (1 mL) was added and the mixture was shaken at 1000 rpm overnight at room temperature. The organic phase was evaporated to give 129 mg (97%) of the title compound as an oil.

MS (electrospray): m/z 354 (M+1)

HR-MS: Calculated for $C_{20}H_{16}ClNOS$: 353.0641, Found: 353.0646.

Example 4

Preparation of (4-(2-Dimethylaminoethoxy)phenyl)-[4-(4-trifluoromethylphenyl)-4,5,6,7-tetrahydro-thieno[3,2-c]pyridin-5-yl]-methanone, (compound No 14)

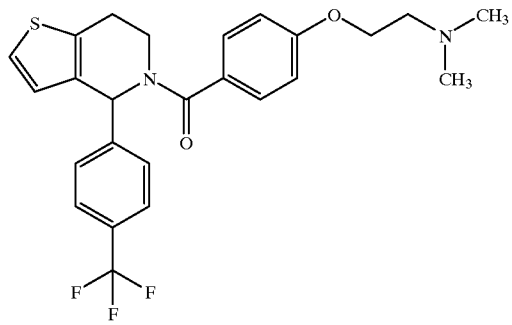

Methyl 4-hydroxybenzoate (10 g, 66 mmoles) was dissolved in N,N-dimethylformamide (200 mL). Potassium carbonate (45 g, 0.33 moles) and 2-chloro-N,N-dimethylethylamine hydrochloride (14.2 g, 99 mmoles) were added and the resulting mixture was stirred vigorously at room temperature for 7 days. More 2-chloro-N,N-dimethylethylamine hydrochloride (3 g, 20 mmoles) was added and stirring at room temperature was continued for 2 days. The reaction mixture was poured into water (600 mL) and extraction with ethyl acetate (2×200 mL), washing of the combined organic phases with water (200 mL), drying over $MgSO_4$ and evaporation afforded 11.9 g (81%) of methyl 4-(2-dimethylaminoethoxy)benzoate as an oil.

The above benzoate (11.9 g, 53 mmoles) was dissolved in 5 N hydrochloric acid and the mixture was heated at reflux temperature for 2 days. Cooling, filtration and washing with water afforded 8.63 g (66%) of 4-(2-dimethylaminoethoxy)benzoic acid hydrochloride as crystals.

The above benzoic acid (93 mg, 0.38 mmoles) was suspended in N,N-dimethylformamide (1 mL). 1-Hydroxybenzotriazole (55 mg, 0.42 mmoles), N-(3-dimethylaminopropyl)-N'-ethylcarbodiimide hydrochloride (79 mg, 0.42 mmoles), and triethylamine (106 μL, 0.76 mmoles) were added and the resulting mixture was shaken at 1000 rpm for 1.5 hour. 4-(4-Trifluoromethylphenyl)4,5,6,7-tetrahydro-thieno[3,2-c]pyridine (108 mg, 0.38 mmoles) were added and the resulting mixture was shaken at 1000 rpm for 3 hours. Water (2 mL) and ethyl acetate (1 mL) were added and the resulting mixture was shaken at 1000 rpm for 15 minutes. The organic phase was evaporated to afford 144 mg (80%) of the title compound as an oil.

MS (electrospray): m/z 475.0 (M+1)

HR-MS: Calculated for $C_{25}H_{25}F_3N_2O_2S$: 474.1588, Found: 474.1580.

Example 5

Preparation of [4-(4-Chlorophenyl)-4,5,6,7-tetrahydro-thieno[3,2-c]pyridin-5-yl]-[4-(2-morpholin-4ylethoxy)phenyl]-methanone, (compound No 17)

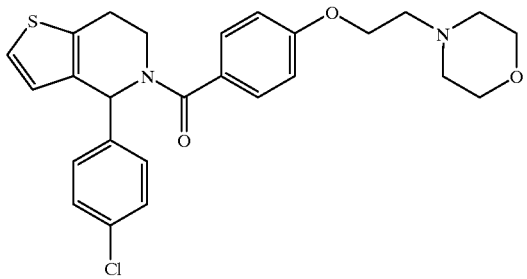

Methyl 4-hydroxybenzoate (10 g, 66 mmoles) was dissolved in N,N-dimethylformamide (200 mL). Potassium carbonate (45 g, 0.33 moles) and 4-(2-chloroethyl)morpholine hydrochloride (18.3 g, 99 mmoles) were added and the resulting mixture was stirred vigorously at room temperature for 5 days. The reaction mixture was poured into water (500 mL) and extraction with ethyl acetate (2×250 mL), washing of the combined organic phases with water (200 mL), drying over $MgSO_4$ and evaporation afforded 16.8 g (96%) of methyl 4-(2-morpholin-4-ylethoxy)benzoate as an oil.

The above benzoate (16.8 g, 63 mmoles) was dissolved in 5 N hydrochloric acid and the mixture was heated at reflux temperature for 16 hours. Cooling, filtration and washing with water afforded 15.6 g (86%) of 4-(2-morpholin-4-ylethoxy)benzoic acid hydrochloride as crystals.

The above benzoic acid (111 mg, 0.38 mmoles) was suspended in N,N-dimethylformamide (1 mL). 1-Hydroxybenzotriazole (55 mg, 0.42 mmoles), N-(3-dimethylaminopropyl)-N'-ethylcarbodiimide hydrochloride (79 mg, 0.42 mmoles), and triethylamine (106 μL, 0.76 mmoles) were added and the resulting mixture was shaken at 1000 rpm for 1.5 hour. 4-(4-Chlorophenyl)-4,5,6,7-tetrahydro-thieno[3,2-c]pyridine (100 mg, 0.38 mmoles) was added and the resulting mixture was shaken at 1000 rpm for 3 hours. Water (2 mL) and ethyl acetate (1 mL) were added and the resulting mixture was shaken at 1000 rpm for 15 minutes, The organic phase was evaporated to afford 122 mg (66%) of the title compound as an oil.

MS (electrospray): m/z 483.0 (M+1)

HR-MS: Calculated for $C_{26}H_{27}ClN_2O_3S$: 482.1431, Found: 482.1430.

Example 6

Preparation of (+)-[4-(4-Chlorophenyl)-4,5,6,7-tetrahydro-thieno[3,2-c]pyridin-5-yl]-(4-methoxyphenyl)-methanone, (compound No 1)

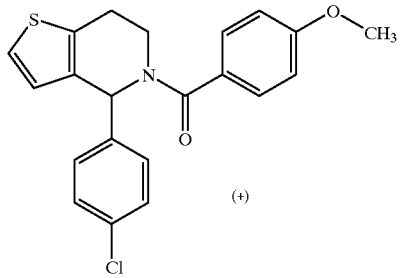

[4-(4-Chlorophenyl)-4,5,6,7-tetrahydro-thieno[3,2-c]pyridin-5-yl]-(4-methoxyphenyl)-methanone (30 mg) was dissolved in a 1:1 mixture of n-heptane and 2-propanol (5 mL) and fractionated by HPLC (2 runs) using a 21.1×250 mm (R,R)-Whelk-O column (Regis). The column was eluted isocratically with a 1:1 mixture of n-heptane and 2-propanol at a flow rate of 12 mL/min and fractions collected corresponding to 0.8 min/fraction. The eluting enantiomers were detected spectroscopically by measuring absorbance at a wavelength of 225 nm. Two eluting peaks were detected, one corresponding to $T_R$ 44–50 min and one corresponding to $T_R$ 62–72 min. Fractions from the two runs corresponding to $T_R$ 44–50 min were separately pooled and evaporated to yield 12.1 mg of the title compound.

100% ee (Determined by HPLC using a 4.6×250 mm (R,R)-Whelk-O column eluted with a 1:1 mixture of n-heptane and 2-propanol, the flow rate was 1 ml/min, eluting sample was monitored spectroscopically at 225 and 245 nm, $T_R$ 15.5 min).

Example 7

Preparation of (−)-[4-(4-Chlorophenyl)-4,5,6,7-tetrahydro-thieno[3,2-c]pyridin-5-yl]-(4-methoxyphenyl)-methanone, (compound No 2)

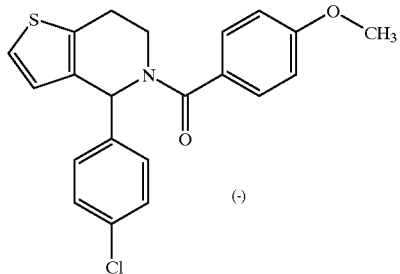

Fractions from the two runs of example 6 corresponding to $T_R$ 62–72 min were separately pooled and evaporated to yield 12.5 mg of the title compound 98% ee (Conditions as described in example 6, $T_R$ 20.8 min).

Optical rotation, using a Perkin Elmer Polarimeter (Model 241): $[\alpha]^{20}_D = -170.0$ (c=0.25, ethyl acetate).

Example 8

Preparation of (+)-[4-(4-Methoxyphenyl)-4,5,6,7-tetrahydro-thieno[3,2-c]pyridin-5-yl]-(4-trifluoromethylphenyl)-methanone, (compound No 3)

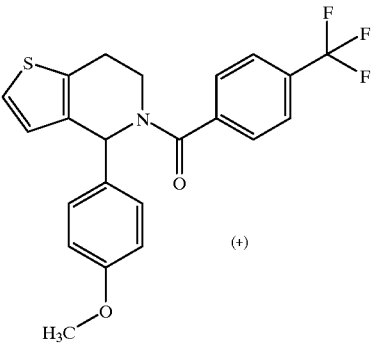

[4-(4-Methoxyphenyl)-4,5,6,7-tetrahydro-thieno[3,2-c]pyridin-5-yl]-(4-trifluoromethylphenyl)methanone (17 mg) was dissolved in a 1:2:2 mixture of ethyl acetate, n-heptane and 2-propanol (2.5 mL) and fractionated by HPLC using a 21.1×250 mm (R,R)-Whelk-O column (Regis). The column was eluted isocratically with a 1:1 mixture of n-heptane and 2-propanol at a flow rate of 10 mL/min and fractions collected corresponding to 1 min/fraction. The eluting enantiomers were detected spectroscopically by measuring absorbance at a wavelength of 225 nm. Two eluting peaks were detected, one corresponding to $T_R$ 27–32 min and one corresponding to $T_R$ 62–74 min. Fractions corresponding to $T_R$ 27–32 min were pooled and evaporated to yield 7.1 mg of the title compound.

100% ee (Determined by HPLC using a 4.6×250 mm (R,R)-Whelk-O column eluted with a 1:1 mixture of n-heptane and 2-propanol, the flow rate was 1 mumin, eluting sample was monitored spectroscopically at 225 and 245 nm, $T_R$ 9.2 min)

Optical rotation, using a Perkin Elmer Polarimeter (Model 241), $[\alpha]^{20}_D = +175.4$ (c=0.142, ethyl acetate).

Example 9

Preparation of (−)-[4-(4-Methoxyphenyl)-4,5,6,7-tetrahydro-thieno[3,2-c]pyridin-5-yl]-(4-trifluoromethylphenyl)-methanone, (compound No 4)

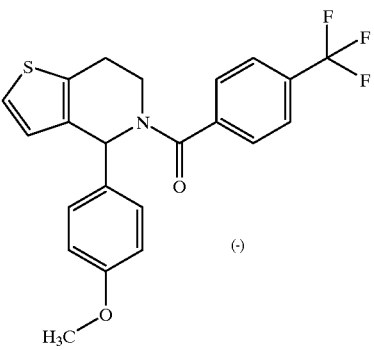

Fractions from the two runs of example 8 corresponding to $T_R$ 62–74 min were separately pooled and evaporated to yield 6.8 mg of the title compound.

>99.5% ee (Conditions as described in example 8, $T_R$ 17.0 min).

$[\alpha]^{20}_D = -170.6$ (c=0.136, ethyl acetate).

Example 10

[4-(4-Trifluoromethylphenyl)-4,5,6,7-tetrahydro-thieno[3,2-c]pyridin-5-yl]-(4-dimethylaminophenyl)-methanone, (compound No 20)

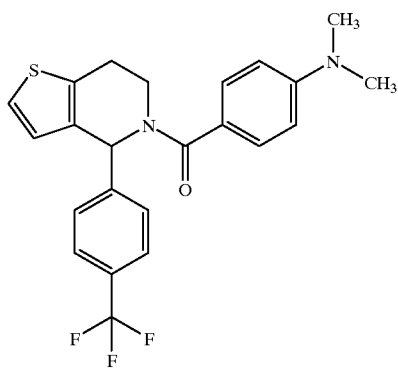

4-Dimethylaminobenzoic acid (0.20 g, 1.2 mmol) was dissolved in N,N-dimethylformamide (3 ml) and 1-hydroxybenzotriazole (0.20 g, 1.5 mmol) was added. To the resulting mixture N-(3-dimethylaminopropyl)-N'-ethylcarbodiimide hydrochloride (0.28 g, 1.5 mmol) was added and the mixture was stirred at room temperature for 15 minutes. 4-(4-Trifluoromethylphenyl)-4,5,6,7-tetrahydro-thieno[3,2-c]pyridine (0.41 g, 1.5 mmol) followed by diisopropylethylamine (0.42 ml, 2.4 mmol) were added and the mixture was stirred at room temperature for 16 hours. water (2 ml) was added and the mixture was extracted with ethyl acetate (2×5 ml). The combined organic extracts were washed with saturated aqueous sodium chloride solution (4 ml), dried (MgSO$_4$) and concentrated in vacuo to afford the title compound.

MS (electrospray): m/z 431 (M+1)

HPLC (Method B): $R_t$=29 min.

Example 11

3-{4-[4-(4-Chlorophenyl)-4,5,6,7-tetrahydro-thieno[3,2-c]pyridine-5-carbonyl]phenyl}acrylic acid, (compound No 21)

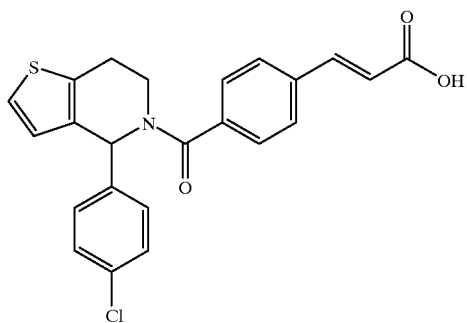

(E)-4-(2-tert-Butoxycarbonylvinyl)benzoic acid (0.36 g, 1.4 mmol) was dissolved in N,N-dimethylformamide (50 ml) and 1-hydroxybenzoetriazole (0.20 g, 1.4 mmol) and N-(3-dimethylaminopropyl)-N'-ethylcarbodiimide hydrochloride (0.28 g, 1.4 mmol) were added and the mixture was stirred at room temperature for 20 minutes. 4-(4-Chlorophenyl)-4,5,6,7-tetrahydro-thieno[3,2-c]pyridine (0.30 g, 1.2 mmol) and N-ethyl-N,N-diisopropylamine (420 μl, 2.4 mmol) were added to the mixture and stirring at room temperature was continued for 16 hours. The mixture was diluted with water (50 ml) and extracted with ethyl acetate (3×50 ml). The combined organic extracts were washed with saturated sodium chloride (80 ml), dried over MgSO$_4$ and concentrated in vacuo. The residue was purified by column chromatography over silica gel (60 ml) eluting with a mixture of ethyl acetate and heptane (1:2), This afforded 0.56 g (97%) of 3-{4-[4-(4-Chlorophenyl)-4,5,6,7-tetrahydro-thieno[3,2-c]pyridine-5-carbonyl]phenyl}acrylic acid tert butyl ester as an oil.

$^1$H-NMR (300 MHz, DMSO-d$_6$): δ=1.50 (9H, s), 2.8–3.1 (2H, m), 3.25 (1H, m), 3.65 (1H, m), 6.58 !1H, d), 6.78 (1H, bs), 6.87 (1H, d), 7.3–7.45 (7H, m), 7.60 (1H, d), 7.77 (2H, d).

The above tert-butyl ester (0.30 9, 0.62 mmol) was dissolved in dichloromethane (3 ml) and the mixture was cooled to 0° C. At 0° C. trifluoroacetic acid (3 ml) was added and the mixtures was stirred at 0° C. for 30 minutes. The mixture was concentrated in vacuo. The residue was dissolved in dichloromethane (5 ml), concentrated in vacuo dissolved again in methanol (5 ml) and concentrated in vacuo. 10.6 mg of the residue was dissolved in 750 μl methanol and purified by preparative HPLC using a Gilson binary gradient HPLC system equipped with 305/306 master/slave pumps, 117 UV detector and fraction collector. The eluting sample was detected at 210 and 225 nm. Flow rate was 15 ml/minute. The column was 20*250 mm ODS 10 μm (YMC) eluted with a gradient of acetonitrile (solvent B) and de-ionised water added 0.05% TFA (solvent A), 45%B to 100% B over 30 minutes. Fractions corresponding to $T_R$ 12–14 minutes were pooled to yield 8.3 mg of the title compound.

MS: m/z 424 (M+1).

Example 12

(4-Chlorophenyl)-[4-(4-chlorophenyl)-4,5,6,7-tetrahydro-thieno[3,2-c]pyridin-5-yl]-methanone, (compound No 22), Less Polar Enantiomer

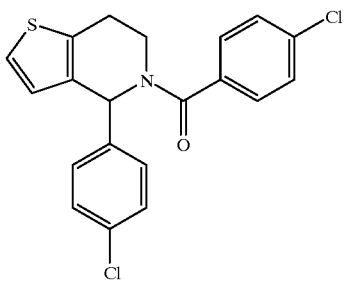

(4-Chlorophenyl)-[4-(4-chlorophenyl)-4,5,6,7-tetrahydro-thieno[3,2-cl pyridin-5-yl]-methanone (4.1 mg) was dissolved in a 1:2:4 mixture of ethyl acetate, heptane and 2-propanol (3.5 ml) and fractionated by HPLC using a 21.1×250 mm (R,R)-Whelk-0 column (Regis). The column was eluted isocratically with a 1:1 mixture of heptane and 2-propanol at a flow rate of 10 ml/min and fractions collected corresponding to 1 min/fraction. The eluting enantiomers were detected spectroscopically by measuring absorbance at a wavelength of 225 nm. Two eluting peaks were detected, one corresponding to $T_R$ 28–32 minutes and one corresponding to $T_R$ 51–58 minutes. Fractions corresponding $T_R$ 28–32 minutes were pooled and evaporated to yield 1.8 mg of the title compound.

100% ee (Determined by HPLC using a 4.6×250 mm (R,R)-Whelk-0 column eluted with n-heptane:2-propanol (1:1), the flow rate was 1 ml/min, eluting sample was monitored spectroscopically at 225 nm, $T_R$ 9.9 min)

Example 13

(4-Chlorophenyl)-[4-(4-chlorophenyl)-4,5,6,7-tetrahydro-thieno[3,2-c]pyridin-5-yl]-methanone, (compound No 23), More Polar Enantiomer

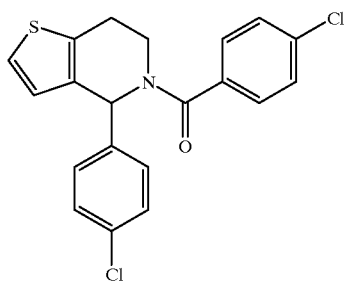

Fractions from example 12 corresponding to $T_R$ 51–58 minutes were pooled and evaporated to yield 2.6 mg of the title compound.

99.5% ee (Conditions as described in example 12, $T_R$ 15.5 min).

Example 14

[4-(4-Trifluoromethylphenyl)-4,5,6,7-tetrahydro-thieno[3,2-c]pyridin-5-yl]-(4-methoxyphenyl)-methanone, (compound No. 24), Less Polar Enantiomer

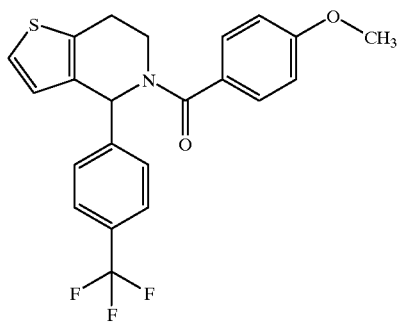

4-(4-Trifluoromethylphenyl)-4,5,6,7-tetrahydro-thieno[3,2-c]pyridin-5-yl]-(4-methoxyphenyl)-methanone (11.2 mg) was dissolved in a 1:1 mixture of heptane and 2-propanol (2 ml) and fractionated by HPLC using a 21.1×250 mm (R,R)-Whelk-O column (Regis). The column was eluted isocratically with a 1:1 mixture of heptane and 2-propanol at a flow rate of 10 ml/min and fractions collected corresponding to 1 minute/fraction. The eluting enantiomers were detected spectroscopically by measuring absorbance at a wavelength of 225 nm. Two eluting peaks were detected, one corresponding to $T_R$ 40–43 minutes and one corresponding to $T_R$ 55–59 minutes. Fractions corresponding to $T_R$ 40–43 minutes were pooled and evaporated to yield 4.0 mg of the title compound.

>99% ee (Determined by HPLC using a 4.6×250 mm (R,R)-Whelk-O column eluted with a 1:1 mixture of heptane and 2-propanol, the flow rate was 1 ml/min, eluting sample was monitored spectroscopically at 225 and 245 nm, $T_R$ 12.6 min).

Example 15

[4-(4-Trifluoromethylphenyl)-4,5,6,7-tetrahydro-thieno[3,2-c]pyridin-5-yl]-(4-methoxyphenyl)-methanone, (compound No. 25), More Polar Enantiomer

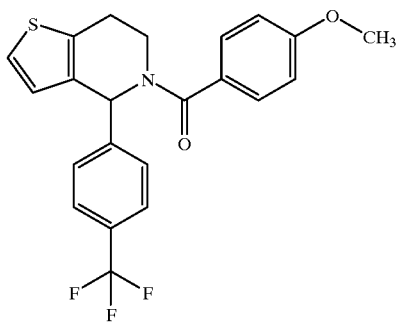

Fractions from example 14 corresponding to $T_R$ 55–59 minutes were pooled and evaporated to yield 4.0 mg of the title compound.

99% ee (Conditions as described in example 14, $T_R$ 16.4 min).

Example 16

[4-(2-Dimethylaminoethoxy)-phenyl]-[4-(4-trifluoromethylphenyl)-4,5,6,7-tetrahydro-thieno[3,2-c]pyridin-5-yl]-methanone, (compound No. 26), Less Polar Enantiomer

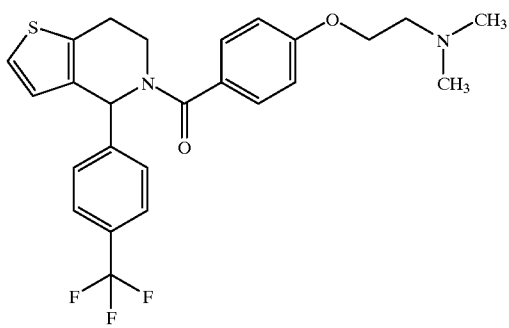

[4-(2-Dimethylaminoethoxy)-phenyl]-[4-(4-trifluoromethylphenyl)-4,5,6,7-tetrahydro-thieno[3,2-c]pyridin-5-yl]-methanone (ca. 20 mg) was dissolved in a 1:1 mixture of heptane and 2-propanol (1 ml) and fractionated by HPLC using a 20×250 mm Chiralcel OD column. The column was eluted isocratically with a 7:3:0.01 mixture of heptane, 2-propanol and diethylamine at a flow rate of 6 ml/min and fractions collected corresponding to 1 min/fraction. The eluting enantiomers were detected spectroscopically by measuring absorbance at a wavelength of 225 nm. Two eluting peaks were detected, one corresponding to $T_R$ 20–25 minutes and one corresponding to $T_R$ 27–33 minutes. Fractions corresponding to $T_R$ 20–25 minutes were pooled and evaporated to yield 8.4 mg of the title compound.

>99.9% ee (Determined by HPLC using a 4.6×250 mm Chiralcel OD column eluted with a 70:30:0.07 mixture of heptane, 2-propanol and diethylamine, the flow rate was 0.4 ml/min, eluting sample was monitored spectroscopically at 225 and 245 nm, $T_R$ 15.4 min).

Example 17

[4-(2-Dimethylaminoethoxy)-phenyl]-[4-(4-trifluoromethylphenyl)4,5,6,7-tetrahydro-thieno[3,2-c]pyridin-5-yl]-methanone, (compound No. 27), More Polar Enantiomer

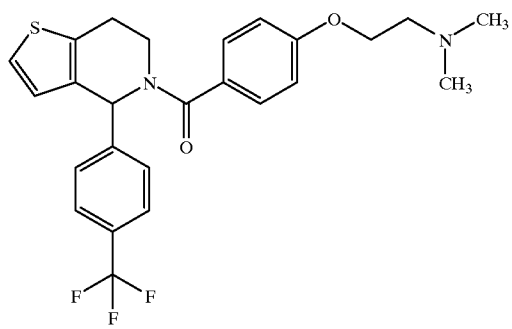

Fractions from example 16 corresponding to $T_R$ 27–33 minutes were pooled and evaporated to yield 8.9 mg of the title compound.

>99% ee (Conditions as described in example 16, $T_R$ 20.1 min).

Example 18

[4-(4-Chlorophenyl)-4,5,6,7-tetrahydro-thieno[3,2-c]pyridin-5-yl]-[4-(2-morpholin-4-ylethoxy)phenyl]-methanone, (compound No. 28), Less Polar Enantiomer

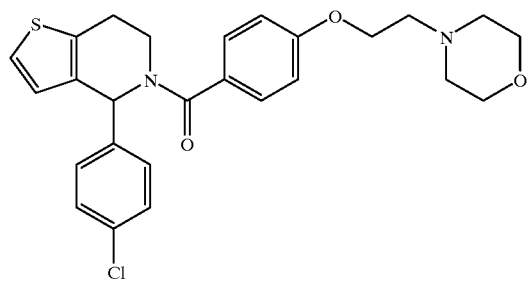

[4-(4-Chlorophenyl)-4,5,6,7-tetrahydro-thieno[3,2-c]pyridin-5-yl]-[4-(2-morpholin-4-ylethoxy)phenyl]-methanone (ca. 10 mg) was dissolved in 3 ml a 15:15:1:0.2 mixture of heptane, 2-propanol, ethyl acetate and diethylamine (3 ml) and fractionated by HPLC using a 20×250 mm Chiralcel OD column. The column was eluted isocratically with a 70:30:0.1 mixture of heptane, 2-propanol and diethylamine at a flow rate of 6 ml/min and fractions collected corresponding to 1 minute/fraction. The eluting enantiomers were detected spectroscopically by measuring absorbance at a wavelength of 225 nm. Two eluting peaks were detected, one corresponding to $T_R$ 40–47 minutes and one corresponding to $T_R$ 50–59 minutes. Fractions corresponding to $T_R$ 40–47 minutes were pooled and evaporated to yield 4.1 mg of the title compound.

>99.9% ee (Determined by HPLC using a 4.6×250 mm Chiralcel OD column eluted with a 70:30:0.07 mixture of heptane, 2-propanol and diethylamine, the flow rate was 0.4 m/min, eluting sample was monitored spectroscopically at 225 nm, $T_R$ 22.9 min).

Example 19

[4-(4-Chlorophenyl)-4,5,6,7-tetrahydro-thieno[3,2-c]pyridin-5-yl]-[4-(2-morpholin-4-ylethoxy)phenyl]-methanone, (compound No. 29), More Polar Enantiomer

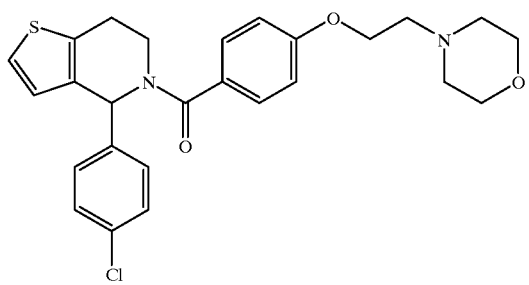

Fractions from example 18 corresponding to $T_R$ 50–59 minutes were pooled and evaporated to yield 4.0 mg of the title compound.

98% ee (Conditions as described in example 18, $T_R$ 28.5 min).

Example 20

[4-(4-Trifluoromethoxyphenyl)-4,5,6,7-tetrahydro-thieno[3,2-c]pyridin-5-yl]-(4-methoxyphenyl)-methanone, (compound No. 30), Less Polar Enantiomer

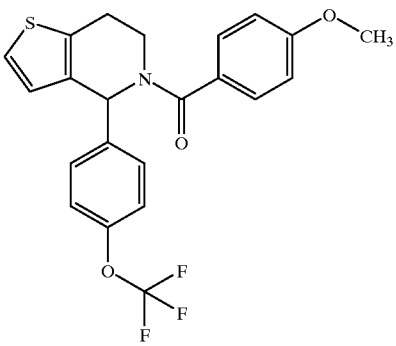

[4-(4-Trifluoromethoxyphenyl)-4,5,6,7-tetrahydro-thieno[3,2-c]pyridin-5-yl]-(4-methoxy-phenyl)-methanone (10 mg) was dissolved in 2-propanol (0.5 ml) and fractionated by HPLC using a 21.1×250 mm (R,R)-Whelk-O column (Regis). The column was eluted isocratically with a 1:1 mixture of heptane and 2-propanol at a flow rate of 10 ml/min and fractions collected corresponding to 1 minute/ fraction. The eluting enantiomers were detected spectroscopically by measuring absorbance at a wavelength of 225 nm. Two eluting peaks were detected, one corresponding to $T_R$ 24–30 minutes and one corresponding to $T_R$ 41–47 minutes. Fractions corresponding to $T_R$ 24–30 minutes were pooled and evaporated to yield 2.5 mg of the title compound.

>99.8% ee (Determined by HPLC using a 4.6×250 mm (R,R)-Whelk-O column eluted with a 1:1 mixture of n-heptane and 2-propanol, the flow rate was 1 ml/minute, eluting sample was monitored spectroscopically at 225 and 254 nm, $T_R$ 12.0 min)

Example 21

[4-(4-Trifluoromethoxyphenyl)-4,5,6,7-tetrahydro-thieno[3,2-c]pyridin-5-yl]-(4-methoxyphenyl)-methanone, (compound No. 31), More Polar Enantiomer

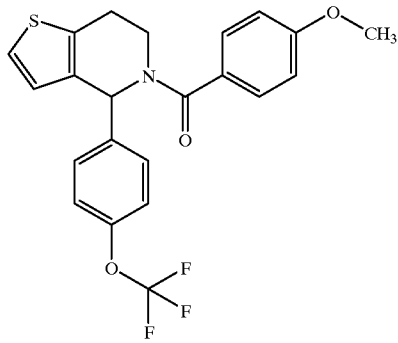

Fractions from example 20 corresponding to $T_R$ 41–47 minutes were pooled and evaporated to yield 2.3 mg of the title compound.

99.1% ee (Conditions as described in example 20, $T_R$ 15.8 min).

The compounds of this invention can also be prepared by parallel syntheses, for example by a method essentially as described above, e.g. as described in example 3. The 1-hydroxybenzotriazole or another hydroxy azole known to be effective as alcohol component in active ester mediated amide coupling reactions can either be present in the reaction or it can be omitted depending on the substitution on the carboxylic acid part. This will be recognised by those skilled in the art.

A general procedure for parallel preparation of compounds of the invention is given in example 22:

Example 22

[4-(4-Trifluoromethoxyphenyl)-4,5,6,7-tetrahydro-thieno[3,2-c]pyridin-5-yl]-(4-methoxyphenyl)-methanone, (compound No. 32)

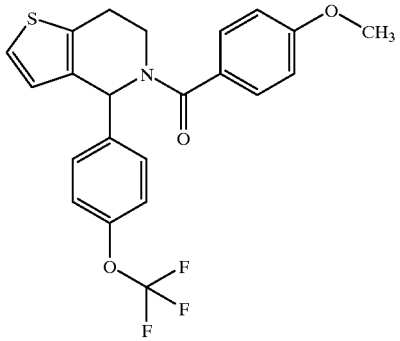

A solution of 4-(4-Trifluoromethoxyphenyl)4,5,6,7-tetrahydro-thieno[3,2-c]pyridine in N,N-dimethylformamide (0.375 M, 0.4 ml, 0.15 mmol) was added to a solution of 4-methoxybenzoic acid in N,N-dimethylformamide (0.375 M, 0.4 ml, 0.15 mmol). To this solution 0.25 ml of a suspension of N-(3-dimethylaminopropyl)-N'-ethylcarbodiimide hydrochloride in dichloromethane (1.73 g in 8.3 ml) was added. The mixture was shaken overnight at room temperature at 1000 rpm, added saturated NaCl (2 ml), and extracted with ethyl acetate (2×1 ml). The combined organic extracts were evaporated to afford the title compound.

MS (electrospray): m/z 434 (M+1)

HPLC (Method B): $R_t$=33.2 min.

Example 23

[4-(4-Chlorophenyl)4,5,6,7-tetrahydro-thieno[3,2-c]pyridin-5-yl]-(1 H-indol-5-yl)-methanone, (compound No. 33)

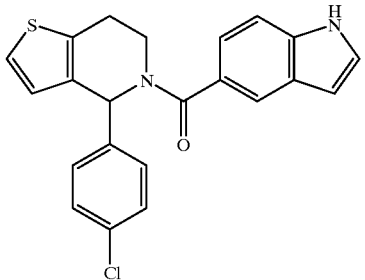

Similarly as described in example 22 using a solution of 4-(4-chlorophenyl)-4,5,6,7-tetrahydro-thieno[3,2-c]pyridine in N,N-dimethylformamide (0.375 M, 0.4 ml, 0.15 mmol), a solution of indole-5-carboxylic acid in N,N-dimethylformamide (0.375 M, 0.4 ml, 0.15 mmol) and 0.25 ml of a suspension of N-(3-dimethylaminopropyl)-N'-ethylcarbodiimide hydrochloride in dichloromethane (1.73 g in 8.3 ml) affords the title compound.

MS (electrospray): m/z 393 (M+1)

HPLC (Method B): $R_t$=30.7 min.

Example 24

(1H-Indol-5-yl)-[4-(4-trifluoromethoxyphenyl)-4,5,6,7-tetrahydro-thieno[3,2-c]pyridin-5-yl]-methanone, (compound No. 34)

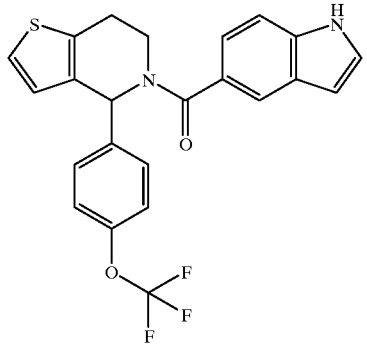

Similarly as described in example 22 using a solution of 4-(4-Trifluoromethoxyphenyl)-4,5,6,7-tetrahydro-thieno[3,2-c]pyridine in N,N-dimethylformamide (0.375 M, 0.4 ml, 0.15 mmol), a solution of indole-5-carboxylic acid in N,N-dimethylformamide (0.375 M, 0.4 ml, 0.15 mmol) and 0.25 ml of a suspension of N-(3-dimethylaminopropyl)-N'-ethylcarbodiimide hydrochloride in dichloromethane (1.73 g in 8.3 ml) affords the title compound.

MS (electrospray): m/z 443 (M+1)

HPLC (Method B): $R_t$=31.5 min.

Example 25

[4-(4-Chlorophenyl)-4,5,6,7-tetrahydro-thieno[3,2-c]pyridin-5-yl]-(4-fluorophenyl)-methanone, (compound No. 35)

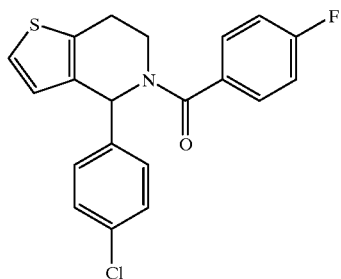

Similarly as described in example 22 using a solution of 4-(4-chlorophenyl)-4,5,6,7-tetrahydro-thieno[3,2-c]pyridine in N,N-dimethylformamide (0.375 M, 0.4 ml, 0.15 mmol), a solution of 4-fluorobenzoic acid in N,N-dimethylformamide (0.375 M, 0.4 ml, 0.15 mmol) and 0.25 ml of a suspension of N-(3-dimethylaminopropyl)-N'-ethylcarbodiimide hydrochloride in dichloromethane (1.73 g in 8.3 ml) affords the title compound.

MS (electrospray): m/z 372 (M+1)

HPLC (Method B): $R_t$=32.6 min.

Example 26

[4-(4-Trifluoromethoxyphenyl)-4,5,6,7-tetrahydro-thieno[3,2-c]pyridin-5-yl]-(4-fluorophenyl)-methanone, (compound No. 36)

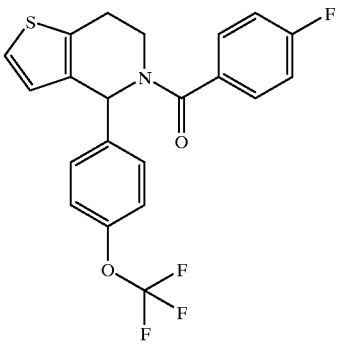

Similarly as described in example 22 using a solution of 4-(4-trifluoromethoxyphenyl)-4,5,6,7-tetrahydro-thieno[3,2-c]pyridine in N,N-dimethylformamide (0.375 M, 0.4 ml, 0.15 mmol), a solution of 4-fluorobenzoic acid in N,N-dimethylformamide (0.375 M, 0.4 ml, 0.15 mmol) and 0.25 ml of a suspension of N-(3-dimethylaminopropyl)-N'-ethylcarbodiimide hydrochloride in dichloromethane (1.73 g in 8.3 ml) affords the title compound.

MS (electrospray): m/z 422 (M+1)

HPLC (Method B): $R_t$=32.2 min.

Example 27

[4-(4-Chlorophenyl)4,5,6,7-tetrahydro-thieno[3,2-c]pyridin-5-yl]-[4-(2-dimethylaminoethoxy)phenyl]-methanone, (compound No. 37)

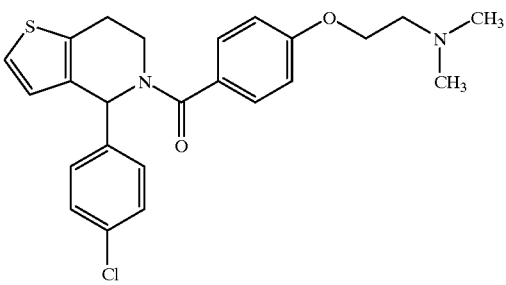

Similarly as described in example 22 using a solution of 4-(4-chlorophenyl)-4,5,6,7-tetrahydro-thieno[3,2-c]pyridine in N,N-dimethylformamide (0.375 M, 0.4 ml, 0.15 mmol), a suspension of 4-(2-dimethylaminoethoxy)benzoic acid hydrochloride in N,N-dimethylformamide (0.375 M, 0.4 ml, 0.15 mmol), triethylamine (42 ul), and 0.25 ml of a suspension of N-(3-dimethylaminopropyl)-N'-ethylcarbodiimide hydrochloride in dichloromethane (1.73 g in 8.3 ml) affords the title compound.

MS (electrospray): m/z 441 (M+1)

HPLC (Method B): $R_t$=23.4 min.

Example 28

[4-(2-Dimethylaminoethoxy)phenyl]-[4-(4-trifluoromethoxyphenyl)-4,5,6,7-tetrahydro-thieno[3,2-c]pyridin-5-yl]-methanone, (compound No. 38)

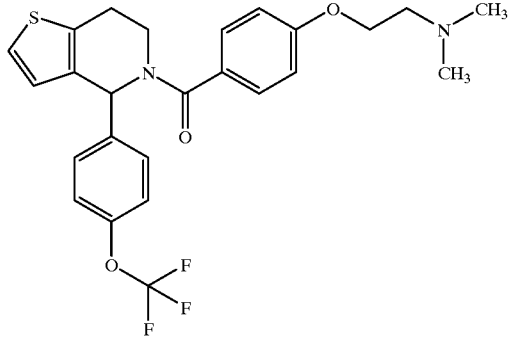

Similarly as described in example 22 using a solution of 4-(4-trifluoromethoxyphenyl)-4,5,6,7-tetrahydro-thieno[3,2-c]pyridine in N,N-dimethylformamide (0.375 M, 0.4 ml, 0.15 mmol), a suspension of 4-(2-dimethylaminoethoxy) benzoic acid hydrochloride in N,N-dimethylformamide (0.375 M, 0.4 ml, 0.15 mmol), triethylamine (42 pi), and 0.25 ml of a suspension of N-(3-dimethylaminopropyl)-N'-ethylcarbodiimide hydrochloride in dichloromethane (1.73 g in 8.3 ml) affords the title compound.

MS (electrospray): m/z 491 (M+1)

HPLC (Method B): $R_t$=24.9 min.

Example 29

[7-Chloro-1-(2,3-dihydrobenzofuran-7-yl)-8-methoxy-1,2,4,5-tetrahydrobenzo[d]azepin-3-yl]-[4-(2-dimethylaminoethoxy)-phenyl]-methanone, (compound No. 39)

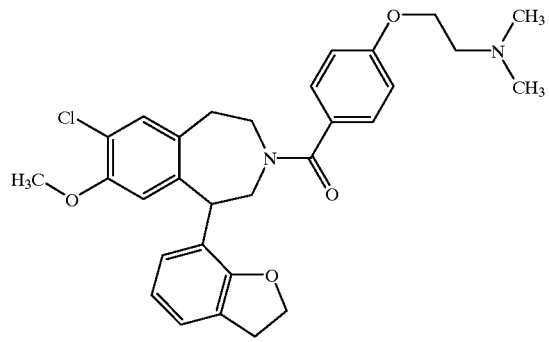

Similarly as described in example 22 using a solution of 7-chloro-1-(2,3-dihydrobenzofuran-7-yl)-8-methoxy-1,2,4,5-tetrahydrobenzo[d]azepine in N,N-dimethylformamide (0.375 M, 0.4 ml, 0.15 mmol), a suspension of 4-(2-dimethylaminoethoxy)benzoic acid hydrochloride in N,N-dimethylformamide (0.375 M, 0.4 ml, 0.15 mmol), triethylamine (42 pi), and 0.25 ml of a suspension of N-(3-dimethylaminopropyl)-N'-ethylcarbodiimide hydrochloride in dichloromethane (1.73 g in 8.3 ml) affords the title compound.

MS (electrospray): m/z 521 (M+1)

HPLC (Method B): $R_t$=22.9 min.

Example 30

[4-(3,4-Dimethoxyphenyl)-4,5,6,7-tetrahydro-thieno[2,3-c]pyridin-6-yl]-[4-(2-dimethylaminoethoxy)-phenyl]-methanone, (compound No. 40)

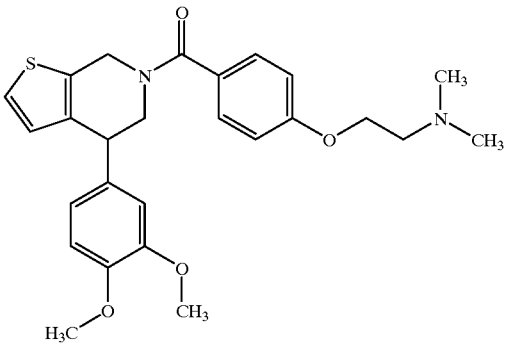

Similarly as described in example 22 using a solution of 4-(3,4-Dimethoxyphenyl)-4,5,6,7-tetrahydro-thieno[2,3-c] pyridine in N,N-dimethylformamide (0.375 M, 0.4 ml, 0.15 mmol), a suspension of 4-(2-dimethylaminoethoxy)benzoic acid hydrochloride in N,N-dimethylformamide (0.375 M, 0.4 ml, 0.15 mmol), triethylamine (42 pi), and 0.25 ml of a suspension of N-(3-dimethylaminopropyl)-N'-ethylcarbodiimide hydrochloride in dichloromethane (1.73 9 in 8.3 ml) affords the title compound.

MS (electrospray): m/z 467 (M+1)

HPLC (Method B): $R_t$=18.1 min.

Example 31

(3,4-Dimethoxyphenyl)-[4-(4-trifluoromethoxyphenyl)-4,5,6,7-tetrahydro-thieno[3,2-c]pyridin-5-yl]methanone, (compound No. 41)

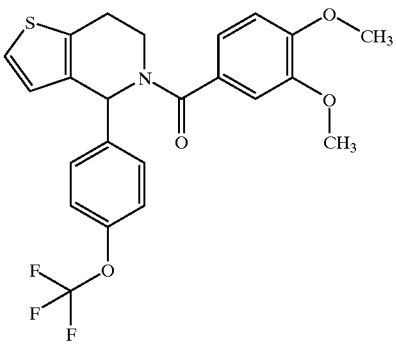

Similarly as described in example 22 using a solution of 4-(4-trifluoromethoxyphenyl)-4,5,6,7-tetrahydro-thieno[3,2-c]pyridine in N,N-dimethylformamide (0.375 M, 0.4 ml, 0.15 mmol), a solution of 3,4-dimethoxybenzoic acid in N,N-dimethylformamide (0.375 M, 0.4 ml, 0.15 mmol), and 0.25 ml of a suspension of N-(3-dimethylaminopropyl)-N'-ethylcarbodiimide hydrochloride in dichloromethane (1.73 g in 8.3 ml) affords the title compound.

MS (electrospray): m/z 464 (M+1)

HPLC (Method B): $R_t$=32.1 min

Example 32

(3-chloro-4-methoxyphenyl)-[4-(4-trifluoromethoxyphenyl)-4,5,6,7-tetrahydro-thieno[3,2-c]pyridin-5-yl]methanone, (compound No. 42)

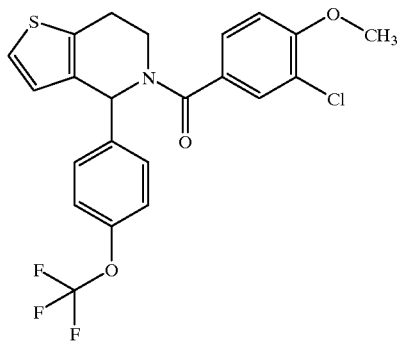

Similarly as described in example 22 using a solution of 4-(4-trifluoromethoxyphenyl)-4,5,6,7-tetrahydro-thieno[3,2-c]pyridine in N,N-dimethylformamide (0.375 M, 0.4 ml, 0.15 mmol), a solution of 3-chloro-4-methoxybenzoic acid in N,N-dimethylformamide (0.375 M, 0.4 ml, 0.15 mmol), and 0.25 ml of a suspension of N-(3-dimethylaminopropyl)-N'-ethylcarbodiimide hydrochloride in dichloromethane (1.73 g in 8.3 ml) affords the title compound.

MS (electrospray): m/z 468 (M+1)

HPLC (Method B): $R_t$=34.4 min

Example 33

(4-Ethoxyphenyl)-[4-(4-trifluoromethoxyphenyl)-4,5,6,7-tetrahydro-thieno[3,2-c]pyridin-5-yl]methanone, (compound No. 43)

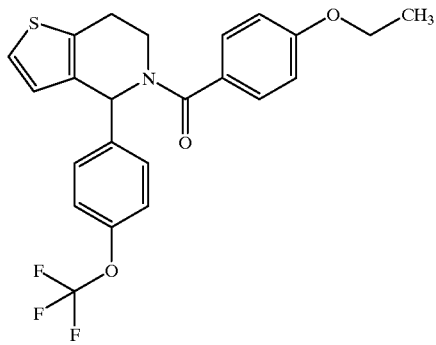

Similarly as described in example 22 using a solution of 4-(4-trifluoromethoxyphenyl)-4,5,6,7-tetrahydro-thieno[3,2-c]pyridine in N,N-dimethylformamide (0.375 M, 0.4 ml, 0.15 mmol), a solution of 4-ethoxybenzoic acid in N,N-dimethylformamide (0.375 M, 0.4 ml, 0.15 mmol), and 0.25 ml of a suspension of N-(3-dimethylaminopropyl)-N'-ethylcarbodiimide hydrochloride in dichloromethane (1.73 g in 8.3 ml) affords the title compound.

MS (electrospray): m/z 448 (M+1)

HPLC (Method B): $R_t$=35.1 min

Example 34

(4-Methylphenyl)-[4-(4-trifluoromethoxyphenyl)-4,5,6,7-tetrahydro-thieno[3,2-c]pyridin-5-yl]methanone, (compound No. 44)

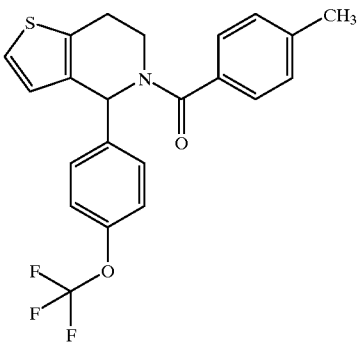

Similarly as described in example 22 using a solution of 4-(4-trifluoromethoxyphenyl)-4,5,6,7-tetrahydro-thieno[3,2-c]pyridine in N,N-dimethylformamide (0.375 M, 0.4 ml, 0.15 mmol), a solution of 4-methylbenzoic acid in N,N-dimethylformamide (0.375 M, 0.4 ml, 0.15 mmol), and 0.25 ml of a suspension of N-(3-dimethylaminopropyl)-N'-ethylcarbodiimide hydrochloride in dichloromethane (1.73 g in 8.3 ml) affords the title compound.

MS (electrospray): m/z 418 (M+1)

HPLC (Method B): $R_t$=35.2 min

Example 35

3-(4-Methoxyphenyl)-1-[4-(4-trifluoromethoxyphenyl)-4,5,6,7-tetrahydro-thieno[3,2-c]pyridin-5-yl]propenone, (compound No. 45)

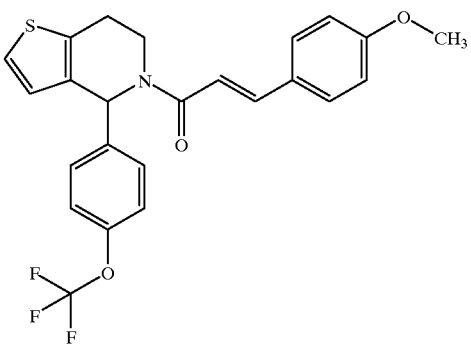

Similarly as described in example 22 using a solution of 4-(4-trifluoromethoxy-phenyl)-4,5,6,7-tetrahydro-thieno[3,2-c]pyridine in N,N-dimethylformamide (0.375 M, 0.4 ml, 0.15 mmol), a solution of 4-methoxycinnamic acid in N,N-dimethylformamide (0.375 M, 0.4 ml, 0.15 mmol), and 0.25 ml of a suspension of N-(3-dimethylaminopropyl)-N'-ethylcarbodiimide hydrochloride in dichloromethane (1.73 g in 8.3 ml) affords the title compound.

MS (electrospray): m/z 460 (M+1)

HPLC (Method B): $R_t$=35.0 min

Example 36

(1H-Benzimidazol-5-yl)-[4-(4-trifluoromethoxyphenyl)-4,5,6,7-tetrahydro-thieno[3,2-c]pyridin-5-yl]methanone, (compound No. 46)

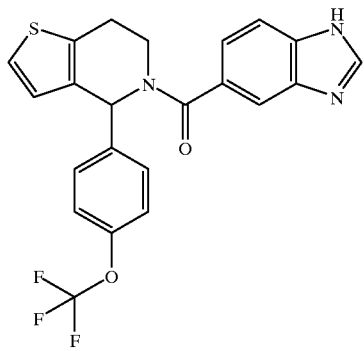

Similarly as described in example 22 using a solution of 4-(4-trifluoromethoxyphenyl)-4,5,6,7-tetrahydro-thieno[3,2-c]pyridine in N,N-dimethylformamide (0.375 M, 0.4 ml, 0.15 mmol), a solution of benzimidazole-5-carboxylic acid in N,N-dimethylformamide (0.375 M, 0.4 ml, 0.15 mmol), and 0.25 ml of a suspension of N-(3-dimethylaminopropyl)-N'-ethylcarbodiimide hydrochloride in dichloromethane (1.73 g in 8.3 ml) affords the title compound.

MS (electrospray): m/z 444 (M+1)
HPLC (Method B): $R_t$=23.1 min

Example 37

(4-Methoxyphenyl)-[4-(4-trifluoromethoxyphenyl)-4,5,6,7-tetrahydro-thieno[3,2-c]pyridin-5-yl]-methanone

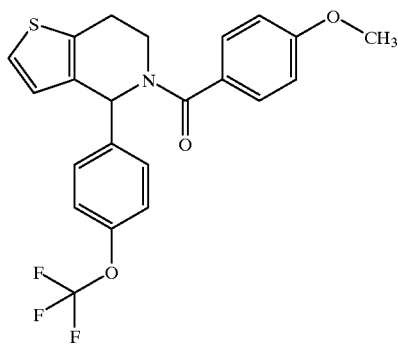

4-Methoxybenzoic acid (0.64 g, 4.2 mmol) was dissolved in N,N-dimethylformamide (25 ml) and 1-hydroxybenzotriazole (0.71 g, 5 mmol) was added followed by N-(3-dimethylaminopropyl)-N'-ethylcarbodiimide hydrochloride (0.96 g, 5 mmol). The resulting mixture was stirred at room temperature for 30 minutes. 4-(4-Trifluoromethoxyphenyl)-4,5,6,7-tetrahydro-thieno[3,2-c]pyridine (1.5 g, 5 mmol) followed by N,N-diisopropylethylamine (1.4 ml, 8.4 mmol) were added and the resulting mixture was stirred at room temperature for 16 hours. Water (10 ml) was added and the mixture was extracted with diethyl ether (3×20 ml). The combined organic extracts were washed with saturated aqueous ammonium chloride (20 ml), dried over MgSO$_4$ and concentrated in vacuo. The residue was purified by column chromatography over silica gel eluting with a mixture of ethyl acetate and heptane (1:2). The pure fractions were pooled and concentrated in vacuo. The residue was crystallised from a mixture of methyl tert-butyl ether and heptane to afford 2.13 g (98%) of the title compound.

M.p. 68–70° C.

Calculated for $C_{22}H_{18}F_3NO_3S.0.25H_2O$:
C, 60.34%; H, 4.26%; N, 3.20%. Found:
C, 60.35%; H, 4.38%; N, 3.07%;
C, 60.34%; H, 4.33%; N, 3.09%.

Example 38

[4-(4-Trifluoromethoxyphenyl)-4,5,6,7-tetrahydro-thieno[3,2-c]pyridin-5-yl]-(4-methoxyphenyl)-methanone

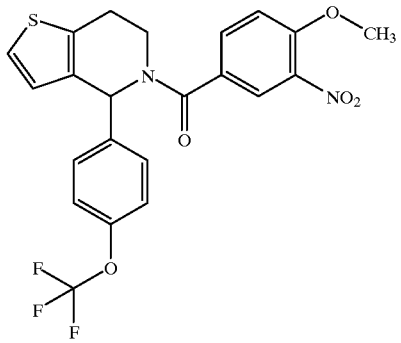

Similarly as described in example 22 using a solution of 4-(4-trifluoromethoxyphenyl)4,5,6,7-tetrahydro-thieno[3,2-c]pyridine in N,N-dimethylformamide (0.375 M, 0.4 ml, 0.15 mmol), a solution of 4-methoxy-3-nitrobenzoic acid in N,N-dimethylformamide (0.375 M, 0.4 ml, 0.15 mmol) and 0.25 ml of a suspension of N-(3-dimethylaminopropyl)-N'-ethylcarbodiimide hydrochloride in dichloromethane (1.73 g in 8.3 ml) affords the title compound.

MS (electrospray): m/e: 479 (M+1)
HPLC (method B): $R_t$=32.5 min.

Example 39

[4-(4-Trifluoromethylphenyl)-4,5,6,7-tetrahydro-thieno[3,2-c]pyridin-5-yl]-(4-methylsulfanylphenyl)-methanone

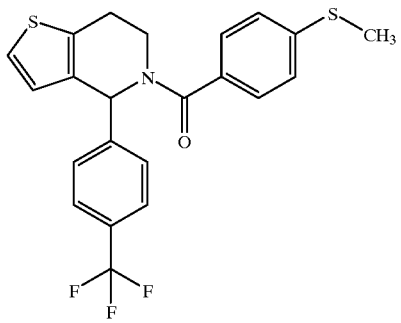

Similarly as described in example 22 using a solution of 4-(4-trifluoromethylphenyl)-4,5,6,7-tetrahydro-thieno[3,2- c]pyridine in N,N-dimethylformamide (0.375 M, 0.4 ml, 0.15 mmol), a solution of 4-methylsulfanylbenzoic acid in N,N-dimethylformamide (0.375 M, 0.4 ml, 0.15 mmol) and 0.25 ml of a suspension of N-(3-dimethylaminopropyl)-N'-ethylcarbodiimide hydrochloride in dichloromethane (1.73 g in 8.3 ml) affords the title compound.

MS (electrospray): m/z: 434 (M+1)

HPLC (method B): $R_t$=33.5 min.

Example 40

4-[4-(4-Trifluoromethylphenyl)-4,5,6,7-tetrahydro-thieno[3,2-c]pyridine-5-carbonyl]benzoic Acid Methyl Ester

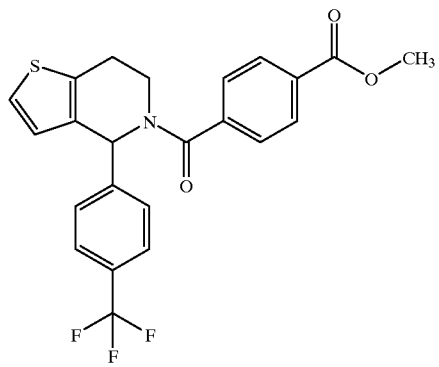

Similarly as described in example 22 using a solution of 4-(4-trifluoromethylphenyl)-4,5,6,7-tetrahydro-thieno[3,2-c]pyridine in N,N-dimethylformamide (0.375 M, 0.4 ml, 0.15 mmol), a solution of mono methyl terephthalic acid in N,N-dimethylformamide (0.375 M, 0.4 ml, 0.15 mmol) and 0.25 ml of a suspension of N-(3-dimethylaminopropyl)-N'-ethylcarbodiimide hydrochloride in dichloromethane (1.73 g in 8.3 ml) affords the title compound.

MS (electrospray): m/z: 446 (M+1)

HPLC (method B): $R_t$=31.9 min.

Example 41

(4-Hyroxymethylphenyl)-[4-(4-trifluoromethylphenyl)-4,5,6,7-tetrahydro-thieno[3,2-c]pyridin-5-yl]methanone

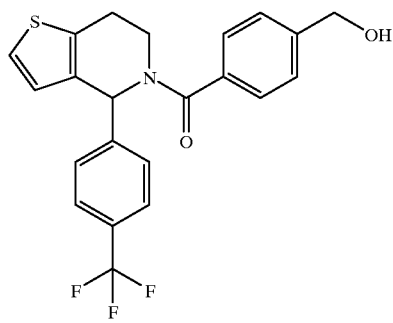

Similarly as described in example 22 using a solution of 4-(4-trifluoromethylphenyl)-4,5,6,7-tetrahydro-thieno[3,2-c]pyridine in N,N-dimethylformamide (0.375 M, 0.4 ml, 0.15 mmol), a solution of 4-hydroxymethylbenzoic acid in N,N-dimethylformamide (0.375 M, 0.4 ml, 0.15 mmol) and 0.25 ml of a suspension of N-(3-dimethylaminopropyl)-N'-ethylcarbodiimide hydrochloride in dichloromethane (1.73 g in 8.3 ml) affords the title compound.

MS (electrospray): m/z: 418 (M+1)

HPLC (method B): $R_t$=27.2 min.

Example 42

4-Acetoxyphenyl)[4-(4-trifluoromethylphenyl)-4,5,6,7-tetrahydro-thieno[3,2-c]pyridin-5-yl]methanone

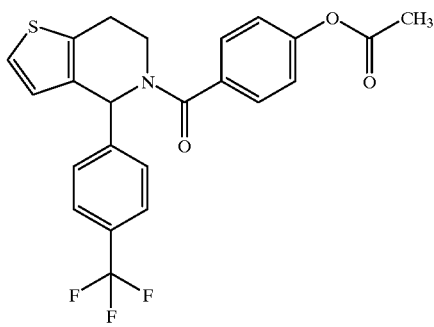

Similarly as described in example 22 using a solution of 4-(4-trifluoromethylphenyl)-4,5,6,7-tetrahydro-thieno[3,2-c]pyridine in N,N-dimethylformamide (0.375 M, 0.4 ml, 0.15 mmol), a solution of 4-acetoxybenzoic acid in N,N-dimethylformamide (0.375 M, 0.4 ml, 0.15 mmol) and 0.25 ml of a suspension of N-(3-dimethylaminopropyl)-N'-ethylcarbodiimide hydrochloride in dichloromethane (1.73 g in 8.3 ml) affords the title compound.

MS (electrospray): m/z: 446 (M+1)

HPLC (method B): $R_t$=30.7 min.

Example 43

(4-Cyanophenyl)-[4-(4-trifluoromethylphenyl)-4,5,6,7-tetrahydro-thieno[3,2-c]pyridin-5-yl]methanone

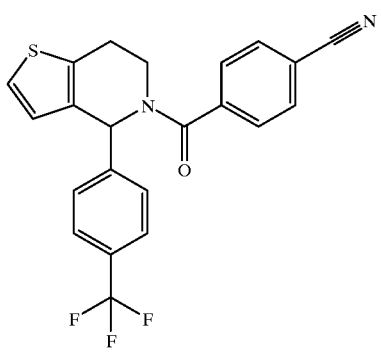

Similarly as described in example 22 using a solution of 4-(4-trifluoromethylphenyl)4,5,6,7-tetrahydro-thieno[3,2-c]pyridine in N,N-dimethylformamide (0.375 M, 0.4 ml, 0.15 mmol), a solution of 4 cyanobenzoic acid in N,N-dimethylformamide (0.375 M, 0.4 ml, 0.15 mmol) and 0.25 ml of a suspension of N-(3-dimethylaminopropyl)-N'-ethylcarbodiimide hydrochloride in dichloromethane (1.73 g in 8.3 ml) affords the title compound.

MS (electrospray): m/z: 413 (M+1)

HPLC (method B): $R_t$=30.6 min.

Example 44

1-{4-[4-(4-Trifluoromethylphenyl)4,5,6,7-tetrahydro-thieno[3,2-c]pyridine-5-carbonyl]phenyl}ethanone

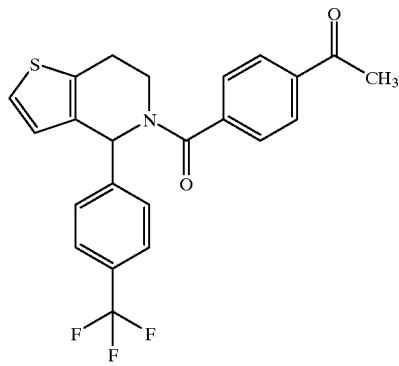

Similarly as described in example 22 using a solution of 4-(4-trifluoromethylphenyl)-4,5,6,7-tetrahydro-thieno[3,2-c]pyridine in N,N-dimethylformamide (0.375 M, 0.4 ml, 0.15 mmol), a solution of 4-acetylbenzoic acid in N,N-dimethylformamide (0.375 M, 0.4 ml, 0.15 mmol) and 0.25 ml of a suspension of N-(3-dimethylaminopropyl)-N'-ethylcarbodiimide hydrochloride in dichloromethane (1.73 g in 8.3 ml) affords the title compound.

MS (electrospray): m/z: 430 (M+1)

HPLC (method B): $R_t$=30.5 min.

Example 45

3-Furan-2-yl-1-[4-(4-trifluoromethylphenyl)-4,5,6,7-tetrahydro-thieno[3,2-c]pyridin-5-yl]propenone

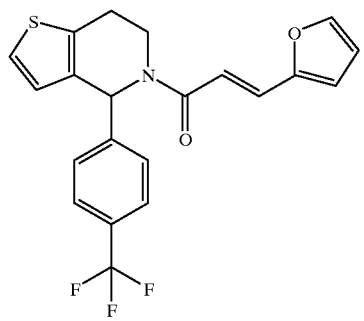

Similarly as described in example 22 using a solution of 4-(4-trifluoromethylphenyl)4,5,6,7-tetrahydro-thieno[3,2-c]pyridine in N,N-dimethylformamide (0.375 M, 0.4 ml, 0.15 mmol), a solution of 3-(furan-2-yl)acrylic acid in N,N-dimethylformamide (0.375 M, 0.4 ml, 0.15 mmol) and 0.25 ml of a suspension of N-(3-dimethylaminopropyl)-N'-ethylcarbodiimide hydrochloride in dichloromethane (1.73 g in 8.3 ml) affords the title compound.

MS (electrospray): m/z: 404 (M+1)

HPLC (method B): $R_t$=32.2 min.

Example 46

3-(5-Methylfuran-2-yl)-1-[4-(4-trifuoromethylphenyl)-4,5,6,7-tetrahydro-thieno[3,2-c]pyridin-5-yl]propenone

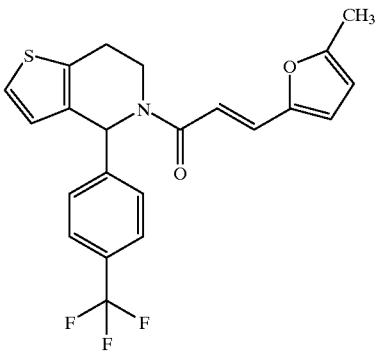

Similarly as described in example 22 using a solution of 4-(4-trifluoromethylphenyl)-4,5,6,7-tetrahydro-thieno[3,2-c]pyridine in N,N-dimethylformamide (0.375 M, 0.4 ml, 0.15 mmol), a solution of 3-(5-methylfuran-2-yl)acrylic acid in N,N-dimethylformamide (0.375 M, 0.4 ml, 0.15 mmol) and 0.25 ml of a suspension of N-(3-dimethylaminopropyl)-N'-ethylcarbodiimide hydrochloride in dichloromethane (1.73 g in 8.3 ml) affords the title compound.

MS (electrospray): m/z: 418 (M+1)

HPLC (method B): $R_t$=33.7 min.

Example 47

Benzo[b]thiophen-2-yl-1-[4-(4-trifluoromethylphenyl)4,5,6,7-tetrahydro-thieno[3,2-c]pyridin-5-yl]methanone

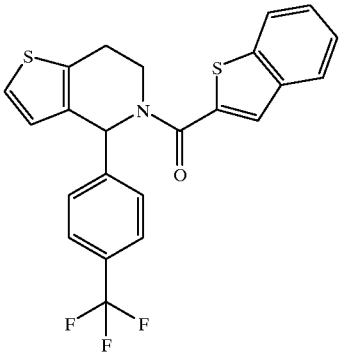

Similarly as described in example 22 using a solution of 4-(4-trifluoromethylphenyl)-4,5,6,7-tetrahydro-thieno[3,2-c]pyridine in N,N-dimethylformamide (0.375 M, 0.4 ml, 0.15 mmol), a solution of benzo[b]thiophen-2-yl-carboxylic acid in N,N-dimethylformamide (0.375 M, 0.4 ml, 0.15 mmol) and 0.25 ml of a suspension of N-(3-dimethylaminopropyl)-N'-ethylcarbodiimide hydrochloride in dichloromethane (1.73 g in 8.3 ml) affords the title compound.

MS (electrospray): m/z: 444 (M+1)

HPLC (method B): $R_t$=35.1 min.

Example 48

3-Furan-3-yl-1-[4-(4-trifluoromethylphenyl)4,5,6,7-tetrahydro-thieno[3,2-c]pyridin-5-yl]propenone

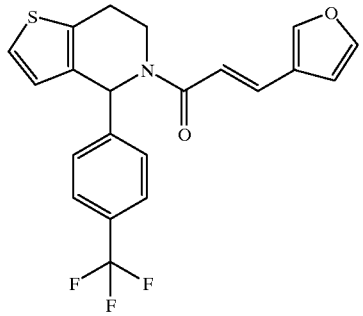

Similarly as described in example 22 using a solution of 4-(4-trifluoromethylphenyl)-4,5,6,7-tetrahydro-thieno[3,2-c]pyridine in N,N-dimethylformamide (0.375 M, 0.4 ml, 0.15 mmol), a solution of 3-furan-3-ylacrylic acid in N,N-dimethylformamide (0.375 M, 0.4 ml, 0.15 mmol) and 0.25 ml of a suspension of N-(3-dimethylaminopropyl)-N'-ethylcarbodiimide hydrochloride in dichloromethane (1.73 g in 8.3 ml) affords the title compound.

MS (electrospray): m/z: 404 (M+1)

HPLC (method B): $R_t$=31.4 min.

Example 49

3Thiophen-3-yl-1-[4-(4-trifluoromethylphenyl)-4,5,6,7-tetrahydro-thieno[3,2-c]pyridin-5-yl]propenone

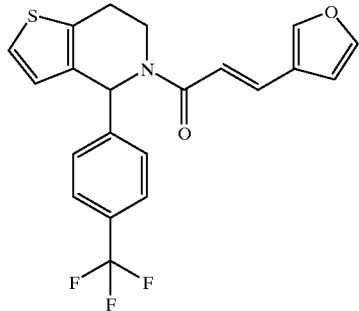

Similarly as described in example 22 using a solution of 4-(4-trifluoromethylphenyl)-4,5,6,7-tetrahydro-thieno[3,2-c]pyridine in N,N-dimethylformamide (0.375 M, 0.4 ml, 0.15 mmol), a solution of 3-thiophen-3-ylacrylic acid in N,N-dimethylformamide (0.375 M, 0.4 ml, 0.15 mmol) and 0.25 ml of a suspension of N-(3-dimethylaminopropyl)-N'-ethylcarbodiimide hydrochloride in dichloromethane (1.73 g in 8.3 ml) affords the title compound.

MS (electrospray): m/z: 420 (M+1)

HPLC (method B): $R_t$=32.8 min.

Example 50

3-Thiophen-2-yl-1-[4-(4-trifluoromethylphenyl)-4,5,6,7-tetrahydro-thieno[3,2-c]pyridin-5-yl]propenone

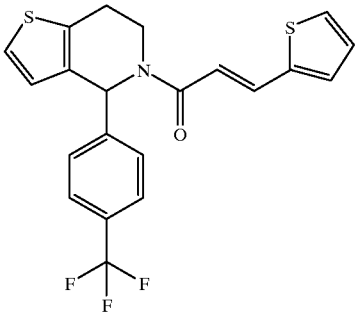

Similarly as described in example 22 using a solution of 4-(4-trifluoromethylphenyl)-4,5,6,7-tetrahydro-thieno[3,2-c]pyridine in N,N-dimethylformamide (0.375 M, 0.4 ml, 0.15 mmol), a solution of 3-thiophen-3-ylacrylic acid in N,N-dimethylformamide (0.375 M, 0.4 ml, 0.15 mmol) and 0.25 ml of a suspension of N-(3-dimethylaminopropyl)-N'-ethylcarbodiimide hydrochloride in dichloromethane (1.73 g in 8.3 ml) affords the title compound.

MS (electrospray): m/z: 420 (M+1)

HPLC (method B): $R_t$=33.3 min.

Example 51

[4-(4-Methoxyphenyl)4,5,6,7-tetrahydro-thieno[3,2-c]pyridin-5-yl]-(4-methylsulfanylphenyl)methanone

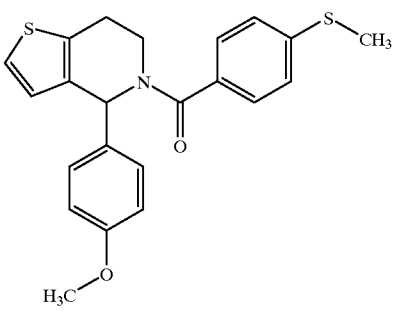

Similarly as described in example 22 using a solution of 4-(4-methoxyphenyl)-4,5,6,7-tetrahydro-thieno[3,2-c]pyridine in N,N-dimethylformamide (0.375 M, 0.4 ml, 0.15 mmol), a solution of 4-methylsulfanylbenzoic acid in N,N-dimethylformamide (0.375 M, 0.4 ml, 0.15 mmol) and 0.25 ml of a suspension of N-(3-dimethylaminopropyl)-N'-ethylcarbodiimide hydrochloride in dichloromethane (1.73 g in 8.3 ml) affords the title compound.

MS (electrospray): m/z: 396 (M+1)

HPLC (method B): $R_t$=29.5 min.

Example 52

[4-(4-Methoxyphenyl)-4,5,6,7-tetrahydro-thieno[3,2-c]pyridine-5-carbonyl]benzonitrile

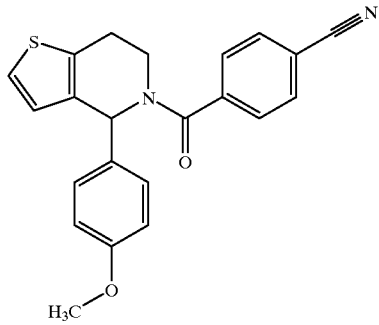

Similarly as described in example 22 using a solution of 4-(4-methoxyphenyl)-4,5,6,7-tetrahydro-thieno[3,2-c]pyridine in N,N-dimethylformamide (0.375 M, 0.4 ml, 0.15 mmol), a solution of 4-cyanobenzoic acid in N,N-dimethylformamide (0.375 M, 0.4 ml, 0.15 mmol) and 0.25 ml of a suspension of N-(3-dimethylaminopropyl)-N'-ethylcarbodiimide hydrochloride in dichloromethane (1.73 g in 8.3 ml) affords the title compound.

MS (electrospray): m/z: 375 (M+1)

HPLC (method B): $R_t$=26.2 min.

Example 53

3-Furan-3-yl-[4-(4-methoxyphenyl)-4,5,6,7-tetrahydro-thieno[3,2-c]pyridin-5-yl]propenone

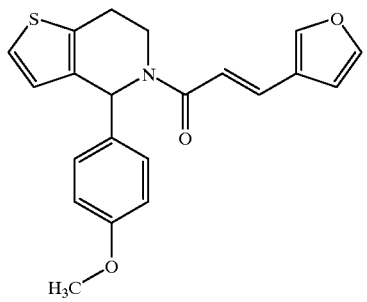

Similarly as described in example 22 using a solution of 4-(4-methoxyphenyl)-4,5,6,7-tetrahydro-thieno[3,2-c]pyridine in N,N-dimethylformamide (0.375 M, 0.4 ml, 0.15 mmol), a solution of 3-(furan-3-yl)acrylic acid in N,N-dimethylformamide (0.375 M, 0.4 ml, 0.15 mmol) and 0.25 ml of a suspension of N-(3-dimethylaminopropyl)-N'-ethylcarbodiimide hydrochloride in dichloromethane (1.73 9 in 8.3 ml) affords the title compound.

MS (electrospray): m/z: 366 (M+1)

HPLC (method B): $R_t$=26.9 min.

Example 54

(4-Methoxyphenyl)-[4-(4-methoxyphenyl)-4,5,6,7-tetrahydro-thieno[3,2-c]pyridin-5-yl]methanone

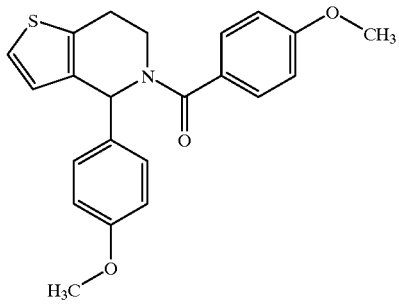

Similarly as described in example 22 using a solution of 4-(4-methoxyphenyl)-4,5,6,7-tetrahydro-thieno[3,2-c]pyridine in N,N-dimethylformamide (0.375 M, 0.4 ml, 0.15 mmol), a solution of 4-methoxybenzoic acid in N,N-dimethylformamide (0.375 M, 0.4 ml, 0.15 mmol) and 0.25 ml of a suspension of N-(3-dimethylaminopropyl)-N'-ethylcarbodiimide hydrochloride in dichloromethane (1.73 g in 8.3 ml) affords the title compound.

MS (electrospray): m/z: 380 (M+1)

HPLC (method B): $R_t$=27.6 min.

Example 55

(4-Fluorophenyl)-[4-(4-methoxyphenyl)-4,5,6,7-tetrahydro-thieno[3,2-c]pyridin-5-yl]methanone

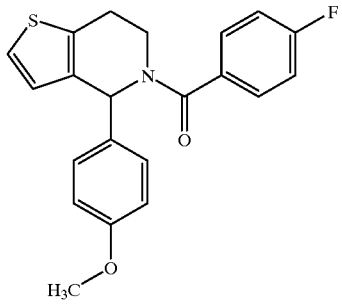

Similarly as described in example 22 using a solution of 4-(4-methoxyphenyl)-4,5,6,7-tetrahydro-thieno[3,2-c]pyridine in N,N-dimethylformamide (0.375 M, 0.4 ml, 0.15 mmol), a solution of 4-fluorobenzoic acid in N,N-dimethylformamide (0.375 M, 0.4 ml, 0.15 mmol) and 0.25 ml of a suspension of N-(3-dimethylaminopropyl)-N'-ethylcarbodiimide hydrochloride in dichloromethane (1.73 9 in 8.3 ml) affords the title compound.

MS (electrospray): m/z: 368 (M+1)

HPLC (method B): $R_t$=27.7 min.

Example 56

(4-Chlorophenyl)-[4-(4-trifluoromethoxyphenyl)-4,5,6,7-tetrahydro-thieno[3,2-c]pyridin-5-yl]methanone

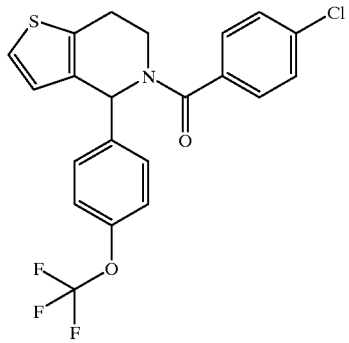

Similarly as described in example 22 using a solution of 4-(4-trifluoromethoxyphenyl)-4,5,6,7-tetrahydro-thieno[3,2-c]pyridine in N,N-dimethylformamide (0.375 M, 0.4 ml, 0.15 mmol), a solution of 4-chlorobenzoic acid in N,N-dimethylformamide (0.375 M, 0.4 ml, 0.15 mmol) and 0.25 ml of a suspension of N-(3-dimethylaminopropyl)-N'-ethylcarbodiimide hydrochloride in dichloromethane (1.73 g in 8.3 ml) affords the title compound.

MS (electrospray): m/z: 438 (M+1)

HPLC (method B): $R_t$=32.8 min.

Example 57

4-Methylsulfanylphenyl)-[4-(4-trifluoromethoxyphenyl)-4,5,6,7-tetrahydro-thieno[3,2-c]pyridin-5-yl]methanone

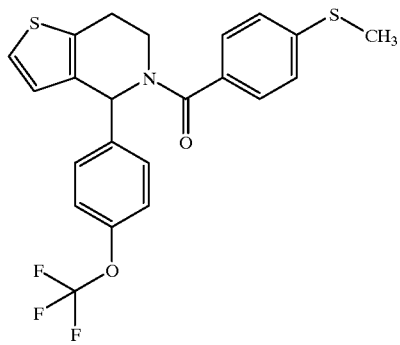

Similarly as described in example 22 using a solution of 4-(4-trifluoromethoxyphenyl)-4,5,6,7-tetrahydro-thieno[3,2-c]pyridine in N,N-dimethylformamide (0.375 M, 0.4 ml, 0.15 mmol), a solution of 4-methylsulfanylbenzoic acid in N,N-dimethylformamide (0.375 M, 0.4 ml, 0.15 mmol) and 0.25 ml of a suspension of N-(3-dimethylaminopropyl)-N'-ethylcarbodiimide hydrochloride in dichloromethane (1.73 g in 8.3 ml) affords the title compound.

MS (electrospray): m/z: 450 (M+1)

HPLC (method B): $R_t$=32.6 min.

Example 58

(4-Dimethylaminophenyl)[4-(4-trifluoromethoxyphenyl)-4,5,6,7-tetrahydro-thieno[3,2-c]pyridin-5-yl]methanone

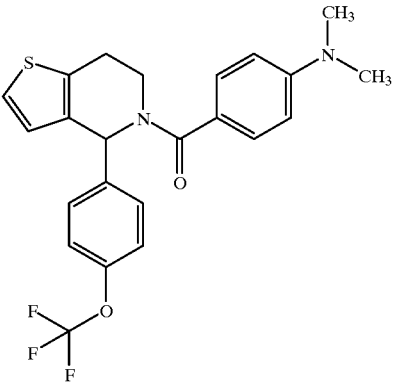

Similarly as described in example 22 using a solution of 4-(4-trifluoromethoxyphenyl)4,5,6,7-tetrahydro-thieno[3,2-c]pyridine in N,N-dimethylformamide (0.375 M, 0.4 ml, 0.15 mmol), a solution of 4-dimethylaminobenzoic acid in N,N-dimethylformamide (0.375 M, 0.4 ml, 0.15 mmol) and 0.25 ml of a suspension of N-(3-dimethylaminopropyl)-N'-ethylcarbodiimide hydrochloride in dichloromethane (1.73 9 in 8.3 ml) affords the title compound.

MS (electrospray): m/z: 447 (M+1)

HPLC (method B): $R_t$=27.1 min.

Example 59

(4-Hydroxymethylphenyl)-[4-(4-trifluoromethoxyphenyl)4,5,6,7-tetrahydro-thieno[3,2-c]pyridin-5-yl]methanone

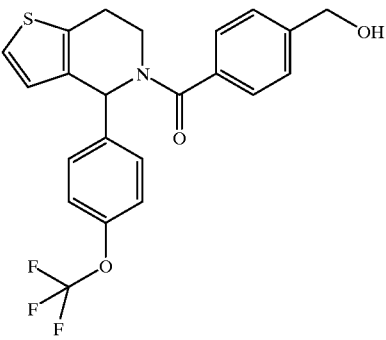

Similarly as described in example 22 using a solution of 4-(4-trifluoromethoxyphenyl)-4,5,6,7-tetrahydro-thieno[3,2-c]pyridine in N,N-dimethylformamide (0.375 M, 0.4 ml, 0.15 mmol), a solution of 4-hydroxymethylbenzoic acid in N,N-dimethylformamide (0.375 M, 0.4 ml, 0.15 mmol) and 0.25 ml of a suspension of N-(3-dimethylaminopropyl)-N'-ethylcarbodiimide hydrochloride in dichloromethane (1.73 g in 8.3 ml) affords the title compound.

MS (electrospray): m/z: 434 (M+1)

HPLC (method B): $R_t$=26.6 min.

Example 60

3-Furan-3-yl-1-[4-(4-trifluoromethoxyphenyl)-4,5,6,7-tetrahydro-thieno[3,2-c]pyridin-5-yl]propenone

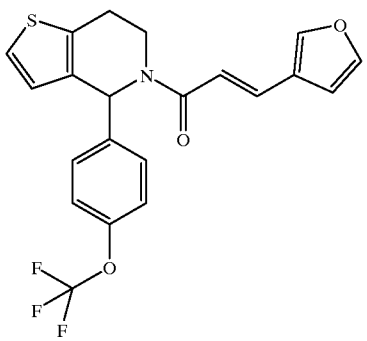

Similarly as described in example 22 using a solution of 4-(4-trifluoromethoxyphenyl)-4,5,6,7-tetrahydro-thieno[3,2-c]pyridine in N,N-dimethylformamide (0.375 M, 0.4 ml, 0.15 mmol), a solution of 3-(3-furan-3-yl)acrylic acid in N,N-dimethylformamide (0.375 M, 0.4 ml, 0.15 mmol) and 0.25 ml of a suspension of N-(3-dimethylaminopropyl)-N'-ethylcarbodiimide hydrochloride in dichloromethane (1.73 g in 8.3 ml) affords the title compound.

MS (electrospray): m/z: 420 (M+1)

HPLC (method B): $R_t$=30.4 min.

Example 61

4-(4-Chlorophenyl)-5-(4-methoxybenzyl)-4,5,6,7-tetrahydro-thieno[3,2-c]pyridine Hydrochloride

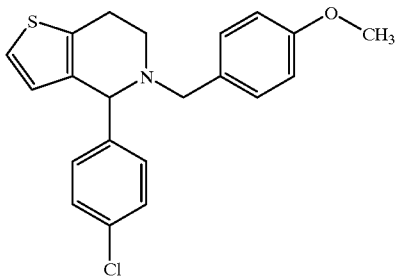

4-(4-Chlorophenyl)-4,5,6,7-tetrahydro-thieno[3,2-c]pyridine (0.10 g, 0.38 mmol) was dissolved in N,N-dimethylformamide (0.5 ml) and triethylamine (110 μl, 0.76 mmol) and 4-methoxybenzyl chloride (51 μl, 0.38 mmol) were added and the resulting mixture was shaken at 1000 rpm for 3 days. Water (2 ml) was added and the mixture was extracted with ethyl acetate (2×1 ml). The combined organic extracts were concentrated in vacuo. The residue was purified by preparative thin layer chromatography eluting with a mixture of ethyl acetate and heptane (1:4) to afford the free base. This was dissolved in diethyl ether and 1N HCl in diethyl ether was added drop wise to complete precipitation to afford 52 mg (34%) of the title compound.

HPLC-MS: $R_t$=9.57 min. m/z=370 (M+1).

Example 62

[4-(4-Chlorophenyl)-4,5,6,7-tetrahydro-thieno[3,2-c]pyridin-5-yl]-(4-hydroxyphenyl)methanone

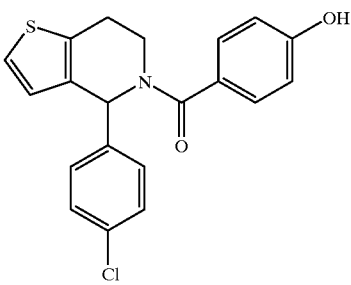

4-Hydroxybenzoic acid (1.3 g, 9.6 mmol) was dissolved in N,N-dimethylformamide (25 ml) and 1-hydroxybenzotriazole (1.3 g, 9.6 mmol) was added followed by N-(3-dimethylaminopropyl)-N'-ethylcarbodiimide hydrochloride (1.8 g, 9.6 mmol), 4-(4-chlorophenyl)4,5,6,7-tetrahydro-thieno[3,2-c]pyridine (2.0 g, 8 mmol) and N,N-diisopropylethylamine (2.5 ml, 16 mmol). The resulting mixture was stirred at room temperature for 16 hours. Water (200 ml) was added and the mixture was extracted with diethyl ether (3×100 ml). The combined organic extracts were washed with saturated aqueous sodium chloride (150 ml), dried over MgSO$_4$ and concentrated in vacuo. The residue was purified by column chromatography over silica gel eluting with a mixture of ethyl acetate and heptane (1:1). The pure fractions were pooled and concentrated in vacuo to afford 3.14 9 (100%) of the title compound.

M.p. 202–207° C.

Calculated for $C_{20}H_{16}ClNO_2S$:

C, 64.95%; H, 4.36%; N, 3.79%. Found:

C, 64.54%; H, 4.74%; N, 4.29%;

C, 64.63%; H, 4.76%; N, 4.28%.

HPLC-MS: $R_t$=14.18 min. m/z: 370 (M+1)

Example 63

1-[4-(4-Chlorophenyl)-4,5,6,7-tetrahydro-thieno[3,2-c]pyridin-5-yl]-2-(4-methoxyphenyl)ethanone

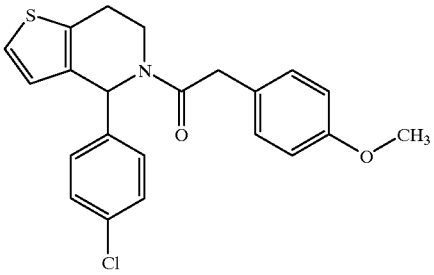

Similarly as described in example 22 using a solution of 4-(4-chlorophenyl)-4,5,6,7-tetrahydro-thieno[3,2-c]pyridine in N,N-dimethylformamide (0.375 M, 0.4 ml, 0.15 mmol), a solution of 4-methoxyphenylacetic acid in N,N-dimethylformamide (0.375 M, 0.4 ml, 0.15 mmol) and 0.25 ml of a suspension of N-(3-dimethylaminopropyl)-N'-ethylcarbodiimide hydrochloride in dichloromethane (1.73 g in 8.3 ml) affords the title compound.

MS (electrospray): m/z: 398 (M+1)

HPLC (method B): $R_t$=32.2 min.

Example 64

[4-(4-Chlorophenyl)-4,5,6,7-tetrahydro-thieno[3,2-c]pyridin-5-yl]-(3-dimethylaminophenyl)methanone

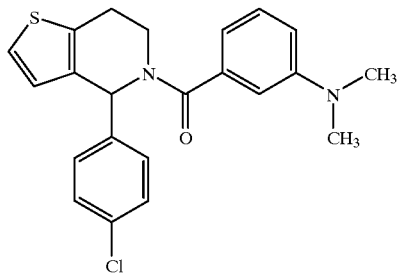

Similarly as described in example 22 using a solution of 4-(4-chlorophenyl)-4,5,6,7-tetrahydro-thieno[3,2-c]pyridine in N,N-dimethylformamide (0.375 M, 0.4 ml, 0.15 mmol), a solution of 3-dimethylaminobenzoic acid in N,N-dimethylformamide (0.375 M, 0.4 ml, 0.15 mmol) and 0.25 ml of a suspension of N-(3-dimethylaminopropyl)-N'-ethylcarbodiimide hydrochloride in dichloromethane (1.73 g in 8.3 ml) affords the title compound.

MS (electrospray): m/z: 397 (M+1)

HPLC (method B): $R_t$=25.9 min.

Example 65

N-{4-[4-(4-Chlorophenyl)-4,5,6,7-tetrahydro-thieno[3,2-c]pyridine-5-carbonyl]phenyl}acetamide

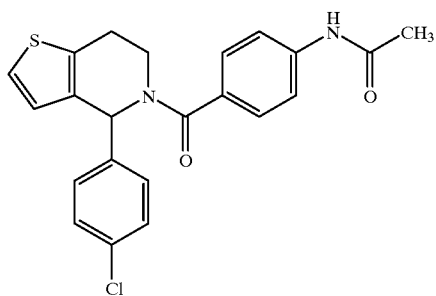

Similarly as described in example 22 using a solution of 4-(4-chlorophenyl)4,5,6,7-tetrahydro-thieno[3,2-c]pyridine in N,N-dimethylformamide (0.375 M, 0.4 ml, 0.15 mmol), a solution of 4-acetamidobenzoic acid in N,N-dimethylformamide (0.375 M, 0.4 ml, 0.15 mmol) and 0.25 ml of a suspension of N-(3-dimethylaminopropyl)-N'-ethylcarbodiimide hydrochloride in dichloromethane (1.73 g in 8.3 ml) affords the title compound.

MS (electrospray): m/z: 411 (M+1)

HPLC (method B): $R_t$=27.2 min.

Example 66

[4-(4-Chlorophenyl)-4,5,6,7-tetrahydro-thieno[3,2-c]pyridin-5-yl]-(4-methanesulfonylphenyl)methanone

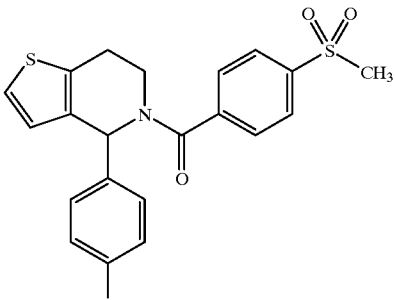

Similarly as described in example 22 using a solution of 4-(4-chlorophenyl)-4,5,6,7-tetrahydro-thieno[3,2-c]pyridine in N,N-dimethylformamide (0.375 M, 0.4 ml, 0.15 mmol), a solution of 4-methanesulfonylbenzoic acid in N,N-dimethylformamide (0.375 M, 0.4 ml, 0.15 mmol) and 0.25 ml of a suspension of N-(3-dimethylaminopropyl)-N'-ethylcarbodiimide hydrochloride in dichloromethane (1.73 g in 8.3 ml) affords the title compound.

MS (electrospray): m/z: 432 (M+1)

HPLC (method B): $R_t$=28.1 min.

Example 67

2-(4-Chlorophenyl)-1 -[4-(4-chlorophenyl)-4,5,6,7-tetrahydro-thieno[3,2-c]pyridin-5-yl]ethanone

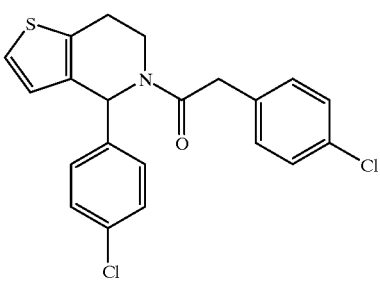

Similarly as described in example 22 using a solution of 4-(4-chlorophenyl)-4,5,6,7-tetrahydro-thieno[3,2-c]pyridine in N,N-dimethylformamide (0.375 M, 0.4 ml, 0.15 mmol), a solution of 4-chlorophenylacetic acid in N,N-dimethylformamide (0.375 M, 0.4 ml, 0.15 mmol) and 0.25 ml of a suspension of N-(3-dimethylaminopropyl)-N'-ethylcarbodiimide hydrochloride in dichloromethane (1.73 g in 8.3 ml) affords the title compound.

MS (electrospray): m/z: 402 (M+1)

HPLC (method B): $R_t$=34.5 min.

Example 68

2-(4-Methoxyphenyl)-1-[4-(4-trifluoromethoxyphenyl)-4,5,6,7-tetrahydro-thieno[3,2-c]pyridin-5-yl]-ethanone

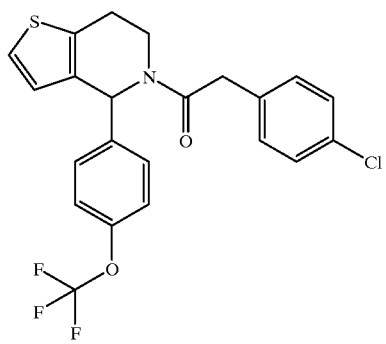

Similarly as described in example 22 using a solution of 4-(4-trifluoromethoxyphenyl)-4,5,6,7-tetrahydro-thieno[3,2-c]pyridine in N,N-dimethylformamide (0.375 M, 0.4 ml, 0.15 mmol), a solution of 4-chlorophenylacetic add in N,N-dimethylformamide (0.375 M, 0.4 ml, 0.15 mmol) and 0.25 ml of a suspension of N-(3-dimethylaminopropyl)-N'-ethylcarbodiimide hydrochloride in dichloromethane (1.73 g in 8.3 ml) affords the title compound.

MS (electrospray): m/z: 448 (M+1)

HPLC (method B): $R_t$=32.9 min.

Example 69

(3-Dimethylaminophenyl)-[4-(4-trifluoromethoxyphenyl)-4,5,6,7-tetrahydro-thieno[3,2-c]pyridin-5-yl]-methanone

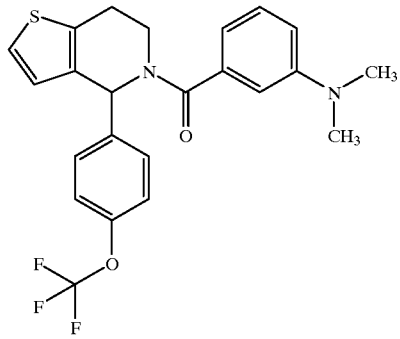

Similarly as described in example 22 using a solution of 4-(4-trifluoromethoxyphenyl)-4,5,6,7-tetrahydro-thieno[3,2-c]pyridine in N,N-dimethylformamide (0.375 M, 0.4 ml, 0.15 mmol), a solution of 3-dimethylaminobenzoic acid in N,N-dimethylformamide (0.375 M, 0.4 ml, 0.15 mmol) and 0.25 ml of a suspension of N-(3-dimethylaminopropyl)-N'-ethylcarbodiimide hydrochloride in dichloromethane (1.73 g in 8.3 ml) affords the title compound.

MS (electrospray): m/z: 447 (M+1)

HPLC (method B): $R_t$=27.2 min.

Example 70

N-{4-[4-(4-Trifluoromethoxyphenyl)4,5,6,7-tetrahydro-thieno[3,2-c]pyridine-5-carbonyl]-phenyl}-acetamide

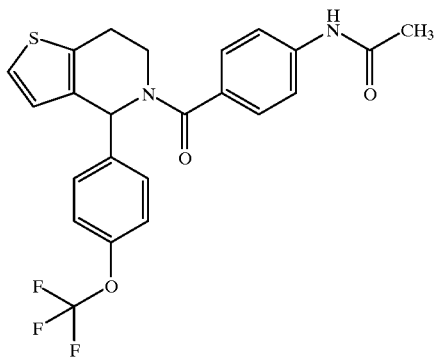

Similarly as described in example 22 using a solution of 4-(4-trifluoromethoxyphenyl)-4,5,6,7-tetrahydro-thieno[3,2-c]pyridine in N,N-dimethylformamide (0.375 M, 0.4 ml, 0.15 mmol), a solution of 4-acetamidobenzoic acid in N,N-dimethylformamide (0.375 M, 0.4 ml, 0.15 mmol) and 0.25 ml of a suspension of N-(3-dimethylaminopropyl)-N'-ethylcarbodiimide hydrochloride in dichloromethane (1.73 g in 8.3 ml) affords the title compound.

MS (electrospray): m/z: 461 (M+1)

HPLC (method B): $R_t$=28.2 min.

Example 71

(4-Methanesulfonylphenyl)-[4-(4-trifluoromethoxyphenyl)-4,5,6,7-tetrahydro-thieno[3,2-c]pyridin-5-yl]-methanone

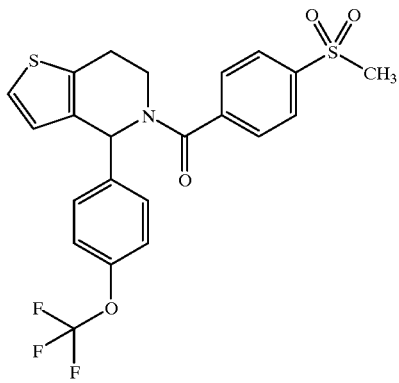

Similarly as described in example 22 using a solution of 4-(4-trifluoromethoxyphenyl)4,5,6,7-tetrahydro-thieno[3,2-c]pyridine in N,N-dimethylformamide (0.375 M, 0.4 ml, 0.15 mmol), a solution of 4-methanesulfonylbenzoic acid in N,N-dimethylformamide (0.375 M, 0.4 ml, 0.15 mmol) and 0.25 ml of a suspension of N-(3-dimethylaminopropyl)-N'-ethylcarbodiimide hydrochloride in dichloromethane (1.73 g in 8.3 ml) affords the title compound.

MS (electrospray): m/z: 482 (M+1)

HPLC (method B): $R_t$=29.1 min.

Example 72

2-(4-Chlorophenyl)-1-[4-(4-trifluoromethoxyphenyl)-4,5,6,7-tetrahydro-thieno[3,2-c]pyridin-yl ]-ethanone

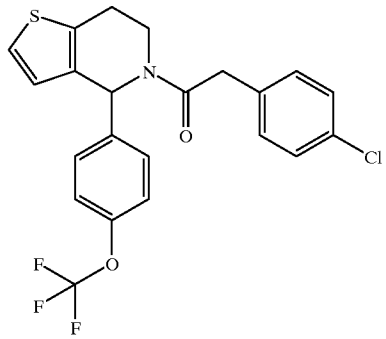

Similarly as described in example 22 using a solution of 4-(4-trifluoromethoxyphenyl)-4,5,6,7-tetrahydro-thieno[3,2-c]pyridine in N,N-dimethylformamide (0.375 M, 0.4 ml, 0.15 mmol), a solution of 4-chlorophenylacetic acid in N,N-dimethylformamide (0.375 M, 0.4 ml, 0.15 mmol) and 0.25 ml of a suspension of N-(3-dimethylaminopropyl)-N'-ethylcarbodiimide hydrochloride in dichloromethane (1.73 g in 8.3 ml) affords the title compound.

MS (electrospray): m/z: 452 (M+1)

HPLC (method B): $R_t$=34.9 min.

Example 73

Biphenyl-4-yl-[4-(4-trifluoromethoxyphenyl)-4,5,6,7-tetrahydro-thieno[3,2-c]pyridin-5-yl ]methanone

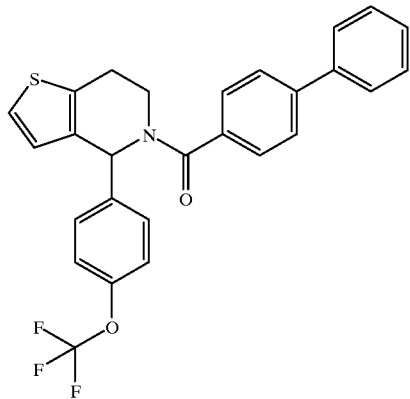

Similarly as described in example 22 using a solution of 4-(4-trifluoromethoxyphenyl)-4,5,6,7-tetrahydro-thieno[3,2-c]pyridine in N,N-dimethylformamide (0.375 M, 0.4 ml, 0.15 mmol), a solution of 4-biphenylcarboxylic acid in N,N-dimethylformamide (0.375 M, 0.4 ml, 0.15 mmol) and 0.25 ml of a suspension of N-(3-dimethylaminopropyl)-N'-ethylcarbodiimide hydrochloride in dichloromethane (1.73 g in 8.3 ml) affords the title compound.

MS (electrospray): m/z: 480 (M+1)

HPLC (method B): $R_t$=36.7 min.

Example 74

(3,4-Dichlorophenyl)-[4-(4-trifluoromethoxyphenyl)-4,5,6,7-tetrahydro-thieno[3,2-c]pyridin-5yl ]methanone

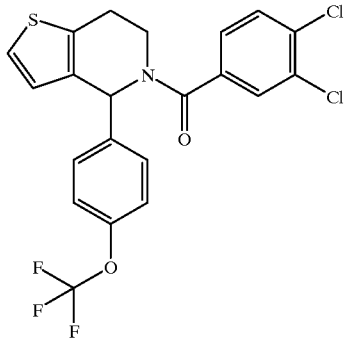

Similarly as described in example 22 using a solution of 4-(4-trifluoromethoxyphenyl)4,5,6,7-tetrahydro-thieno [3,2-c]pyridine in N,N-dimethylformamide (0.375 M, 0.4 ml, 0.15 mmol), a solution of 3,4-dichlorobenzoic acid in N,N-dimethylformamide (0.375 M, 0.4 ml, 0.15 mmol) and 0.25 ml of a suspension of N-(3-dimethylaminopropyl)-N'-ethylcarbodiimide hydrochloride in dichloromethane (1.73 g in 8.3 ml) affords the title compound.

MS (electrospray): m/z: 472 (M+1)

HPLC (method B): $R_t$=36.2 min.

Example 75

(4-tert-Butylphenyl)-[4-(4-trifluoromethoxyphenyl)-4,5,6,7-tetrahydro-thieno[3,2-c]pyridin-5-yl ]methanone

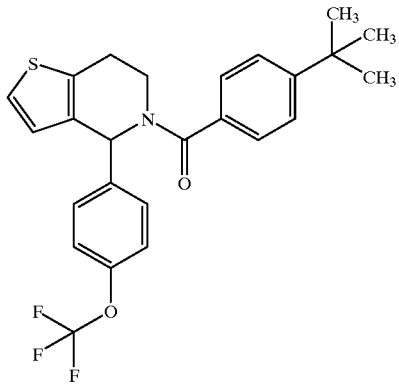

Similarly as described in example 22 using a solution of 4-(4-trifluoromethoxyphenyl)-4,5,6,7-tetrahydro-thieno [3,2-c]pyridine in N,N-dimethylformamide (0.375 M, 0.4 ml, 0.15 mmol), a solution of 4-tert-butylbenzoic acid in N,N-dimethylformamide (0.375 M, 0.4 ml, 0.15 mmol) and 0.25 ml of a suspension of N-(3-dimethylaminopropyl)-N'-ethylcarbodiimide hydrochloride in dichloromethane (1.73 g in 8.3 ml) affords the title compound.

MS (electrospray): m/z: 460 (M+1)

HPLC (method B): $R_t$=37.0 min.

Example 76

Pyridin4-yl-[4-(4-trifluoromethoxyphenyl)-4,5,6,7-tetrahydro-thieno[3,2-c]pyridin-5-yl]methanone

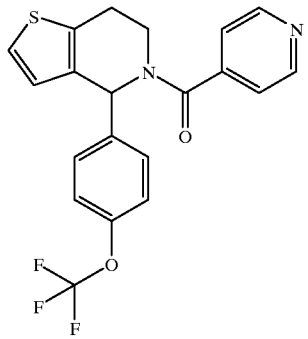

Similarly as described in example 22 using a solution of 4-(4-trifluoromethoxyphenyl)4,5,6,7-tetrahydro-thieno [3,2-c]pyridine in N,N-dimethylformamide (0.375 M, 0.4 ml, 0.15 mmol), a solution of pyridine-4-carboxylic acid in N,N-dimethylformamide (0.375 M, 0.4 ml, 0.15 mmol) and 0.25 ml of a suspension of N-(3-dimethylaminopropyl)-N'-ethylcarbodiimide hydrochloride in dichloromethane (1.73 g in 8.3 ml) affords the title compound.

MS (electrospray): m/z: 405 (M+1)

HPLC (method B): $R_t$=23.9 min.

Example 77

(5-Hydroxypyrazin-2-yl)-[4-(4-trifluoromethoxyphenyl)-4,5,6,7-tetrahydro-thieno[3,2-c]pyridin-5-yl]methanone

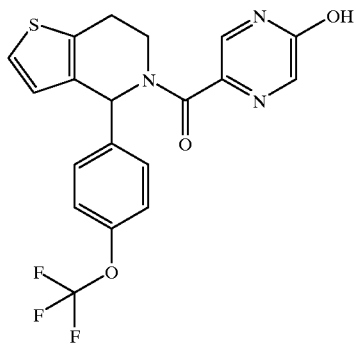

Similarly as described in example 22 using a solution of 4-(4-trifluoromethoxyphenyl)4,5,6,7,-tetrahydro-thieno [3,2-c]pyridine in N,N-dimethylformamide (0.375 M, 0.4 ml, 0.15 mmol), a solution of 5-hydroxypyrazine-2-carboxylic acid in N,N-dimethylformamide (0.375 M, 0.4 ml, 0.15 mmol) and 0.25 ml of a suspension of N-(3-dimethylaminopropyl)-N'-ethylcarbodiimide hydrochloride in dichloromethane (1.73 g in 8.3 ml) affords the title compound.

MS (electrospray): m/z: 422 (M+1)

HPLC (method B): $R_t$=26.0 min.

Example 78

(5Chloro-6-hydroxypyridin-3-yl)-[4-(4-trifluoromethoxyphenyl)-4,5,6,7-tetrahydro-thieno[3,2-c]pyridin-5-yl]methanone

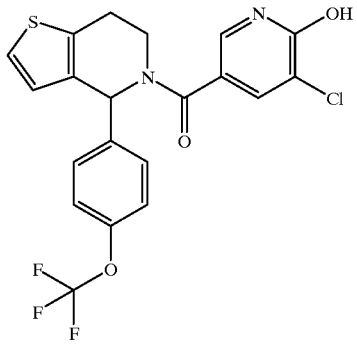

Similarly as described in example 22 using a solution of 4-(4-trifluoromethoxyphenyl)4,5,6,7-tetrahydro-thieno [3,2-c]pyridine in N,N-dimethylformamide (0.375 M, 0.4 ml, 0.15 mmol), a solution of 2-hydroxy-3-chloropyridine-5-carboxylic acid in N,N-dimethylformamide (0.375 M, 0.4 ml, 0.15 mmol) and 0.25 ml of a suspension of N-(3-dimethylaminopropyl)-N'-ethylcarbodiimide hydrochloride in dichloromethane (1.73 g in 8.3 ml) affords the title compound.

MS (electrospray): m/z: 455 (M+1)

HPLC (method B): $R_t$=26.8 min.

Example 79

3-(4,5-Dimethylfuran-2-yl)-1-[4-(4-trifluoromethylphenyl)-4,5,6,7-tetrahydro-thieno[3,2-c]pyridin-5-yl]propenone

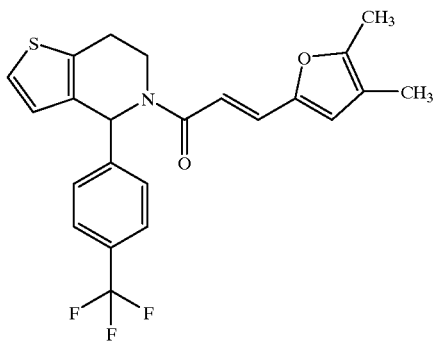

Similarly as described in example 22 using a solution of 4-(4-trifluoromethylphenyl)-4,5,6,7-tetrahydro-thieno [3,2-c]pyridine in N,N-dimethylformamide (0.375 M, 0.4 ml, 0.15 mmol), a solution of 3-(4,5-dimethylfuran-2-yl)acrylic acid in N,N-dimethylformamide (0.375 M, 0.4 ml, 0.15 mmol) and 0.25 ml of a suspension of N-(3-dimethylaminopropyl)-N'-ethylcarbodiimide hydrochloride in dichloromethane (1.73 g in 8.3 ml) affords the title compound.

MS (electrospray): m/z: 432 (M+1)

HPLC (method B): $R_t$=35.2 min.

Example 80

(1-Benzyl-1,2,3,4-tetrahydro-isoquinolin-2-yl)-(4-methoxyphenyl)methanone

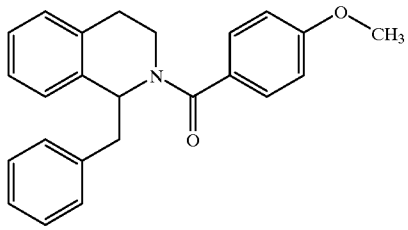

Similarly as described in example 22 using a solution of 1-benzyl-1,2,3,4-tetrahydro-isoquinoline in N,N-dimethylformamide (0.375 M, 0.4 ml, 0.15 mmol), a solution of 4-methoxybenzoic acid in N,N-dimethylformamide (0.375 M, 0.4 ml, 0.15 mmol) and 0.25 ml of a suspension of N-(3-dimethylaminopropyl)-N'-ethylcarbodiimide hydrochloride in dichloromethane (1.73 g in 8.3 ml) affords the title compound.

HPLC-MS: $R_t$=15.0 min. m/z: 358 (M+1)

Example 81

(1-Benzyl-1,2,3,4-tetrahydro-isoquinolin-2-yl)-(4-chlorophenyl)methanone

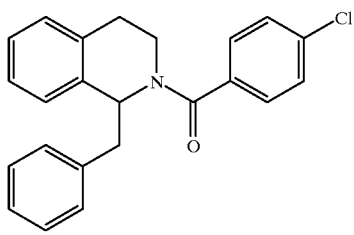

Similarly as described in example 22 using a solution of 1-benzyl-1,2,3,4-tetrahydriisoquinoline in N,N-dimethylformamide (0.375 M, 0.4 ml, 0.15 mmol), a solution of 4-chlorobenzoic acid in N,N-dimethylformamide (0.375 M, 0.4 ml, 0.15 mmol) and 0.25 ml of a suspension of N-(3-dimethylaminopropyl)-N'-ethylcarbodiimide hydrochloride in dichloromethane (1.73 g in 8.3 ml) affords the title compound.

HPLC-MS: $R_t$=16.1 min. m/z: 362 (M+1)

Example 82

(1H-Benzoimidazol-5-yl)-(1-benzyl-1,2,3,4-tetrahydro-isoquinolin-2-yl)methanone

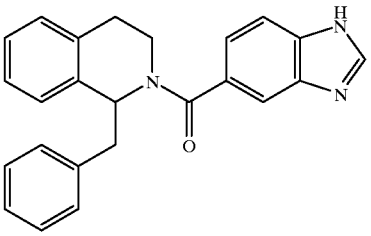

Similarly as described in example 22 using a solution of 1-benzyl-1,2,3,4-tetrahydro-isoquinoline in N,N-dimethylformamide (0.375 M, 0.4 ml, 0.15 mmol), a solution of benzimidazole-5-carboxylic acid in N,N-dimethylformamide (0.375 M, 0.4 ml, 0.15 mmol) and 0.25 ml of a suspension of N-(3-dimethylaminopropyl)-N'-ethylcarbodiimide hydrochloride in dichloromethane (1.73 g in 8.3 ml) affords the title compound.

HPLC-MS: $R_t$=9.55 min. m/z: 368 (M+1)

Exqample 83

(1-Benzyl-1,2,3,4-tetrahydro-isoquinolin-2-yl)-3-furan-3-ylpropenone

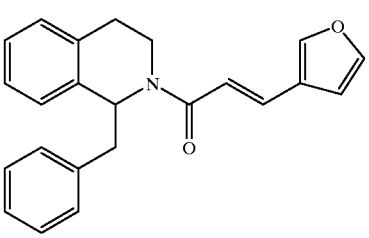

Similarly as described in example 22 using a solution of 1-benzyl-1,2,3,4-tetrahydro-isoquinoline in N,N-dimethylformamide (0.375 M, 0.4 ml, 0.15 mmol), a solution of 3-(3-furan-3-yl)acrylic acid in N,N-dimethylformamide (0.375 M, 0.4 ml, 0.15 mmol) and 0.25 ml of a suspension of N-(3-dimethylaminopropyl)-N'-ethylcarbodiimide hydrochloride in dichloromethane (1.73 g in 8.3 ml) affords the title compound.

HPLC-MS: $R_t$=14.7 min. m/z: 344 (M+1)

Example 84

1-(1-Benzyl-1,2,3,4-tetrahydro-isoquinolin-2-yl)-3-(4-methoxyphenyl)propenone

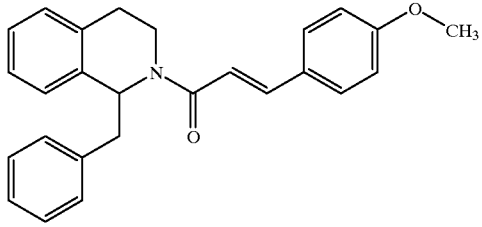

Similarly as described in example 22 using a solution of 1-benzyl-1,2,3,4-tetrahydro-isoquinoline in N,N-dimethylformamide (0.375 M, 0.4 ml, 0.15 mmol), a solution of 4-methoxycinnamic acid in N,N-dimethylformamide (0.375 M, 0.4 ml, 0.15 mmol) and 0.25 ml of a suspension of N-(3-dimethylaminopropyl)-N'-ethylcarbodiimide hydrochloride in dichloromethane (1.73 g in 8.3 ml) affords the title compound.

HPLC-MS: $R_t$=15.7 min. m/z: 384 (M+1)

Example 85

1-(1-Benzyl-1,2,3,4-tetrahydro-isoquinolin-2-yl)-3-(4-methoxyphenyl)propan-1-one

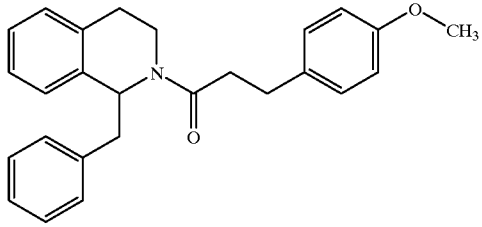

Similarly as described in example 22 using a solution of 1-benzyl-1,2,3,4-tetrahydro-isoquinoline in N,N-dimethylformamide (0.375 M, 0.4 ml, 0.15 mmol), a solution of 4-methoxyhydrocinnamic acid in N,N-dimethylformamide (0.375 M, 0.4 ml, 0.15 mmol) and 0.25 ml of a suspension of N-(3-dimethylaminopropyl)-N'-ethylcarbodiimide hydrochloride in dichloromethane (1.73 g in 8.3 ml) affords the title compound.

HPLC-MS: $R_t$=15.7 min. m/z: 386 (M+1)

Example 86

1-(1-Benzyl-1,2,3,4-tetrahydro-isoquinolin-2-yl)-2-(4-methoxyphenyl)ethanone

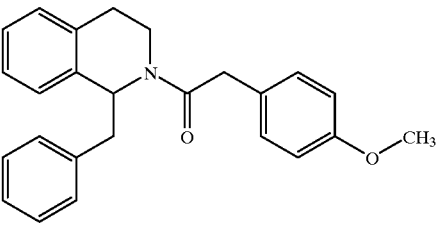

Similarly as described in example 22 using a solution of 1-benzyl-1,2,3,4-tetrahydro-isoquinoline in N,N-dimethylformamide (0.375 M, 0.4 ml, 0.15 mmol), a solution of 4-methoxyphenylacetic acid in N,N-dimethylformamide (0.375 M, 0.4 ml, 0.15 mmol) and 0.25 ml of a suspension of N-(3-dimethylaminopropyl)-N'-ethylcarbodiimide hydrochloride in dichloromethane (1.73 g in 8.3 ml) affords the title compound.

HPLC-MS: $R_t$=15.2 min. m/z: 372 (M+1)

Preparation of 4-(4-nitro-phenyl)-4,5,6,7-tetrahydro-thieno[3,2-c]pyridine trifluoroacetate:

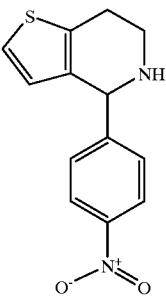

2-(2-Thienyl)-ethylamine (5 g, 39.4 mmol), 4-nitrobenzaldehyde and triethylamine (10 ml) were dissolved in ethanol (100 ml). The reaction mixture was stirred at room temperature for 48 hours. The solid formed was filtered and dried to afford 7.75 g (76%) (4-nitrobenzylidene)-(2-thiophen-2-yl-ethyl)-amine.

M.p.: 83.9–84.4° C.

The above (4-nitrobenzylidene)-(2-thiophen-2-yl-ethyl)-amine (1 g, 3.8 mmol) was added trifluoroacetic acid (100 ml) at once (strongly exothermic reaction). The reaction mixture was stirred at room temperature for 72 hours, then evaporated in vacuo. Crystallisation from a mixture of diethyl ether and dichloromethane afforded 1.2 g (85%) of the title compound.

M.p.: 128–129.5° C.

Preparation of dimethyl-[4-(4,5,6,7-tetrahydro-thieno[3,2-c]pyridin4-yl)-phenyl]-amine:

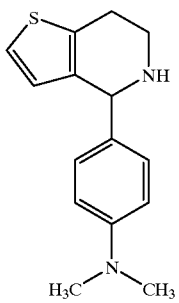

2-(2-Thienyl)-ethylamine (5 g, 39.4 mmol), 4-dimethylaminobenzaldehyde (5.9 g, 94 mmol) triethylamine (6 ml) and ethanol (150 ml) were mixed at room temperature. The reaction mixture was stirred at room temperature for 15 hours. The reaction mixture was concentrated to 75 ml by evaporation in vacuo and the solid formed was filtered and dried to afford 6.82 g (67%) dimethyl-{4-[(2-thiophen-2-yl-ethylimino)-methyl]-phenyl}-amine.

M.p.: 76.8–77° C.

The above dimethyl-{4-[(2-thiophen-2-yl-ethylimino)-methyl]-phenyl}-amine (1 g, 3.9 mmol) was added TFA (20 mL) at once (strongly exothermic reaction). The reaction mixture was stirred at room temperature for 72 hours, then evaporated in vacuo. The crude oil was suspended in dichloromethane (75 ml) and extracted with 1 N hydrochloric acid (50 ml). The aqueous phase was added 2 N sodium hydroxide to pH=10, then extracted with dichloromethane (3×125 ml). The organic phase was dried with MgSO$_4$, filtered, evaporated in vacuo to afford 0.96 g (95%) of the title compound.

M.p.: 95–98° C.

Preparation of 4-phenyl4,5,6,7-tetrahydro-thieno[3,2-c]pyridine:

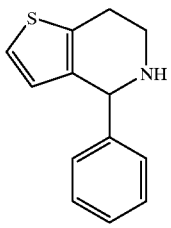

2-(2-Thienyl)-ethylamine (2 g, 15.7 mmol) and benzaldehyde (1.67 g, 15.7 mmol) were dissolved in toluene (50 ml) and the reaction mixture was heated at reflux until 20 ml of toluenid and water was distilled of in a Dean Stark trap. The remaining mixture was evaporated in vacuo to give the crude imine (3.44 g). The crude imine was added trifluoroacetic acid (50 ml) at once (strongly exothermic reaction). The reaction mixture was stirred at room temperature for 72 hours, then evaporated in vacuo. The crude oil was dissolved in dichloromethane (50 ml) and washed with 2 N sodium hydroxide (30 ml). The aqueous phase was extracted with dichloromethane (3×30 ml). The combined organic phases were dried with MgSO$_4$, filtered and evaporated in vacuo. The residue was purified by column chromatography on silica gel eluting with a mixture of dichloromethane and methanol (19:1). This afforded 0.823 g (24%) of the title compound.

M.p.: 79.8–80.7° C.

Preparation of 4-(pyridin-4-yl)4,5,6,7-tetrahydro-thieno[3,2-c]pyridine, NNC 60-0372.

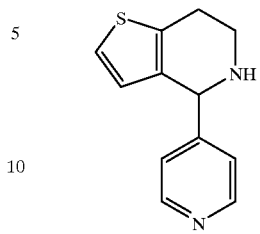

2-(2-Thienyl)-ethylamine (2 g, 15.7 mmol) 4-pyridylaldehyde (1.68 g, 15.7 mmol), triethylamine (1 ml) and ethanol (15 ml) were mixed and the reaction mixture was stirred at room temperature for 15 hours, then evaporated in vacuo. The crude oil was added trifluoroacetic acid (75 m) at once (strongly exothermic reaction). The reaction mixture was stirred at room temperature for 0.5 hour, then evaporated in vacuo. The residue was dissolved in dichloromethane (150 ml) and washed with 2 N sodium hydroxide (100 ml). The aqueous phase was extracted with dichloromethane (3×50 ml). The combined organic phases were dried with MgSO$_4$, filtered and evaporated in vacuo to give an oil (3.21 g) which was crystallised from a mixture of dichloromethane and hexane to afford 2.4 g (71%) of the title compound.

M.p.: 81.8–83.8° C.

Preparation of 1-(4-trifluoromethoxyphenyl)-1,2,3,4-tetrahydro-isoquinoline:

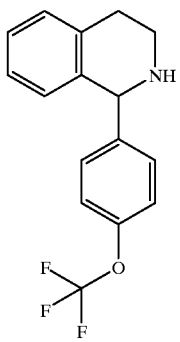

Phenethylamine (0.59 g, 4.9 mmol), 4-trifluoromethoxybenzoic acid (1.0 g, 4.9 mmol) and N-(3-dimethylaminopropyl)-N-ethylcarbodimide, HCl (1.39 g, 7.3 mmol) were mixed in N,N-dimethylformamide (50 mL) at room temperature and the reaction mixture was stirred for 16 hours. Water (50 mL) was added and the mixture was extracted with ethyl acetate (2×50 mL). The combined organic phases were dried (MgSO$_4$), filtered and evaporated in vacuo giving 1.5 g crude product which was purified by column chromatography on silica gel eluting with a mixture of dichloromethane and methanol (9:1). This afforded 0.67 g (45%) of N-phenethyl-4-trifluoromethoxybenzamide.

M.p.: 143.2–143.9° C.

The above N-phenethyl-4-trifluoromethoxybenzamide (0.67 g, 2.2 mmol) was added to a mixture of phosphorous pentoxide (0.92 g, 6.5 mmol) and phosphorous oxychloride (1.03 g, 6.7 mmol) in xylene (50 mL). The reaction mixture was stirred at 140° C. for 16 hours. After cooling, water (50 mL) was added and the mixture was basified with 1 N NaOH. The aqueous phase was extracted with xylene (3×50 mL). The combined organic phases were dried (MgSO₄), filtered and evaporated in vacuo giving 0.96 g crude product which was purified by column chromatography on silica gel eluting with a mixture of dichloromethane and methanol (9:1). This afforded 0.40 g (62%) of 1-(4-Trifluoromethoxy-phenyl)-3,4-dihydro-isoquinoline as an oil.

The above 1-(4-trifluoromethoxyphenyl)-3,4-dihydro-isoquinoline (0.40 g, 1.4 mmol) was dissolved in methanol (20 mL) and sodium borohydride (0.08 g, 2.1 mmol) was added slowly. The reaction mixture was stirred at room temperature for 2.5 hours. The mixture was evaporated in vacuo, redissolved in 1 N NaOH (20 mL) and extracted with dichloromethane (50 mL). The organic phase was dried (MgSO₄), filtered and evaporated in vacuo. The remaining oil (0.35 g) was purified by column chromatography on silica gel eluting with a mixture of dichloromethane and methanol (9:1). This afforded 0.56 g (56%) of the title compound.

M.p.: 56.6–57.1° C.

Example 87

(5-Chlorothiophen-2-yl)-(4-pyridin-4-yl-4,5,6,7-tetrahydro-thieno[3,2-c]pyridin-5-yl)methanone

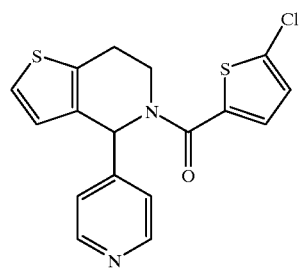

Similarly as described in example 22 using a solution of 4-pyridin-4-yl-4,5,6,7-tetrahydro-thieno [3,2-c]pyridine in N,N-dimethylformamide (0.375 M, 0.4 ml, 0.15 mmol), a solution of 5-chlorothiophene-2-carboxylic acid acid in N,N-dimethylformamide (0.375 M, 0.4 ml, 0.15 mmol) and 0.25 ml of a suspension of N-(3-dimethylaminopropyl)-N'-ethylcarbodiimide hydrochloride in dichloromethane (1.73 g in 8.3 ml) affords the title compound.

HPLC-MS: $R_t$=9.27 min. m/z: 361 (M+1)

Example 88

(5-Chlorothiophen-2-yl)-[4-(4-dimethylaminophenyl)4,5,6,7-tetrahydro-thieno[3,2-c]pyridin-5-yl )-methanone

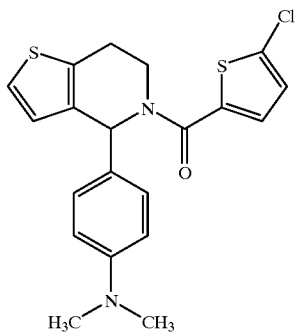

Similarly as described in example 22 using a solution of 4-dimethylaminophenyl)4,5,6,7-tetrahydro-thieno [3,2-c]pyridine in N,N-dimethylformamide (0.375 M, 0.4 ml, 0.15 mmol), a solution of 5-chlorothiophene-2-carboxylic acid in N,N-dimethylformamide (0.375 M, 0.4 ml, 0.15 mmol) and 0.25 ml of a suspension of N-(3-dimethylaminopropyl)-N'-ethylcarbodiimide hydrochloride in dichloromethane (1.73 g in 8.3 ml) affords the title compound.

HPLC-MS: $R_t$=10.70 min. m/z: 403 (M+M)

Example 89

(5-Chlorothiophen-2-yl)-[4-(4-nitrophenyl)-4,5,6,7-tetrahydro-thieno[3,2-c]pyridin-5-yl) methanone

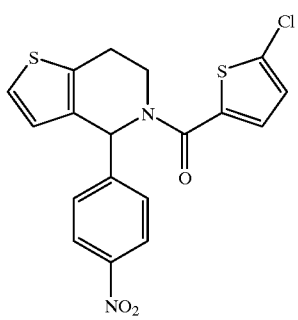

Similarly as described in example 22 using a solution of 4-(4-nitrophenyl)-4,5,6,7-tetrahydro-thieno [3,2-c]pyridine in N,N-dimethylfonmamide (0.375 M, 0.4 ml, 0.15 mmol), a solution of 5-chlorothiophene-2-carboxylic acid in N,N-dimethylformamide (0.375 M, 0.4 ml, 0.15 mmol) and 0.25 ml of a suspension of N-(3-dimethylaminopropyl)-N'-ethylcarbodiimide hydrochloride in dichloromethane (1.73 g in 8.3 ml) affords the title compound.

HPLC-MS: $R_t$=16.18 min. m/z: 405 (M+1)

Example 90

(4-Hydroxymethylphenyl)-(4-phenyl-4,5,6,7-tetrahydro-thieno[3,2-c]pyridin-5-yl)methanone

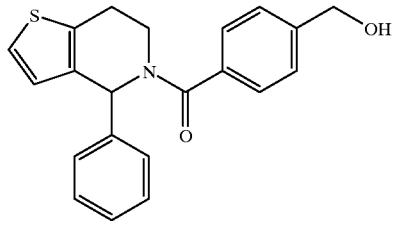

Similarly as described in example 22 using a solution of 4-phenyl-4,5,6,7-tetrahydro-thieno [3,2-c]pyridine in N,N-dimethylformamide (0.375 M, 0.4 ml, 0.15 mmol), a solution of 4-hydroxymethylbenzoic acid in N,N-dimethylformamide (0.375 M, 0.4 ml, 0.15 mmol) and 0.25 ml of a suspension of N-(3-dimethylaminopropyl)-N'-ethylcarbodiimide hydrochloride in dichloromethane (1.73 g in 8.3 ml) affords the title compound.

HPLC-MS: $R_t$=12.33 min. m/z: 350 (M+1)

Example 91

4-(4-Dimethylaminophenyl)-4,5,6,7-tetrahydro-thieno[3,2-c]pyridin-5-yl)-(4-hydroxymethylphenyl)-methanone

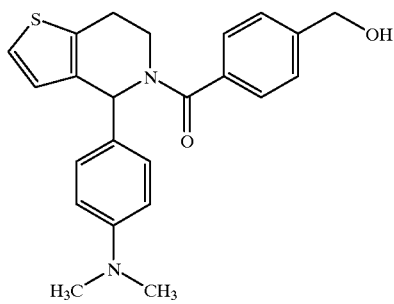

Similarly as described in example 22 using a solution of 4-(4-dimethylaminophenyl)-4,5,6,7-tetrahydro-thieno [3,2-c]pyridine in N,N-dimethylformamide (0.375 M, 0.4 ml, 0.15 mmol), a solution of 4-hydroxymethylbenzoic acid in N,N-dimethylformamide (0.375 M, 0.4 ml, 0.15 mmol) and 0.25 ml of a suspension of N-(3-dimethylaminopropyl)-N'-ethylcarbodiimide hydrochloride in dichloromethane (1.73 g in 8.3 ml) affords the title compound.

HPLC-MS: $R_t$=8.07 min. m/z: 393 (M+1)

Example 92

[4-(4-Nitrophenyl)-4,5,6,7-tetrahydro-thieno[3,2-c]pyridin-5-yl)-(4-hydroxymethylphenyl)-methanone

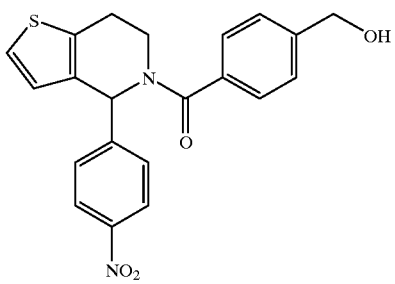

Similarly as described in example 22 using a solution of 4-(4-nitrophenyl)-4,5,6,7-tetrahydro-thieno [3,2-c]pyridine in N,N-dimethylformamide (0.375 M, 0.4 ml, 0.15 mmol), a solution of 4-hydroxymethylbenzoic acid in N,N-dimethylformamide (0.375 M, 0.4 ml, 0.15 mmol) and 0.25 ml of a suspension of N-(3-dimethylaminopropyl)-N'-ethylcarbodiimide hydrochloride in dichloromethane (1.73 g in 8.3 ml) affords the title compound.

HPLC-MS: $R_t$=12.44 min. m/z: 395 (M+1)

Example 93

(4-Chlorophenyl)-(4-phenyl4,5,6,7-tetrahydro-thieno[3,2-c]pyridin-5-yl)methanone

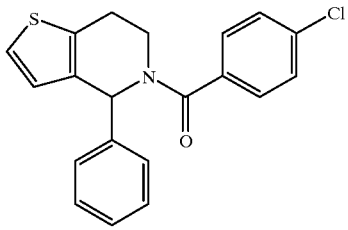

Similarly as described in example 22 using a solution of 4-phenyl4,5,6,7-tetrahydro-thieno [3,2-c]pyridine in N,N-dimethylformamide (0.375 M, 0.4 ml, 0.15 mmol), a solution of 4-chlorobenzoic acid in N,N-dimethylformamide (0.375 M, 0.4 ml, 0.15 mmol) and 0.25 ml of a suspension of N-(3-dimethylaminopropyl)N'-ethylcarbodiimide hydrochloride in dichloromethane (1.73 g in 8.3 ml) affords the title compound.

HPLC-MS: $R_t$=15.90 min. m/z: 355 (M+1)

Example 94

(4-Chlorophenyl)-(4-pyridin-4-yl-4,5,6,7-tetrahydro-thieno[3,2-c]pyridin-5-yl)-methanone

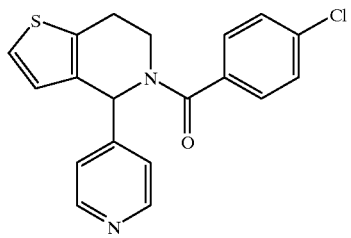

Similarly as described in example 22 using a solution of 4-pyridin4-yl4,5,6,7-tetrahydro-thieno [3,2-c]pyridine in N,N-dimethylformamide (0.375 M, 0.4 ml, 0.15 mmol), a solution of 4-chlorobenzoic acid in N,N-dimethylformamide (0.375 M, 0.4 ml, 0.15 mmol) and 0.25 ml of a suspension of N-(3-dimethylaminopropyl)N'-ethylcarbodiimide hydrochloride in dichloromethane (1.73 g in 8.3 ml) affords the title compound.

HPLC-MS: $R_t$=9.18 min. m/z: 355 (M+1)

Example 95

(4-Chlorophenyl)-[4-(4-dimethylaminophenyl)-4,5,6,7-tetrahydro-thieno [3,2-c]pyridin-5-yl]-methanone

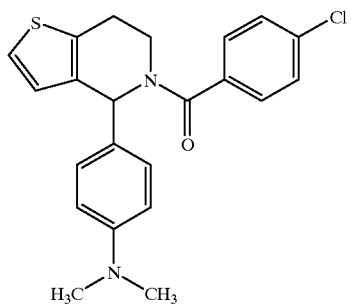

Similarly as described in example 22 using a solution of 4-(4-dimethylaminophenyl)4,5,6,7-tetrahydro-thieno [3,2-c]pyridine in N,N-dimethylformamide (0.375 M, 0.4 ml, 0.15 mmol), a solution of 4-chlorobenzoic acid in N,N-dimethylformamide (0.375 M, 0.4 ml, 0.15 mmol) and 0.25 ml of a suspension of N-(3-dimethylaminopropyl)-N'-ethylcarbodiimide hydrochloride in dichloromethane (1.73 g in 8.3 ml) affords the title compound.

HPLC-MS: $R_t$=10.43 min. m/z: 397 (M+1)

Example 96

(4-Chlorophenyl)-[4-(4-nitrophenyl)4,5,6,7-tetrahydro-thieno[3,2-c]pyridin-5-yl)-methanone

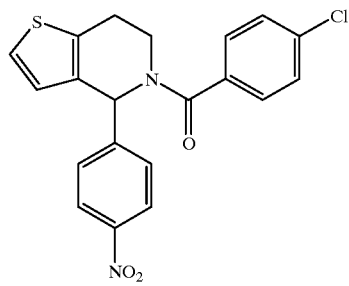

Similarly as described in example 22 using a solution of 4-(4-nitrophenyl)-4,5,6,7-tetrahydro-thieno [3,2-c]pyridine in N,N-dimethylformamide (0.375 M, 0.4 ml, 0.15 mmol), a solution of 4-chlorobenzoic acid in N,N-dimethylformamide (0.375 M, 0.4 ml, 0.15 mmol) and 0.25 ml of a suspension of N-(3-dimethylaminopropyl)-N'-ethylcarbodiimide hydrochloride in dichloromethane (1.73 g in 8.3 ml) affords the title compound.

HPLC-MS: $R_t$=15.81 min. m/z: 399 (M+1)

Example 97

(4-Methoxyphenyl)-[4-phenyl-4,5,6,7-tetrahydro-thieno[3,2-c]pyridin-5-yl)-methanone

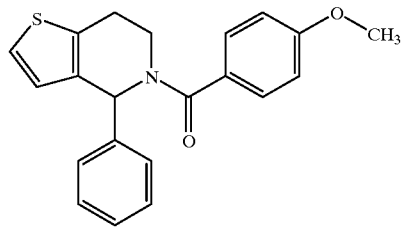

Similarly as described in example 22 using a solution of 4-phenyl-4,5,6,7-tetrahydro-thieno [3,2-c]pyridine in N,N-dimethylformamide (0.375 M, 0.4 ml, 0.15 mmol), a solution of 4-methoxybenzoic acid in N,N-dimethylformamide (0.375 M, 0.4 ml, 0.15 mmol) and 0.25 ml of a suspension of N-(3-dimethylaminopropyl)-N'-ethylcarbodiimide hydrochloride in dichloromethane (1.73 g in 8.3 ml) affords the title compound.

HPLC-MS: $R_t$=14.83 min. m/z: 350 (M+1)

Example 98

(4-Methoxyphenyl)-(4-pyridin-4-yl-4,5,6,7-tetrahydro-thieno[3,2-c]pyridin-5-yl)-methanone

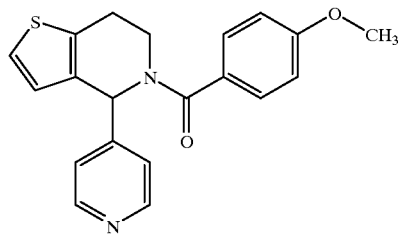

Similarly as described in example 22 using a solution of 4-pyridin4-yl4,5,6,7-tetrahydro-thieno [3,2-c]pyridine in N,N-dimethylformamide (0.375 M, 0.4 ml, 0.15 mmol), a solution of 4-methoxybenzoic acid in N,N-dimethylformamide (0.375 M, 0.4 ml, 0.15 mmol) and 0.25 ml of a suspension of N-(3-dimethylaminopropyl)-N'-ethylcarbodiimide hydrochloride in dichloromethane (1.73 g in 8.3 ml) affords the title compound.

HPLC-MS: $R_t$=8.50 min. m/z: 351 (M+1)

Example 99

[4-(4-Dimethylaminophenyl)-4,5,6,7- tetrahydro-thieno[3,2-c]pyridin-5-yl]-(4-methoxyphenyl)-methanone

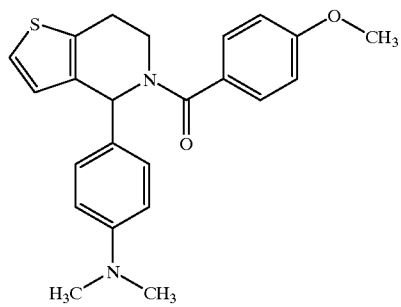

Similarly as described in example 22 using a solution of 4-pyridin4-yl4,5,6,7-tetrahydro-thieno [3,2-c]pyridine in N,N-dimethylformamide (0.375 M, 0.4 ml, 0.15 mmol), a solution of 4-methoxybenzoic acid in N,N-dimethylformamide (0.375 M, 0.4 ml, 0.15 mmol) and 0.25 ml of a suspension of N-(3-dimethylaminopropyl)-N'-ethylcarbodiimide hydrochloride in dichloromethane (1.73 g in 8.3 ml) affords the title compound.

HPLC-MS: $R_t$=9.55 min. m/z: 393 (M+1)

Example 100

[4-(4-Dimethylaminophenyl)-4,5,6,7-tetrahydro-thieno[3,2-c]pyridin-5-yl]-(4-methoxyphenyl)-methanone

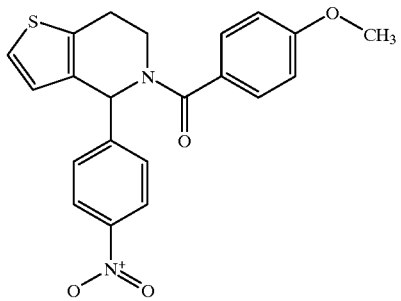

Similarly as described in example 22 using a solution of 4-(4-nitrophenyl)4,5,6,7-tetrahydro-thieno [3,2-c]pyridine in N,N-dimethylformamide (0.375 M, 0.4 ml, 0.15 mmol), a solution of 4-methoxybenzoic acid in N,N-dimethylformamide (0.375 M, 0.4 ml, 0.15 mmol) and 0.25 ml of a suspension of N-(3-dimethylaminopropyl)-N'-ethylcarbodiimide hydrochloride in dichloromethane (1.73 g in 8.3 ml) affords the title compound.

HPLC-MS: $R_t$=14.80 min. m/z: 395 (M+1)

Example 101

3-(4-Methoxyphenyl)--(4-phenyl-4,5,6,7-tetrahydro-thieno[3,2-c]pyridin-5-yl]-propenone

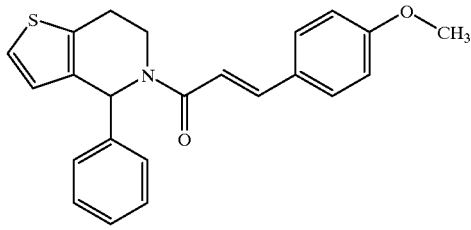

Similarly as described in example 22 using a solution of 4-phenyl-4,5,6,7-tetrahydro-thieno [3,2-c]pyridine in N,N-dimethylformamide (0.375 M, 0.4 ml, 0.15 mmol), a solution of 4-methoxycinnamic acid in N,N-dimethylformamide (0.375 M, 0.4 ml, 0.15 mmol) and 0.25 ml of a suspension of N-(3-dimethylaminopropyl)-N'-ethylcarbodiimide hydrochloride in dichloromethane (1.73 g in 8.3 ml) affords the title compound.

HPLC-MS: $R_t$=15.45 min. m/z: 376 (M+1)

Example 102

(5-Chlorothiophen-2-yl)-(4-phenyl-4,5,6,7-tetrahydro-thieno[3,2-c]pyridin-5-yl)-methanone

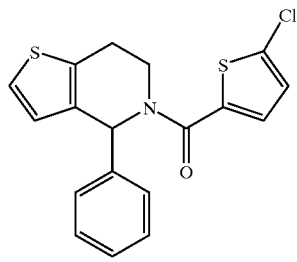

Similarly as described in example 22 using a solution of 4-phenyl-4,5,6,7-tetrahydro-thieno [3,2-c]pyridine in N,N-dimethylformamide (0.375 M, 0.4 ml, 0.15 mmol), a solution of 5-chlorothiophene-2-carboxylic acid in N,N-dimethylformamide (0.375 M, 0.4 ml, 0.15 mmol) and 0.25 ml of a suspension of N-(3-dimethylaminopropyl)-N'-ethylcarbodiimide hydrochloride in dichloromethane (1.73 g in 8.3 ml) affords the title compound.

HPLC-MS: $R_t$=16.42 min. m/z: 360 (M+1)

Example 103

3-(4-Methoxyphenyl)-1-(4-pyridin-4-yl-4,5,6,7-tetrahydro-thieno[3,2-c]pyridin-5-yl)-propenone

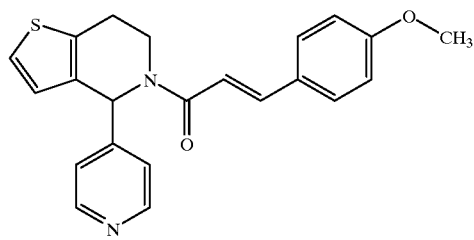

Similarly as described in example 22 using a solution of 4-pyridin-4-yl-4,5,6,7-tetrahydro-thieno [3,2-c]pyridine in N,N-dimethylformamide (0.375 M, 0.4 ml, 0.15 mmol), a solution of 4-methoxycinnamic acid in N,N-dimethylformamide (0.375 M, 0.4 ml, 0.15 mmol) and 0.25 ml of a suspension of N-(3-dimethylaminopropyl)-N'-ethylcarbodiimide hydrochloride in dichloromethane (1.73 g in 8.3 ml) affords the title compound.

HPLC-MS: $R_t$=9.42 min. m/z: 377 (M+1)

Example 104

1-[4-(4-Dimethylaminophenyl)-4,5,6,7-tetrahydro-thieno[3,2-c]pyridin-5-yl)-3-(4-methoxyphenyl)-propenone

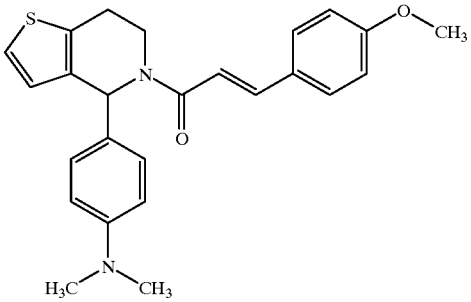

Similarly as described in example 22 using a solution of 4-(4-dimethylaminophenyl)-4,5,6,7-tetrahydro-thieno [3,2-c]pyridine in N,N-dimethylformamide (0.375 M, 0.4 ml, 0.15 mmol), a solution of 4-methoxycinnamic acid in N,N-dimethylformamide (0.375 M, 0.4 ml, 0.15 mmol) and 0.25 ml of a suspension of N-(3-dimethylaminopropyl)-N'-ethylcarbodiimide hydrochloride in dichloromethane (1.73 g in 8.3 ml) affords the title compound.

HPLC-MS: 10.32 min. m/z: 418 (M+1)

Example 105

3-(4-Methoxyphenyl)-1-(4-(4-nitrophenyl)4,5,6,7-tetrahydro-thieno[3,2-c]pyridin-5-yl)-5 propenone

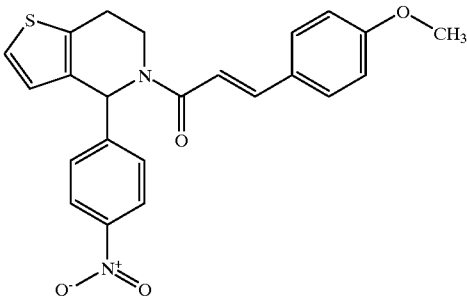

Similarly as described in example 22 using a solution of 4-(4-nitrophenyl)4,5,6,7-tetrahydro-thieno [3,2-c]pyridine in N,N-dimethylformamide (0.375 M, 0.4 ml, 0.15 mmol), a solution of 4-methoxycinnamic acid in N,N-dimethylformamide (0.375 M, 0.4 ml, 0.15 mmol) and 0.25 ml of a suspension of N-(3-dimethylaminopropyl)-N'-ethylcarbodiimide hydrochloride in dichloromethane (1.73 g in 8.3 ml) affords the title compound.

HPLC-MS: $R_t$=15.47 min. m/z: 421 (M+1)

Example 106

(4-Dimethylaminophenyl)-(4-phenyl-4,5,6,7-tetrahydro-thieno[3,2-c]pyridin-5-yl)-methanone

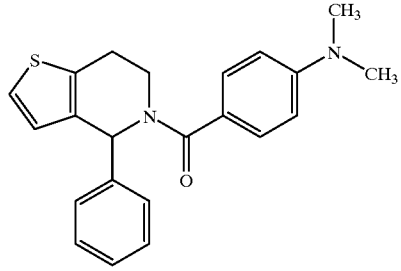

Similarly as described in example 22 using a solution of 4-phenyl-4,5,6,7-tetrahydro-thieno [3,2-c]pyridine in N,N-dimethylformamide (0.375 M, 0.4 ml, 0.15 mmol), a solution of 4-dimethylaminobenzoic acid in N,N-dimethylformamide (0.375 M, 0.4 ml, 0.15 mmol) and 0.25 ml of a suspension of N-(3-dimethylaminopropyl)-N'-ethylcarbodiimide hydrochloride in dichloromethane (1.73 g in 8.3 ml) affords the title compound.

HPLC-MS: $R_t$=11.83 min. m/z: 363 (M+1)

Example 107

(4-Dimethylaminophenyl)-(4-pyridin-4-yl-4,5,6,7-tetrahydro-thieno[3,2-c]pyridin-5-yl)-methanone

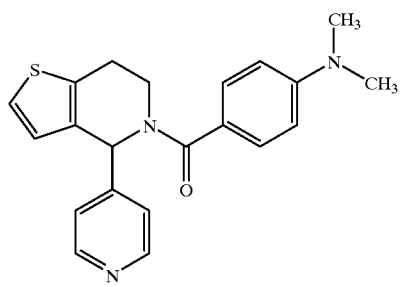

Similarly as described in example 22 using a solution of 4-pyridin4-yl4,5,6,7-tetrahydro-thieno [3,2-c]pyridine in N,N-dimethylformamide (0.375 M, 0.4 ml, 0.15 mmol), a solution of 4-dimethylaminobenzoic acid in N,N-dimethylformamide (0.375 M, 0.4 ml, 0.15 mmol) and 0.25 ml of a suspension of N-(3-dimethylaminopropyl)-N'-ethylcarbodiimide hydrochloride in dichloromethane (1.73 g in 8.3 ml) affords the title compound.

HPLC-MS: $R_t$=7.5 min. m/z: 364 (M+1)

Example 108

(4-Dimethylaminophenyl)-[4-(4-dimethylaminophenyl)-4,5,6,7-tetrahydro-thieno[3,2-c]pyridin-5 -yl]-methanone

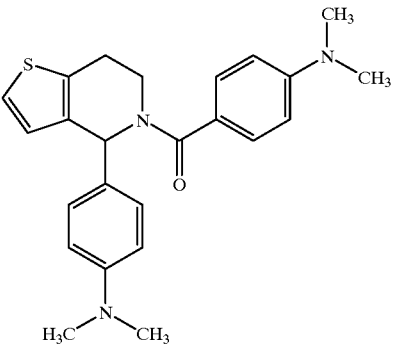

Similarly as described in example 22 using a solution of 4-(4-dimethylaminophenyl)4,5,6,7-tetrahydro-thieno [3,2-c]pyridine in N,N-dimethylformamide (0.375 M, 0.4 ml, 0.15 mmol), a solution of 4-dimethylaminobenzoic acid in N,N-dimethylformamide (0.375 M, 0.4 ml, 0.15 mmol) and 0.25 ml of a suspension of N-(3-dimethylaminopropyl)-N'-ethylcarbodiimide hydrochloride in dichloromethane (1.73 g in 8.3 ml) affords the title compound.

HPLC-MS: $R_t$=8.15 min. m/z: 406 (M+1)

Example 109

(4-Dimethylaminophenyl)-[4-(4-nitrophenyl)4,5,6,7-tetrahydro-thieno[3,2-c]pyridin-5-yl]-methanone

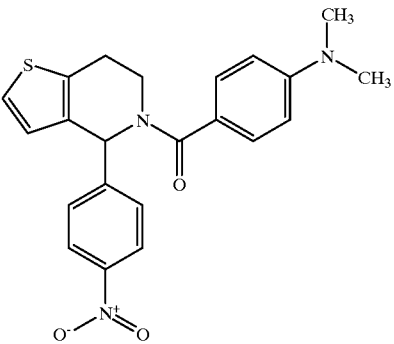

Similarly as described in example 22 using a solution of 4-(4-nitrophenyl)4,5,6,7-tetrahydro-thieno [3,2-c]pyridine in N,N-dimethylformamide (0.375 M, 0.4 ml, 0.15 mmol), a solution of 4.-dimethylaminobenzoic acid in N,N-dimethylformamide (0.375 M, 0.4 ml, 0.15 mmol) and 0.25 ml of a suspension of N-(3-dimethylaminopropyl)-N'-ethylcarbodiimide hydrochloride in dichloromethane (1.73 g in 8.3 ml) affords the title compound.

HPLC-MS: $R_t$=12.68 min. m/z: 408 (M+1)

Example 110

(1H-Benzoimidazol-5-yl)-(4-phenyl-4,5,6,7-tetrahydro-thieno[3,2-c]pyridin-5-yl)-methanone

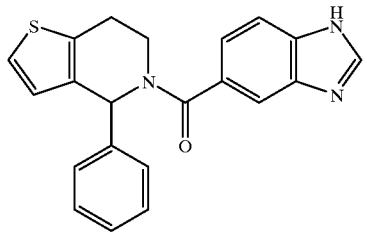

Similarly as described in example 22 using a solution of 4-phenyl4,5,6,7-tetrahydro-thieno [3,2-c]pyridine in N,N-dimethylformamide (0.375 M, 0.4 ml, 0.15 mmol), a solution of benzimidazole-5-carboxylic acid in N,N-dimethylformamide (0.375 M, 0.4 ml, 0.15 mmol) and 0.25 ml of a suspension of N-(3-dimethylaminopropyl)-N'-ethylcarbodiimide hydrochloride in dichloromethane (1.73 g in 8.3 ml) affords the title compound.

HPLC-MS: $R_t$=9.27 min. m/z: 360 (M+1)

Example 111

(1H-Benzoimidazol-5-yl)-(4-phenyl-4,5,6,7-tetrahydro-thieno[3,2-c]pyridin-5-yl)-methanone

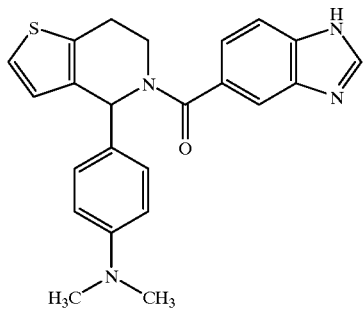

Similarly as described in example 22 using a solution of 4-(4-dimethylaminophenyl)-4,5,6,7-tetrahydro-thieno [3,2-c]pyridine in N,N-dimethylformamide (0.375 M, 0.4 ml, 0.15 mmol), a solution of benzimidazole-5-carboxylic acid in N,N-dimethylformamide (0.375 M, 0.4 ml, 0.15 mmol) and 0.25 ml of a suspension of N-(3-dimethylaminopropyl)-N'-ethylcarbodiimide hydrochloride in dichloromethane (1.73 g in 8.3 ml) affords the title compound.

HPLC-MS: $R_t$=7.17 min. m/z: 403 (M+1)

Example 112

(1H-Benzoimidazol-5-yl)-[4-(4-nitrophenyl)-4,5,6,7-tetrahydro-thieno[3,2-c]pyridin-5-yl]-methanone

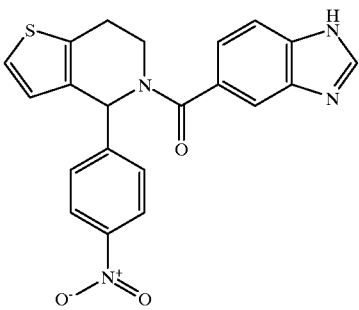

Similarly as described in example 22 using a solution of 4-(4-nitrophenyl)-4,5,6,7-tetrahydro-thieno [3,2-c]pyridine in N,N-dimethylformamide (0.375 M, 0.4 ml, 0.15 mmol), a solution of benzimidazole-5-carboxylic acid in N,N-dimethylformamide (0.375 M, 0.4 ml, 0.15 mmol) and 0.25 ml of a suspension of N-(3-dimethylaminopropyl)-N'-ethylcarbodiimide hydrochloride in dichloromethane (1.73 g in 8.3 ml) affords the title compound.

HPLC-MS: $R_t$=9.50 min. m/z: 405 (M+1)

Example 113

(4-Fluorophenyl)-(4-phenyl-4,5,6,7-tetrahydro-thieno[3,2-c]pyridin-5-yl)-methanone

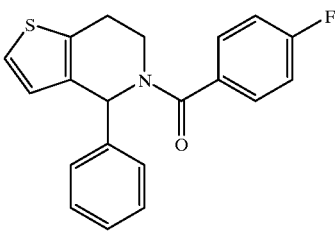

Similarly as described in example 22 using a solution of 4-phenyl4,5,6,7-tetrahydro-thieno [3,2-c]pyridine in N,N-dimethylformamide (0.375 M, 0.4 ml, 0.15 mmol), a solution of 4-fluorobenzoic acid in N,N-dimethylformamide (0.375 M, 0.4 ml, 0.15 mmol) and 0.25 ml of a suspension of N-(3-dimethylaminopropyl)N'-ethylcarbodiimide hydrochloride in dichloromethane (1.73 g in 8.3 ml) affords the title compound.

HPLC-MS: $R_t$=15.07 min. m/z: 339 (M+1)

Example 114

(4-Fluorophenyl)-(4-pyridin-4-yl-4,5,6,7-tetrahydro-thieno[3,2-c]pyridin-5-yl)-methanone

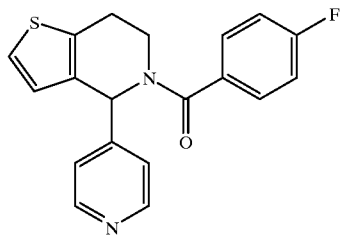

Similarly as described in example 22 using a solution of 4-pyridin-4-yl-4,5,6,7-tetrahydro-thieno [3,2-c]pyridine in N,N-dimethylformamide (0.375 M, 0.4 ml, 0.15 mmol), a solution of 1-fluorobenzoic acid in N,N-dimethylformamide (0.375 M, 0.4 ml, 0.15 mmol) and 0.25 ml of a suspension of N-(3-dimethylaminopropyl)-N'-ethylcarbodiimide hydrochloride in dichloromethane (1.73 g in 8.3 ml) affords the title compound.

HPLC-MS: $R_t$=8.62 min. m/z: 339 (M+1)

Example 115

4-(4-Dimethylaminophenyl)4,5,6,7-tetrahydro-thieno[3,2-c]pyridin-5-yl]-(4-fluorophenyl)-methanone

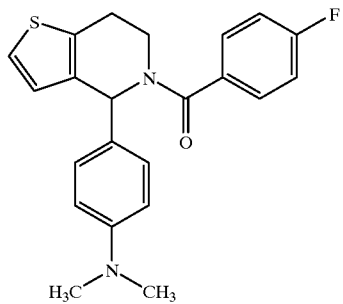

Similarly as described in example 22 using a solution of 4-(4-dimethylaminophenyl)4,5,6,7-tetrahydro-thieno [3,2-c]pyridine in N,N-dimethylformamide (0.375 M, 0.4 ml, 0.15 mmol), a solution of 4-fluorobenzoic acid in N,N-dimethylformamide (0.375 M, 0.4 ml, 0.15 mmol) and 0.25 ml of a suspension of N-(3-dimethylaminopropyl)-N'-ethylcarbodiimide hydrochloride in dichloromethane (1.73 g in 8.3 ml) affords the title compound.

HPLC-MS: $R_t$=9.68 min. m/z: 381 (M+1)

Example 116

(4-Fluorophenyl)-[4-(4-nitrophenyl)4,5,6,7-tetrahydro-thieno[3,2-c]pyridin-5-yl]-methanone

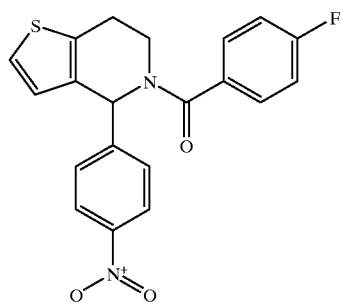

Similarly as described in example 22 using a solution of 4-(4-nitrophenyl)4,5,6,7-tetrahydro-thieno [3,2-c]pyridine in N,N-dimethylformamide (0.375 M, 0.4 ml, 0.15 mmol), a solution of 4-fluorobenzoic acid in N,N-dimethylformamide (0.375 M, 0.4 ml, 0.15 mmol) and 0.25 ml of a suspension of N-(3-dimethylaminopropyl)-N'-ethylcarbodiimide hydrochloride in dichloromethane (1.73 g in 8.3 ml) affords the title compound.

HPLC-MS: $R_t$=14.95 min. m/z: 383 (M+1)

Example 117

(4-Bromophenyl)-(4-phenyl-4,5,6,7-tetrahydro-thieno[3,2-c]pyridin-5-yl)-methanone

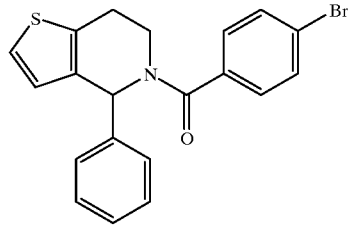

Similarly as described in example 22 using a solution of 4-phenyl4,5,6,7-tetrahydro-thieno [3,2-c]pyridine in N,N-dimethylformamide (0.375 M, 0.4 ml, 0.15 mmol), a solution of 4-bromobenzoic acid in N,N-dimethylformamide (0.375 M, 0.4 ml, 0.15 mmol) and 0.25 ml of a suspension of N-(3-dimethylaminopropyl)-N'-ethylcarbodiimide hydrochloride in dichloromethane (1.73 g in 8.3 ml) affords the title compound.

HPLC-MS: $R_t$=16.07 min. m/z: 398+400 (M+1)

Example 118

(4-Bromophenyl)-(4-pyridin-4-yl-4,5,6,7-tetrahydro-thieno[3,2-c]pyridin-5-yl)-methanone

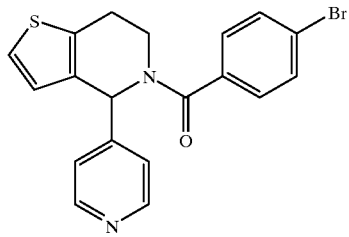

Similarly as described in example 22 using a solution of 4-pyridin-4-yl-4,5,6,7-tetrahydro-thieno [3,2-c]pyridine in N,N-dimethylformamide (0.375 M, 0.4 ml, 0.15 mmol), a solution of 4-bromobenzoic acid in N,N-dimethylformamide (0.375 M, 0.4 ml, 0.15 mmol) and 0.25 ml of a suspension of N-(3-dimethylaminopropyl)-N'-ethylcarbodiimide hydrochloride in dichloromethane (1.73 g in 8.3 ml) affords the title compound.

HPLC-MS: 9.30 min. m/z: 399+401 (M+1)

Example 119

(4-Bromophenyl) -(4-dimethylaminophenyl)4,5,6,7-tetrahydro-thieno [3,2-c]pyridin-5-yl]-methanone

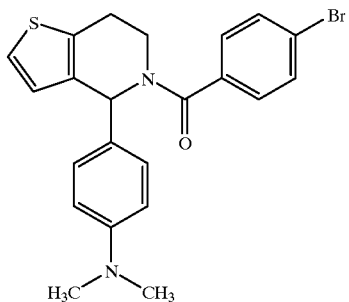

Similarly as described in example 22 using a solution of 4-(4-dimethylaminophenyl)4,5,6,7-tetrahydro-thieno [3,2-c]pyridine in N,N-dimethylformamide (0.375 M, 0.4 ml, 0.15 mmol), a solution of 4-bromobenzoic acid in N,N-dimethylformamide (0.375 M, 0.4 ml, 0.15 mmol) and 0.25 ml of a suspension of N-(3-dimethylaminopropyl)-N'-ethylcarbodiimide hydrochloride in dichloromethane (1.73 g in 8.3 ml) affords the title compound.

HPLC-MS: $R_t$=10.72 min. m/z: 441+443 (M+1)

Example 120

(4-Bromophenyl)-[4-(4-nitrophenyl)-4,5,6,7-tetrahydro-thieno[3,2-c]pyridin-5-yl)-methanone

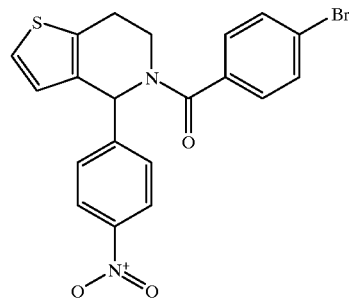

Similarly as described in example 22 using a solution of 4-(4-nitrophenyl)4,5,6,7-tetrahydro-thieno [3,2-c]pyridine in N,N-dimethylformamide (0.375 M, 0.4 ml, 0.15 mmol), a solution of 4-bromobenzoic acid in N,N-dimethylformamide (0.375 M, 0.4 ml, 0.15 mmol) and 0.25 ml of a suspension of N-(3-dimethylaminopropyl)-N'-ethylcarbodiimide hydrochloride in dichloromethane (1.73 g in 8.3 ml) affords the title compound.

HPLC-MS: 15.84 min. m/z: 442+444 (M+1)

Example 121 b 3-Furan-3-yl-1-(4-phenyl-4,5,6,7-tetrahydro-thieno[3,2-c]pyridin-5-yl)-propenone

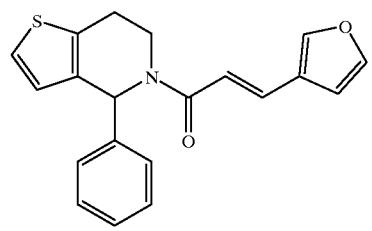

Similarly as described in example 22 using a solution of 4-phenyl4,5,6,7-tetrahydro-thieno [3,2-c]pyridine in N,N-dimethylformamide (0.375 M, 0.4 ml, 0.15 mmol), a solution of 3-furan-3 -ylacrylic acid in N,N-dimethylformamide (0.375 M, 0.4 ml, 0.15 mmol) and 0.25 ml of a suspension of N-(3-dimethylaminopropyl)-N'-ethylcarbodiimide hydrochloride in dichloromethane (1.73 g in 8.3 ml) affords the title compound.

HPLC-MS: 14.77 min. m/z: 336 (M+1)

Example 122

3-(3-Furan-3-yl)-1-(4-pyridin-4-yl-4,5,6,7-tetrahydro-thieno[3,2-c]pyridin-5-yl)-propenone

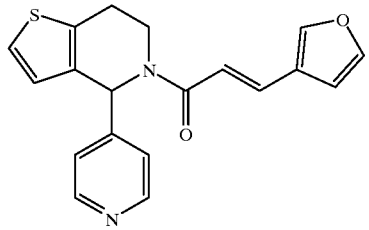

Similarly as described in example 22 using a solution of 4-pyridin-4-yl-4,5,6,7-tetrahydro-thieno [3,2-c]pyridine in N,N-dimethylformamide (0.375 M, 0.4 ml, 0.15 mmol), a solution of 3-furan-3-ylacrylic acid in N,N-dimethylformamide (0.375 M, 0.4 ml, 0.15 mmol) and 0.25 ml of a suspension of N-(3-dimethylaminopropyl)-N'-ethylcarbodiimide hydrochloride in dichloromethane (1.73 g in 8.3 ml) affords the title compound.

HPLC-MS: $R_t$=8.58 min. m/z: 337 (M+1)

Example 123

1-[4-(4-Dimethylaminophenyl)-4,5,6,7-tetrahydro-thieno[3,2-c]pyridin-5-yl)-3-(3-furan-3-yl)-propenone

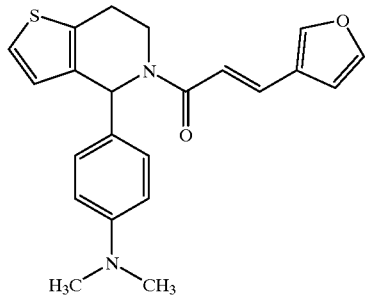

Similarly as described in example 22 using a solution of 4-(4-dimethylaminophenyl)-4,5,6,7-tetrahydro-thieno [3,2-c]pyridine in N,N-dimethylformamide (0.375 M, 0.4 ml, 0.15 mmol), a solution of 3-furan-3-ylacrylic acid in N,N-dimethylformamide (0.375 M, 0.4 ml, 0.15 mmol) and 0.25 ml of a suspension of N-(3-dimethylaminopropyl)-N'-ethylcarbodiimide hydrochloride in dichloromethane (1.73 g in 8.3 ml) affords the title compound.

HPLC-MS: $R_t$=9.38 min. m/z: 379 (M+1)

Example 124

3-(3-Furan-3-yl)-1-[4-(4-nitrophenyl)-4,5,6,7-tetrahydro-thieno[3,2-c]pyridin-5-yl)-propenone

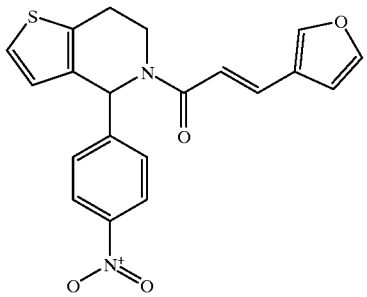

Similarly as described in example 22 using a solution of 4-(4-nitrophenyl)-4,5,6,7-tetrahydro-thieno [3,2-c]pyridine in N,N-dimethylformamide (0.375 M, 0.4 ml, 0.15 mmol), a solution of 3-furan-3 -ylacrylic acid in N,N-dimethylformamide (0.375 M, 0.4 ml, 0.15 mmol) and 0.25 ml of a suspension of N-(3-dimethylaminopropyl)-N'-ethylcarbodiimide hydrochloride in dichloromethane (1.73 g in 8.3 ml) affords the title compound.

HPLC-MS: $R_t$=14.57 min. m/z: 381 (M+1)

Example 125

[4-(4-Chlorophenyl)-4,5,6,7-tetrahydro-thieno[3,2-c]pyridin-5-yl]-(4-hydroxyphenyl)-methanone, less polar enantiomer,

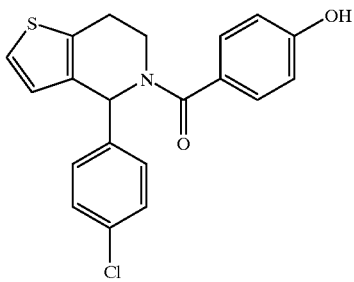

[4-(4-Chlorophenyl)4,5,6,7-tetrahydro-thieno[3,2-c]pyridin-5-yl]-(4-hydroxyphenyl)-methanone (21 mg) was dissolved in a 1:1:1 mixture of ethyl acetate, 2-propanol and n-heptane (3 ml) and fractionated by HPLC using a 21.1× 250 mm (R,R)-Whelk-O column (Regis). The column was eluted isocratically with a mixture of n-heptane and 2-propanol (1:1) at a flow rate of 10 ml/min and fractions were collected corresponding to 1 min/fraction. The eluting enantiomers were detected spectroscopically by measuring absorbance at a wavelength of 225 nm. Two eluting peaks were detected, corresponding to $T_R$ 24–29 minutes and $T_R$ 42–50 minutes, respectively. Fractions corresponding to $T_R$ 24–29 minutes were pooled and evaporated to yield 8.8 mg of the title compound.

100% ee (Determined by HPLC using a 4.6×250 mm (R,R)-Whelk-O column eluted with n-heptane: 2-propanol (1:1), the flow rate was 1 ml/min, eluting sample was monitored spectroscopically at 225 and 280 nm, $T_R$ 8.9 min).

Example 126

[4-(4-Chlorophenyl)-4,5,6,7-tetrahydro-thieno[3,2-c]pyridin-5-yl]-(4-hydroxyphenyl)-methanone, more polar enantiomer,

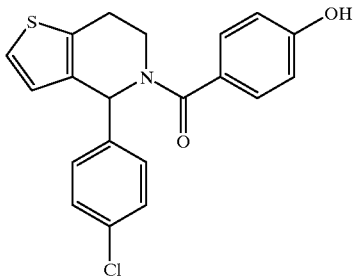

Fractions from example 125 corresponding to $T_R$ 42–50 minutes were pooled and evaporated to yield 9.1 mg of the title compound.

99.4% ee (Conditions as described in example 125, $T_R$ 12.5 min).

Example 127

(1 H-Benzoimidazol-5-yl)-[4-(4-trifluoromethoxyphenyl)-4,5,6,7-tetrahydro-thieno[3,2-c]pyridin-5-yl]methanone, less polar enantiomer,

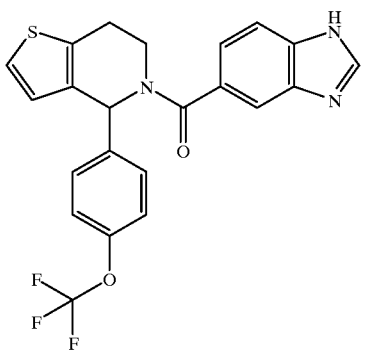

(1 H-Benzoimidazol-5-yl)[4-(4-trifluoromethoxyphenyl)4,5,6,7-tetrahydro-thieno[3,2-c]pyridin-5-yl]methanone (15 mg) was dissolved in a 1:1 mixture of n-heptane:2-propanol (2 ml) and fractionated by HPLC using a 20×250 mm Chiralpak AS column. The column was eluted isocratically with a mixture of n-heptane, ethanol and diethylamine (70:30:0.1) at a flow rate of 6 m/min and fractions collected corresponding to 1 min/fraction. The eluting enantiomers were detected spectroscopically by measuring absorbance at a wavelength of 225 nm. Two eluting peaks were detected, corresponding to $T_R$ 16–19 minutes and $T_R$ 27–35 minutes, respectively. Fractions corresponding to $T_R$ 16–19 minutes were pooled and evaporated to yield 7.2 mg of the title compound.

100% ee (Determined by HPLC using a 4.6×250 mm Chiralpak AS column eluted with a mixture of n-heptane, ethanol and diethylamine (70:30:0.07), the flow rate was 0.6 ml/min, eluting sample was monitored spectroscopically at 225 and 245 nm, $T_R$ 8.4 min).

Example 128

(1 H-Benzoimidazol-5-yl)-[4-(4-trifluoromethoxyphenyl)-4,5,6,7-tetrahydro-thieno[3,2-c]pyridin-5-yl]methanone, more polar enantiomer,

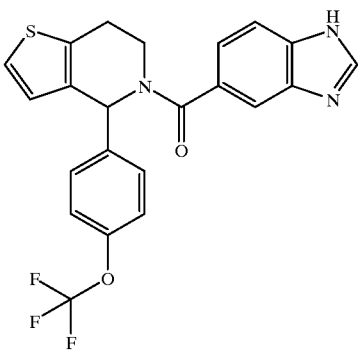

Fractions from example 127 corresponding to $T_R$ 27–35 minutes were pooled and evaporated to yield 8.0 mg of the title compound.

>99% ee (Conditions as described in example 127, $T_R$ 14.7 min).

Example 129

(5-Chlorothiophen-2-yl)-[1-(4-trifluoromethoxyphenyl)-1,2,3,4-tetrahydroisoquinolin-2-yl-methanone

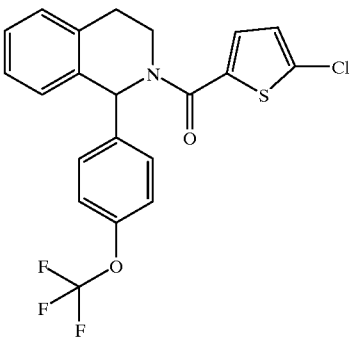

Similarly as described in example 22 using a solution of 1-(4-trifluoromethoxyphenyl)-1,2,3,4-tetrahydroisoquinoline in N,N-dimethylformamide (0.375 M, 0.4 ml, 0.15 mmol), a solution of 5-chlorothiophene-2-carboxylic acid in N,N-dimethylformamide (0.375 M, 0.4 ml, 0.15 mmol) and 0.25 ml of a suspension of N-(3-dimethylaminopropyl)-N'-ethylcarbodiimide hydrochloride in dichloromethane (1.73 g in 8.3 ml) affords the title compound.

HPLC-MS: $R_t$=17.75 min. m/z: 438 (M+1)

Example 130

(4-Chlorophenyl)-[1-(4-trifluoromethoxyphenyl)-1,2,3,4-tetrahydroisoquinolin-2-yl]-methanone

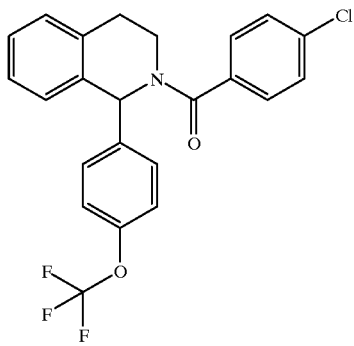

Similarly as described in example 22 using a solution of 1-(4-trifluoromethoxyphenyl)-1,2,3,4-tetrahydroisoquinoline in N,N-dimethylformamide (0.375 M, 0.4 ml, 0.15 mmol), a solution of 4-chlorobenzoic acid in N,N-dimethylformamide (0.375 M, 0.4 ml, 0.15 mmol) and 0.25 ml of a suspension of N-(3-dimethylaminopropyl)-N'-ethylcarbodiimide hydrochloride in dichloromethane (1.73 g in 8.3 ml) affords the title compound.

HPLC-MS: $R_t$ 17.42 min. m/z: 432 (M+1)

Example 131

(4-Methoxyphenyl)-[1-(4-trifluoromethoxyphenyl)-1,2,3,4-tetrahydroisoquinolin-2-yl]-methanone

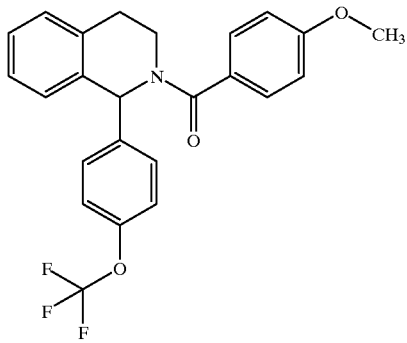

Similarly as described in example 22 using a solution of 1-(4-trifluoromethoxyphenyl)-1,2,3,4-5 tetrahydroisoquinoline in N,N-dimethylformamide (0.375 M, 0.4 ml, 0.15 mmol), a solution of 4-methoxybenzoic acid in N,N-dimethylformamide (0.375 M, 0.4 ml, 0.15 mmol) and 0.25 ml of a suspension of N-(3-dimethylaminopropyl)-N'-ethylcarbodiimide hydrochloride in dichloromethane (1.73 g in 8.3 ml) affords the title compound.

HPLC-MS: RP=16.42 min. m/z: 428 (M+1)

Example 132

3-(4-Methoxyphenyl)-1-[1-(4-trifluoromethoxyphenyl)-1,2,3,4-tetrahydroisoquinolin-2-yl]propenone

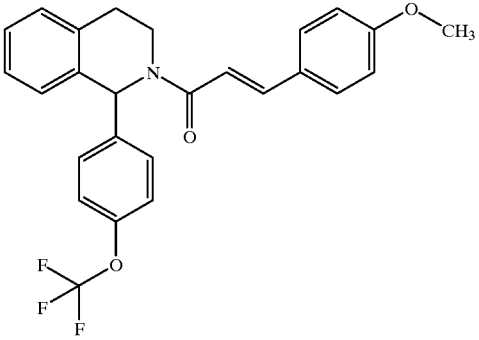

Similarly as described in example 22 using a solution of 1-(4-trifluoromethoxyphenyl)-1,2,3,4-tetrahydroisoquinoline in N,N-dimethylformamide (0.375 M, 0.4 ml, 0.15 mmol), a solution of 4-methoxycinnamic acid in N,N-dimethylformamide (0.375 M, 0.4 ml, 0.15 mmol) and 0.25 ml of a suspension of N-(3-dimethylaminopropyl)N'-ethylcarbodiimide hydrochloride in dichloromethane (1.73 g in 8.3 ml) affords the title compound.

HPLC-MS: $R_t$=17.02 min. m/z: 454 (M+1)

Example 133

3-Furan-3-yl-1-[1-(4-trifluoromethoxyphenyl)-1,2,3,4-tetrahydroisoquinolin-2-yl]propenone Similarly as described in example 22 using a solution of 1-(4-trifluoromethoxyphenyl)-1,2,3,4-tetrahydroisoquinoline in N,N-dimethylformamide (0.375 M, 0.4 ml, 0.15 mmol), a solution of 3-furan-3-ylacrylic acid in N,N-dimethylformamide (0.375 M, 0.4 ml, 0.15 mmol) and 0.25 ml of a suspension of N-(3-dimethylaminopropyl)-N'-ethylcarbodiimide hydrochloride in dichloromethane (1.73 g in 8.3 ml) affords the title compound.

HPLC-MS: $R_t$=16.12 min. m/z: 414 (M+1)

Example 134

(4-Trifluoromethoxyphenyl)-[4-(4-trifluoromethylphenyl)-4,5,6,7-tetrahydro-thieno[3,2-c]pyridin-5-yl]methanone

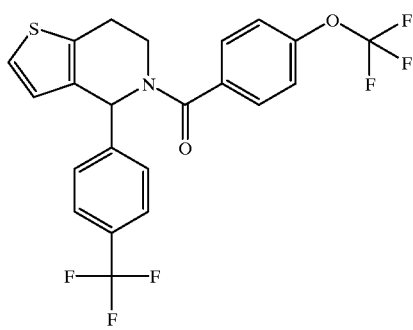

Similarly as described in example 22 using a solution of 4-(4-trifluoromethylphenyl)-4,5,6,7-tetrahydro-thieno [3,2-c]pyridine in N,N-dimethylformamide (0.375 M, 0.4 ml, 0.15 mmol), a solution of 4-trifluoromethoxybenzoic acid in N,N-dimethylformamide (0.375 M, 0.4 ml, 0.15 mmol) and 0.25 ml of a suspension of N-(3-dimethylaminopropyl)-N'-ethylcarbodiimide hydrochloride in dichloromethane (1.73 g in 8.3 ml) affords the title compound.

HPLC-MS: $R_t$=17.01 min. m/z: 472 (M+1)

Example 135

(7-Methoxybenzofuran-2-yl)-[4-(4-trifluromethylphenyl)-4,5,6,7- tetrahydro-thieno[3,2-c]pyridin-5-yl]methanone

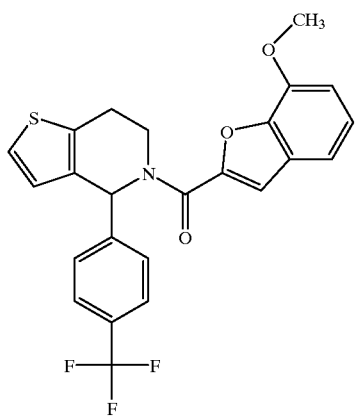

Similarly as described in example 22 using a solution of 4-(4-trifluoromethylphenyl)-4,5,6,7-tetrahydro-thieno [3,2-c]pyridine in N,N-dimethylformamide (0.375 M, 0.4 ml, 0.15 mmol), a solution of 7-methoxybenzofuran-2-carboxylic acid in N,N-dimethylformamide (0.375 M, 0.4 ml, 0.15 mmol) and 0.25 ml of a suspension of N-(3-dimethylaminopropyl)-N'-ethylcarbodiimide hydrochloride in dichloromethane (1.73 g in 8.3 ml) affords the title compound.

HPLC-MS: $R_t$=16.98 min. m/z: 458 (M+1)

Example 136

Benzofuran-2-yl-[4-(4-trifluoromethylphenyl)-4,5,6,7-tetrahydro-thieno[3,2-c]pyridin-5-yl]methanone

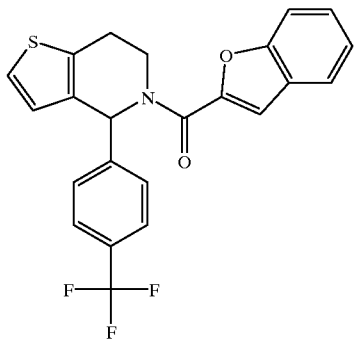

Similarly as described in example 22 using a solution of 4-(4-trifluoromethylphenyl)-4,5,6,7-tetrahydro-thieno [3,2-c]pyridine in N,N-dimethylformamide (0.375 M, 0.4 ml, 0.15 mmol), a solution of benzofuran-2-carboxylic acid in N,N-dimethylformamide (0.375 M, 0.4 ml, 0.15 mmol) and 0.25 ml of a suspension of N-(3-dimethylaminopropyl)-N'-ethylcarbodiimide hydrochloride in dichloromethane (1.73 g in 8.3 ml) affords the title compound.

HPLC-MS: $R_t$17.01 min. m/z: 428 (M+1)

Example 137

3-(4-Fluorophenyl)-1-[4-(4-trifluoromethylphenyl)-4,5,6,7-tetrahydro-thieno[3,2-c]pyridin-5-yl]-propenone

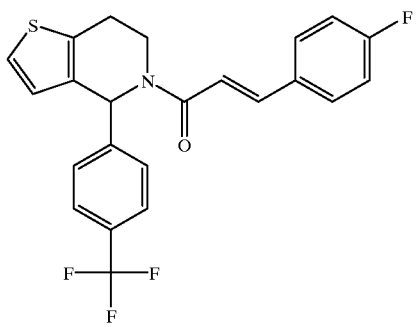

Similarly as described in example 22 using a solution of 4-(4-trifluoromethylphenyl)-4,5,6,7-tetrahydro-thieno [3,2-c]pyridine in N,N-dimethylformamide (0.375 M, 0.4 ml, 0.15 mmol), a solution of 4-fluorocinnamic acid in N,N-dimethylformamide (0.375 M, 0.4 ml, 0.15 mmol) and 0.25 ml of a suspension of N-(3-dimethylaminopropyl)-N'-ethylcarbodiimide hydrochloride in dichloromethane (1.73 g in 8.3 ml) affords the title compound.

HPLC-MS: $R_t$=16.58 min. m/z: 432 (M+1)

Example 138

3-(4-Trifluoromethylphenyl)-1-[4-(4-trifluoromethylphenyl)-4,5,6,7-tetrahydro-thieno[3,2-c]pyridin-5-yl]propenone

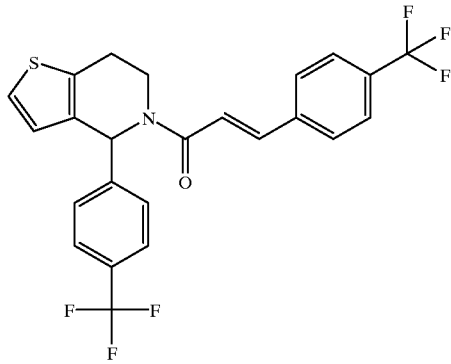

Similarly as described in example 22 using a solution of 4-(4-trifluoromethylphenyl)4,5,6,7-tetrahydro-thieno [3,2-c]pyridine in N,N-dimethylformamide (0.375 M, 0.4 ml, 0.15 mmol), a solution of 4-trifluoromethylcinnamic acid in N,N-dimethylformamide (0.375 M, 0.4 ml, 0.15 mmol) and 0.25 ml of a suspension of N-(3dimethylaminopropyl)-N'-ethylcarbodiimide hydrochloride in dichloromethane (1.73 g in 8.3 ml) affords the title compound.

HPLC-MS: $R_t$=17.38 min. m/z: 482 (M+1)

Example 139

3-(3-Methoxyphenyl)-1-[4-(4-trifluoromethylphenyl) 4,5,6,7-tetrahydro-thieno [3,2-c]pyridin-5-yl] propenone

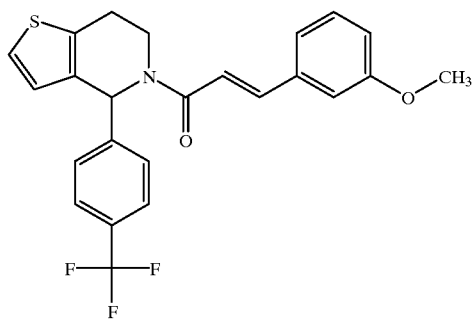

Similarly as described in example 22 using a solution of 4-(4-trifluoromethylphenyl)4,5,6,7-tetrahydro-thieno [3,2-c]pyridine in N,N-dimethylformamide (0.375 M, 0.4 ml, 0.15 mmol), a solution of 3-methoxycinnamic acid in N,N-dimethylformamide (0.375 M, 0.4 ml, 0.15 mmol) and 0.25 ml of a suspension of N-(3-dimethylaminopropyl)-N'-ethylcarbodiimide hydrochloride in dichloromethane (1.73 g in 8.3 ml) affords the title compound.

HPLC-MS: 16.54 min. m/z: 444 (M+1)

Example 140

3-(4-Chlorophenyl)-1-[4-(4-trifluoromethylphenyl)-4,5,6,7-tetrahydro-thieno[3,2-c]pyridin-5-yl]propenone

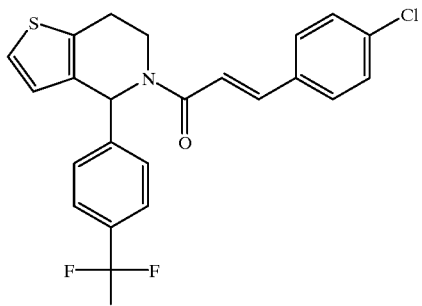

Similarly as described in example 22 using a solution of 4-(4-trifluoromethylphenyl)4,5,6,7-tetrahydro-thieno [3,2-c]pyridine in N,N-dimethylformamide (0.375 M, 0.4 ml, 0.15 mmol), a solution of 4-chlorocinnamic acid in N,N-dimethylformamide (0.375 M, 0.4 ml, 0.15 mmol) and 0.25 ml of a suspension of N-(3-dimethylaminopropyl)-N'-ethylcarbodiimide hydrochloride in dichloromethane (1.73 g in 8.3 ml) affords the title compound.

HPLC-MS: $R_t$=17.41 min. m/z: 448 (M+1)

Example 141

3-(4-Methoxyphenyl)-1-[4-(4-trifluoromethylphenyl)-4,5,6,7-tetrahydro-thieno[32-c]pyridin-5-yl]propan-1-one

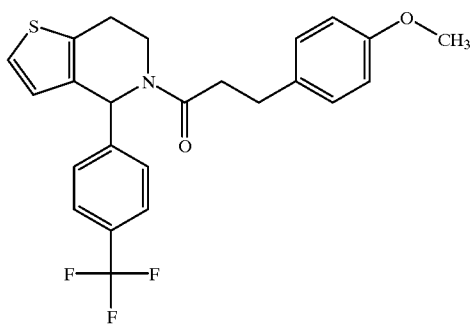

Similarly as described in example 22 using a solution of 4-(4-trifluoromethylphenyl)-4,5,6,7-tetrahydro-thieno [3,2-c]pyridine in N,N-dimethylformamide (0.375 M, 0.4 ml, 0.15 mmol), a solution of 4-methoxyhydrocinnamic acid in N,N-dimethylformamide (0.375 M, 0.4 ml, 0.15 mmol) and 0.25 ml of a suspension of N-(3-dimethylaminopropyl)-N'-ethylcarbodiimide hydrochloride in dichloromethane (1.73 g in 8.3 ml) affords the title compound.

HPLC-MS: $R_t$=16.41 min. m/z: 446 (M+1)

Example 142

3-(4-Chlorophenyl)-1-[4-(4-trifluoromethylphenyl)4,5,6,7-tetrahydro-thieno[3,2-c]pyridin-5-]propan-1-one

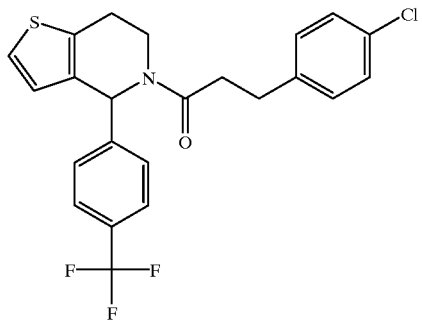

Similarly as described in example 22 using a solution of 4-(4-trifluoromethylphenyl)-4,5,6,7-tetrahydro-thieno [3,2-c]pyridine in N,N-dimethylformamide (0.375 M, 0.4 ml, 0.15 mmol), a solution of 4-chlorohydrocinnamic acid in N,N-dimethylformamide (0.375 M, 0.4 ml, 0.15 mmol) and 0.25 ml of a suspension of N-(3dimethylaminopropyl)-N'-ethylcarbodiimide hydrochloride in dichloromethane (1.73 g in 8.3 ml) affords the title compound.

HPLC-MS: $R_t$=17.38 min. m/z: 450 (M+1)

General:

The HPLC-MS analyses were performed on a PE Sciex API 100 LC/MS System using a WatersTM 3 mm×150 mm 3.5 µ C-18 Symmetry column and positive ionspray with a flow rate at 20 µL/minute. The column was eluted with a linear gradient of 5–90% A, 85-0% B and 10% C in 15 minutes at a flow rate of 1 ml/min (solvent A =acetonitrile, solvent B=water and solvent C=0.1% trifluoroacetic acid in water).

The given HPLC (method B) refers to the following system:

The used HPLC-system was comprised of a Merck Hitachi L-4000 UV Detector (detection at 254 nm), a Merck Hitachi L6200A Intelligent Pump, a Merck Hitachi AS-2000A Autosampler, and a 4 mm * 250 mm 5 µ Licrosorp RP-18 column. The compounds were eluted using a gradient of 20% to 80% acetonitrile/0.1% trifluoroacetic acid/water during 30 minutes at 1 ml/minute, followed by a gradient of 80% to 100% acetonitrile/0.1% trifluoroacetic acid/water during 5 minutes at 1 ml/minute then with 100% acetonitrile/0.1% trifluoroacetic acid during 1 minute at 1 ml/minute and 4 minutes at 2 ml/minute.

What is claimed is:

1. A pharmaceutical composition comprising a pharmaceutically acceptable carrier or diluent and a compound of formula I

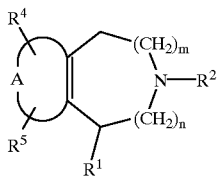

wherein

A together with the double bond of formula I is thiophene,
$R^1$ is optionally substituted $C_{1-6}$-alkyl or optionally substituted aryl, $R^2$ is optionally substituted $C_{1-6}$-alkyl, optionally substituted aralkyl, or —$COR^3$, wherein $R^3$ is optionally substituted $C_{1-6}$-alkyl, optionally substituted aralkyl, or optionally substituted aryl, $R^4$ and $R^5$ independently are hydrogen, halogen, perhalomethyl, optionally substituted $C_{1-6}$-alkyl, hydroxy, optionally substituted $C_{1-6}$-alkoxy, nitro, cyano, amino, optionally substituted mono- or optionally substituted di-$C_{1-6}$-alkylamino, acylamino, $C_{1-6}$-alkoxycarbonyl, carboxy or carbamoyl, n is 0, and m is 1, or a pharmaceutically acceptable salt thereof, or an optical isomer or mixture of optical isomers thereof, or a tautomeric form thereof.

2. The pharmaceutical composition of claim 1, wherein each one of $R^1$, $R^2$, and $R^3$ is substituted with one or more substituents.

3. The pharmaceutical composition of claim 1, wherein $R^1$ is optionally substituted phenyl.

4. The pharmaceutical composition of claim 1, wherein the substituents of $R^1$ are independently halogen, perhalomethyl, perhalomethoxy, or $C_{1-6}$-alkoxy.

5. The pharmaceutical composition of claim 4, wherein the substituents of $R^1$ are independently chloro, trifluoromethyl, methoxy, and trifluoromethoxy.

6. The pharmaceutical composition of claim 5, wherein $R^1$ is phenyl, 4-chlorophenyl, 4-trifluoromethylphenyl, or 4-trifluoromethoxyphenyl.

7. The pharmaceutical composition of claim 1, wherein $R^1$ is 2,3-dihydrobenzofuran or 4-methoxyphenyl.

8. The pharmaceutical composition of claim 1, wherein $R^2$ is —$COR^3$ or $(CH_2)_q$-aryl, and q is 0, 1, 2, 3, 4, 5, or 6.

9. The pharmaceutical composition of claim 8, wherein $R^2$ is —$COR^3$.

10. The pharmaceutical composition of claim 9, wherein $R^3$ is phenyl, 3-methoxyphenyl, 4-methoxyphenyl, 4-chlorophenyl, 4-trifluoromethylphenyl, 4-(2-dimethylaminoethoxy)phenyl, or 4-(2-morpholin-4-ylethoxy)phenyl.

11. The pharmaceutical composition of claim 9, wherein $R^3$ is 4-methylphenyl, 3,4-dimethoxyphenyl, 4-ethoxyphenyl, 4-fluorophenyl, 4-trifluoromethylphenyl, dimethylaminophenyl, 4-(2-carboxyethenyl)phenyl, 4-(2-dimethylaminoethoxy)phenyl, 4-(2-morpholin-4-ylethoxy) phenyl, 1 H-indol-5-yl, 3-chloro-4-methoxyphenyl, or 1 H-benzimidazol-5-yl.

12. The pharmaceutical composition of claim 1, wherein $R^4$ and $R^5$ independently are hydrogen, halogen, perhalomethyl, $C_{1-6}$-alkyl, hydroxy, $C_{1-6}$-alkoxy, nitro, cyano, amino, mono- or di-$C_{1-6}$-alkylamino, acylamino, $C_{1-6}$-alkoxycarbonyl, carboxy or carbamoyl.

13. The pharmaceutical composition of claim 12, wherein $R^4$ and $R^5$ independently are hydrogen, chloro, or methoxy.

14. The pharmaceutical composition of claim 1, wherein
$R^1$ is phenyl, phenyl substituted with one or more halogen, perhalomethyl, perhalomethoxy, $C_{1-6}$-alkoxy, or 2,3-dihydrobenzofuran; and $R^2$ is —$COR^3$ wherein $R^3$ is phenyl, 3-methoxyphenyl, 4-methoxyphenyl, 4-chlorophenyl, 4-trifluoromethylphenyl, 4-(2-dimethylaminoethoxy) phenyl, 4-(2-morpholin-4-ylethoxy)phenyl, 4-methylphenyl, 3,4-dimethoxyphenyl, 4-ethoxyphenyl, 4-fluorophenyl, 4-trifluoromethylphenyl, dimethylaminophenyl, 4-(2-carboxyethenyl)phenyl, 4-(2-dimethylaminoethoxy) phenyl, 4-(2-morpholin-4-ylethoxy)phenyl, 1 H-indol-5-yl, 3-chloro-4-methoxyphenyl, or 1 H-benzimidazol-5-yl.

15. The pharmaceutical composition of claim 14, wherein $R^4$ and $R^5$ independently are hydrogen, halogen, perhalomethyl, $C_{1-6}$-alkyl, hydroxy, $C_{1-6}$-alkoxy, nitro, cyano, amino, mono- or di-$C_{1-6}$-alkylamino, acylamino, $C_{1-6}$-alkoxycarbonyl, carboxy or carbamoyl.

16. The pharmaceutical composition of claim 1, wherein the compound is of formula Ia:

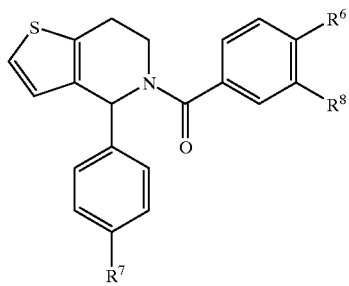

(Ia)

wherein $R^7$ is hydrogen, halogen, methoxy, perhalomethoxy, perhalomethyl, diloweralkylamino, or nitro, and $R^6$ and $R^8$ independently are hydrogen, hydroxy, halogen, methyl, tert-butyl, phenyl, dimethylamino, methoxy, ethoxy, 2-dimethylaminoethoxy, 2-carboxyethenyl, 2-morpholin-4-ylethoxy, perhalomethyl, perhalomethoxy, carboxy, cyano, methylthio, methylsulfonyl, acetamido, nitro, acetyl, acetoxy, or hydroxymethyl.

17. The pharmaceutical composition of claim 1, wherein the compound is of formula (Ia):

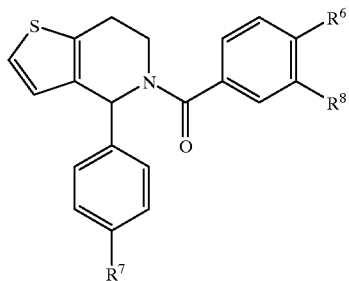

(Ia)

wherein $R^7$ is halogen, perhalomethyl, or perhalomethoxy, and $R^6$ and $R^8$ independently are hydrogen, methoxy, ethoxy, hydroxy, fluoro, chloro, bromo, iodo, methyl, trifluoromethyl, dimethylamino, 2-carboxyethenyl, 2-dimethylaminoethoxy, or 2-morpholin-4-ylethoxy.

18. The pharmaceutical composition of claim 17, wherein $R^7$ is chloro, methoxy, trifluoromethyl or trifluoromethoxy.

19. The pharmaceutical composition of claim 18, wherein $R^6$ and $R^8$ independently are hydrogen, methoxy, chloro, trifluoromethyl, 2-dimethylaminoethoxy, or 2-morpholin-4-ylethoxy.

20. The pharmaceutical composition of claim 17, wherein $R^6$ and $R^8$ independently are hydrogen, methoxy, chloro, trifluoromethyl, 2-dimethylaminoethoxy, or 2-morpholin-4-ylethoxy.

21. The pharmaceutical composition of claim 1, wherein the compound is of formula (Ib):

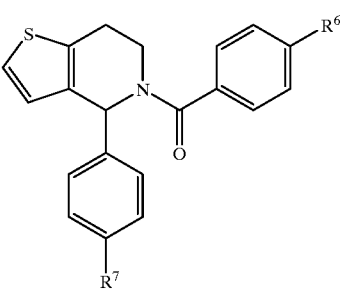

(Ib)

wherein $R^6$ is hydroxy, halogen, methyl, dimethylamino, methoxy, ethoxy, perhalomethyl, perhalomethoxy, cyano, methylthio, acetyl, acetoxy, or hydroxymethyl, and $R^7$ is hydrogen, halogen, methoxy, perhalomethoxy, perhalomethyl, diloweralkylamino, or nitro.

22. The pharmaceutical composition of claim 1, wherein the compound is of formula (Ic):

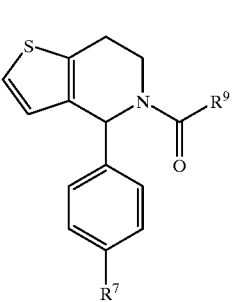

(Ic)

wherein $R^7$ is hydrogen, halogen, methoxy, perhalomethoxy, perhalomethyl, diloweralkylamino, or nitro, and $R^9$ is 4-pyridyl, 5-hydroxypyrazin-2-yl, 5-chloro-6-hydroxypyridin-3-yl, 2-chloropyridin-3-yl, benzofuran-2-yl, benzothiophen-2-yl, 7-methoxybenzofuran-2-yl, indolyl, benzimidazol, thienyl, or chlorothiophenyl.

23. The pharmaceutical composition of claim 22, wherein $R^9$ is benzothiophen-2-yl, 1 H-indol-5-yl, 1 H-benzimidazol-5-yl, or 5-chlorothiophen-2-yl.

24. The pharmaceutical composition of claim 1, wherein the compound is of formula (Ic):

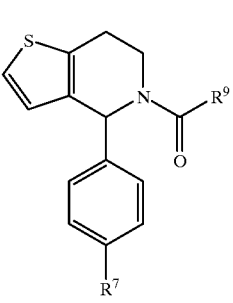

(Ic)

wherein $R^7$ is hydrogen, halogen, methoxy, perhalomethoxy, perhalomethyl, diloweralkylamino, or nitro, and $R^9$ is indolyl or benzimidazol.

25. The pharmaceutical composition of claim 1, wherein the compound is of formula (Id):

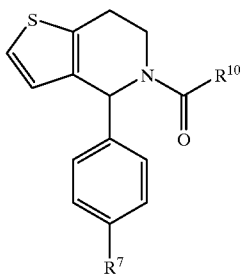

(Id)

wherein $R^7$ is hydrogen, halogen, methoxy, perhalomethoxy, perhalomethyl, diloweralkylamino, or nitro, and $R^{10}$ is 2-(4-methoxyphenyl)-ethenyl, 2-(3-methoxyphenyl)-ethenyl, 2-(4-chlorophenyl)-ethenyl, 2-(4-fluorophenyl)-ethenyl, 2-(4-trifluoromethylphenyl)-ethenyl, 2-(4-methoxyphenyl)-ethyl, 2-(4-chlorophenyl)-ethyl, 4-chlorobenzyl, 4-methoxybenzyl, 2-(2-furyl)-ethenyl, 2-(4,5-dimethyl-2-furyl)-ethenyl, 2-(5-methyl-2-furyl)-ethenyl, 2-(3-furyl)-ethenyl, 2-(2-thienyl)-ethenyl, or 2-(3-thienyl)-ethenyl.

26. The pharmaceutical composition of claim 25, wherein $R^{10}$ is 2-(4-methoxyphenyl)-ethenyl, 2-(2-furyl)-ethenyl, 2-(5-methyl-2-furyl)-ethenyl, 2-(3-furyl)-ethenyl, or 2-(3-thienyl)-ethenyl.

27. The pharmaceutical composition of claim 1, wherein the compound is of formula (Id):

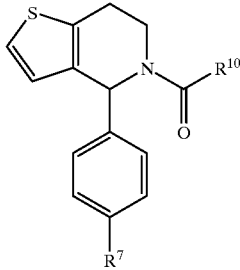

(Id)

wherein $R^7$ is hydrogen, halogen, methoxy, perhalomethoxy, perhalomethyl, diloweralkylamino, or nitro, and $R^{10}$ is 4-methoxyphenyl-2-ethenyl.

28. The pharmaceutical composition of claim 1, wherein the compound is of formula (Ie):

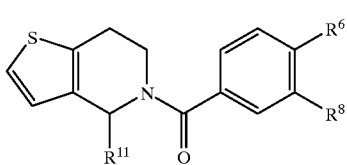

(Ie)

wherein $R^6$ and $R^8$ independently are hydrogen, hydroxy, halogen, methyl, tert-butyl, phenyl, dimethylamino, methoxy, ethoxy, 2-dimethylaminoethoxy, 2-carboxyethenyl, 2-morpholin-4-ylethoxy, perhalomethyl, perhalomethoxy, carboxy, cyano, methylthio, methylsulfonyl, acetamido, nitro, acetyl, acetoxy, or hydroxymethyl, and $R^{11}$ is pyridyl.

29. The pharmaceutical composition of claim 1, wherein the compound is of formula (If):

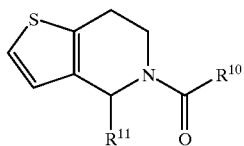

(If)

wherein $R^{10}$ is 2-(4-methoxyphenyl)-ethenyl, 2-(3-methoxyphenyl)-ethenyl, 2-(4-chlorophenyl)-ethenyl, 2-(4-fluorophenyl)-ethenyl, 2-(4-trifluoromethylphenyl)-ethenyl, 2-(4-methoxyphenyl)-ethyl, 2-(4-chlorophenyl)-ethyl, 4-chlorobenzyl, 4-methoxybenzyl, 2-(2-furyl)-ethenyl, 2-(4,5-dimethyl-2-furyl)-ethenyl, 2-(5-methyl-2-furyl)-ethenyl, 2-(3-furyl)-ethenyl, 2-(2-thienyl)-ethenyl, or 2-(3-thienyl)-ethenyl, and $R^{11}$ is pyridyl.

30. The pharmaceutical composition of claim 29, wherein $R^{11}$ is 4-pyridyl.

31. A pharmaceutical composition of claim 1, wherein the compound is of formula (Ig):

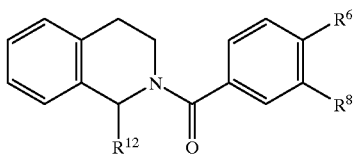

(Ig)

wherein $R^6$ and $R^8$ independently are hydrogen, hydroxy, halogen, methyl, tert-butyl, phenyl, dimethylamino, methoxy, ethoxy, 2-dimethylaminoethoxy, 2-carboxyethenyl, 2-morpholin-4-ylethoxy, perhalomethyl, perhalomethoxy, carboxy, cyano, methylthio, methylsufonyl, acetamido, nitro, acetyl, acetoxy, or hydroxymethyl, and $R^{12}$ is aryl or aralkyl.

32. A pharmaceutical composition of claim 31, wherein $R^{12}$ is 4-trifluoromethoxyphenyl or benzyl.

33. A pharmaceutical composition of claim 1, wherein the compound is of formula (Ih):

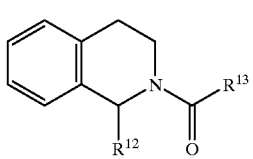

(Ih)

wherein $R^{12}$ is 4-trifluoromethoxyphenyl or benzyl, and

R¹³ is 2-(4-methoxyphenyl)-ethenyl, 2-(3-methoxyphenyl)-ethenyl, 2-(4-chlorophenyl)-ethenyl, 2-(4-fluorophenyl)-ethenyl, 2-(4-trifluoromethylphenyl)-ethenyl, 2-(4-methoxyphenyl)-ethyl, 2-(4-chlorophenyl)-ethyl, 4-chlorobenzyl, 4-methoxybenzyl, 2-(2-furyl)-ethenyl, 2-(4,5-dimethyl-2-furyl)-ethenyl, 2-(5-methyl-2-furyl)-ethenyl, 2-(3-furyl)-ethenyl, 2-(2-thienyl)-ethenyl, or 2-(3-thienyl)-ethenyl.

34. The pharmaceutical composition of claim 1, wherein the compound is:
[4-(4-Chlorophenyl)-4,5,6,7-tetrahydro-thieno[3,2-]pyridin-5-yl]-(4-methoxyphenyl)-methanone;
(4-Chlorophenyl)-[4-(4-chlorophenyl)-4,5,6,7-tetrahydro-thieno[3,2-c]pyridin-5-yl]-methanone;
(4-Chlorophenyl)-[4-(4-trifluoromethylphenyl)-4,5,6,7-tetrahydro-thineo[3,2-c]pyridin-5-yl]-methanone;
(2-Chlorophenyl)-[4-(4-methoxyphenyl)-4,5,6,7-tetrahydro-thieno[3,2-c]pyridin-5-yl]-methanone;
(4-Chlorophenyl)-[4-(methoxyphenyl)-4,5,6,7-tetrahydro-thieno[3,2-c]pyridin-5-yl]-methanone;
[4-(4-Methoxyphenyl)-4,5,6,7-tetrahydro-thieno[3,2-c]pyridin-5-yl]-(4-trifluoromethylphenyl)-methanone;
(2-Chloropyridin-3-yl)-[4-(4-methoxyphenyl)-4,5,6,7-tetrahydro-thieno[3,2-c]pyridin-5-yl]-methanone;
[4-(4-Chlorophenyl)-4,5,6,7-tetrahydro-thieno[3,2-c]pyridin-5-yl]-(2-thienyl)-methanone;
[4-(4-Methoxyphenyl)-4,5,6,7-tetrahydro-thieno[3,2-c]pyridin-5-yl]-(2-thienyl)-methanone;
(4-Chlorophenyl)-(4-propyl-4,5,6,7-tetrahydro-thieno[3,2-c]pyridin-5-yl)-methanone; or a pharmaceutically acceptable salt thereof, or an optical isomer or mixture of optical isomers thereof, or a tautomeric form thereof.

35. The pharmaceutical composition of claim 1, wherein the compound is:
[4-(4-Trifluoromethylphenyl)-4,5,6,7-tetrahydro-thieno[3,2-c]pyridin-5-yl]-(4-methoxyphenyl)-methanone;
[4-(4-Chlorophenyl)-4,5,6,7-tetrahydro-thieno[3,2-c]pyridin-5-yl]-phenyl-methanone;
(−)-[4-(4-Chlorophenyl)-4,5,6,7-tetrahydro-thieno[3,2-c]pyridin-5-yl]-(4-methoxyphenyl)-methanone;
(4-Chlorophenyl)-[4-(4-chlorophenyl)-4,5,6,7-tetrahydro-thieno[3,2-c]pyridin-5-yl]-methanone;
[4-(5-Trifluoromethylphenyl)-4,5,6,7-tetrahydro-thieno[3,2-c]pyridin-5yl]-(4-methoxyphenyl)-methanone;
[4-(4-Trifluoromethoxyphenyl)-4,5,6,7-tetrahydro-thieno[3,2-c]pyridin-5-yl]-(4-methoxyphenyl)-methanone;
[4-(4-Trifluoromethoxyphenyl)-4,5,6,7-tetrahydro-thieno[3,2-c]pyridin-5-yl]-(4-methoxyphenyl)-methanone;
(4-Methoxyphenyl)-[4-(4-methoxyphenyl)-4,5,6,7-tetrahydro-thieno[3,2-c]pyridin-5-yl]methanone;
(5-Chlorothiophen-2-yl)-[4-(4-dimethylaminophenyl)4,5,6,7-tetrahydro-thieno[3,2-c]pyridin-5-yl)-methanone;
(4-Chlorophenyl)-[4-(4-dimethylaminophenyl)-4,5,6,7-tetrahydro-thieno[3,2-c]pyridin-5-yl)-methanone;
(4-Methoxyphenyl)-[4-phenyl-4,5,6,7-tetrahydro-thieno[3,2-c]pyridin-5-yl)-methanone;
[4-(4-Dimethylaminophenyl)-4,5,6,7-tetrahydro-thieno[3,2-c]pyridin-5-yl]-(4-methoxyphenyl)-methanone;
(5-Chlorothiophen-2-yl)-(4-phenyl-4,5,6,7-tetrahydro-thieno[3,2-c]pyridin-5-yl)-methanone; or a pharmaceutically acceptable salt thereof, or an optical isomer or mixture of optical isomers thereof, or a tautomeric form thereof.

36. The pharmaceutical composition of claim 1, wherein the compound is:
(+)-[4-(4-Chlorophenyl)-4,5,6,7-tetrahydro-thieno[3,2-c]pyridin-5-yl]-(4-methoxyphenyl)-methanone;
(−)-[4-(4-Chlorophenyl)-4,5,6,7-tetrahydro-thieno[3,2-c]pyridin-5-yl]-(4-methoxyphenyl)-methanone;
(+)-[4-(4-Methoxyphenyl)-4,5,6,7-tetrahydro-thieno[3,2-c]pyridin-5-yl]-(4-trifluoromethylphenyl)-methanone;
(−)-[4-(4-Methoxyphenyl)-4,5,6,7-tetrahydro-thieno[3,2-c]pyridin-5-yl]-(4-trifluoromethylphenyl)-methanone;
[4-(4-Trifluoromethylphenyl)-4,5,6,7-tetrahydro-thieno[3,2-c]pyridin-5-yl]-(4-methoxyphenyl)-methanone;
(+)-[4-(4-Trifluoromethylphenyl)-4,5,6,7-tetrahydro-thieno[3,2-c]pyridin-5-yl]-(4-methoxyphenyl)-methanone;
(−)-[4-(4-Trifluoromethylphenyl)-4,5,6,7-tetrahydro-thieno[3,2-c]pyridin-5-yl]-(4-methoxyphenyl)-methanone;
[4-(4-Trifluoromethylphenyl)-4,5,6,7-tetrahydro-thieno[3,2-c]pyridin-5-yl]-(3-methoxyphenyl)-methanone;
(+)-[4-(4-Trifluoromethylphenyl)-4,5,6,7-tetrahydro-thieno[3,2-c]pyridin-5-yl]-(3-methoxyphenyl)-methanone;
(−)-[4-(4-Trifluoromethylphenyl)-4,5,6,7-tetrahydro-thieno[3,2-c]pyridin-5-yl]-(3-methoxyphenyl)-methanone;
[4-(4-Chlorophenyl)-4,5,6,7-tetrahydro-thieno[3,2-c]pyridin-5-yl]-phenyl-methanone;
(+)-[4-(4-Chlorophenyl)-4,5,6,7-tetrahydro-thieno[3,2-c]pyridin-5-yl]-phenyl-methanone;
(−)-[4-(4-Chlorophenyl)-4,5,6,7-tetrahydro-thieno[3,2-c]pyridin-5-yl]-phenyl-methanone;
(4-(2-Dimethylaminoethoxy)phenyl)-[4-(4-trifluoromethylphenyl)-4,5,6,7-tetrahydro-thieno[3,2-c]pyridin-5-yl]-methanone;
(+)-(4-(2-Dimethylaminoethoxy)phenyl)-[4-(4-trifluoromethylphenyl)-4,5,6,7-tetrahydro-thieno[3,2-c]pyridin-5-yl]-methanone;
(−)-(4-(2-Dimethylaminoethoxy)phenyl)-[4-(4-trifluoromethylphenyl)-4,5,6,7-tetrahydro-thieno[3,2-c]pyridin-5-yl]-methanone;
[4-(4-Chlorophenyl)-4,5,6,7-tetrahydro-thieno[3,2-c]pyridin-5-yl]-(4-(2-[2-morpholin-4-yl)ethoxy)phenyl]-methanone;
(+)-[4-(4-Chlorophenyl)-4,5,6,7-tetrahydro-thieno[3,2-c]pyridin-5-yl]-(4-(2-[2-morpholin-4-yl)ethoxy) phenyl]-methanone;
(−)-[4-(4-Chlorophenyl)-4,5,6,7-tetrahydro-thieno[3,2-c]pyridin-5-yl]-(4-(2-[2-morpholin-4-yl)ethoxy) phenyl]-methanone;
[4-(4-Trifluoromethylphenyl)-4,5,6,7-tetrahydro-thieno[3,2-c]pyridin-5-yl]-(4-dimethylaminophenyl)-methanone;
3-{4-[4-(4-Chlorophenyl)-4,5,6,7-tetrahydro-thieno[3,2-c]pyridine-5-carbonyl ]phenyl}acrylic acid;
(4-Chlorophenyl)-[4-(4-chlorophenyl)-4,5,6,7-tetrahydro-thieno[3,2-c]pyridin-5-yl]-methanone;
[4-(4-Trifluoromethylphenyl)-4,5,6,7-tetrahydro-thieno[3,2-c]pyridin-5-yl]-(4-methoxyphenyl)-methanone;
[4-(4-Trifluoromethylphenyl)-4,5,6,7-tetrahydro-thieno[3,2-c]pyridin-5-yl]-(4-methoxyphenyl)-methanone;
[4-(2-Dimethylaminoethoxy)-phenyl]-[4-(4-trifluoromethylphenyl)-4,5,6,7-tetrahydro-thieno[3,2-c]pyridin-5-yl]-methanone;

[4-(2-Dimethylaminoethoxy)-phenyl]-[4-(4-trifluoromethylphenyl)-4,5,6,7-tetrahydro-thieno [3,2-c]pyridin-5-yl]-methanone;
[4-(4-Chlorophenyl)-4,5,6,7-tetrahydro-thieno[3,2-c]pyridin-5-yl]-[4-(2-morpholin-4-ylethoxy) phenyl]-methanone;
[4-(4-Chlorophenyl)-4,5,6,7-tetrahydro-thieno[3,2-c]pyridin-5-yl]-[4-(2-morpholin-4-ylethoxy) phenyl]-methanone;
[4-(4-Trifluoromethoxyphenyl)-4,5,6,7-tetrahydro-thieno[3,2-c]pyridin-5-yl]-(4-methoxyphenyl)-methanone;
[4-(4-Trifluoromethoxyphenyl)4,5,6,7-tetrahydro-thieno[3,2-c]pyridin-5-yl]-(4-methoxyphenyl)-methanone;
[4-(4-Trifluoromethoxyphenyl)-4,5,6,7-tetrahydro-thieno[3,2-c]pyridin-5-yl]-(4-methoxyphenyl)-methanone;
[4-(4-Chlorophenyl)-4,5,6,7-tetrahydro-thieno[3,2-c]pyridin-5-yl]-( 1 H-indol-5-yl)-methanone;
(1 H-Indol-5-yl)-[4-(4-trifluoromethoxyphenyl)-4,5,6,7-tetrahydro-thieno[3,2-c]pyridin-5-yl]-methanone;
[4-(4-Chlorophenyl)-4,5,6,7-tetrahydro-thieno[3,2-c]pyridin-5-yl]-(4-fluorophenyl)-methanone;
[4-(4-Trifluoromethoxyphenyl)-4,5,6,7-tetrahydro-thieno[3,2-c]pyridin-5-yl]-(4-fluorophenyl)-methanone;
4-(4-Chlorophenyl)-4,5,6,7-tetrahydro-thieno[3,2-c]pyridin-5-yl]-[4-(2-dimethylaminoethoxy) phenyl]-methanone;
[4-(2-Dimethylaminoethoxy)phenyl]-[4-(4-trifluoromethoxyphenyl)-4,5,6,7-tetrahydro-thieno[3,2-c]pyridin-5-yl]-methanone;
[4-(3,4-Dimethoxyphenyl)-4,5,6,7-tetrahydro-thieno[2,3-c]pyridin-6-yl]-[4-(2-dimethylaminoethoxy)-phenyl]-methanone;
(3,4-Dimethoxyphenyl)-[4-(4-trifluoromethoxyphenyl)-4,5,6,7-tetrahydro-thieno [3,2-c]pyridin-5-yl] methanone;
(3-Chloro-4-methoxyphenyl)-[4-(4-trifluoromethoxyphenyl)-4,5,6,7-tetrahydro-thieno[3,2-c]pyridin-5-yl]methanone;
(4-Ethoxyphenyl)-[4-(4-trifluoromethoxyphenyl)-4,5,6,7-tetrahydro-thieno[3,2-c]pyridin-5-yl]methanone;
(4-Methylpheny2)-[4-(4-trifluoromethoxyphenyl)-4,5,6,7-tetrahydro-thieno[3,2-c]pyridin-5-yl]methanone;
3-(4-Methoxyphenyl)-1-[4-(4-trifluoromethoxyphenyl)-4,5,6,7-tetrahydro-thieno [3,2-c]pyridin-5-yl] propenone;
(1 H-Benzimidazol-5-yl)-[4-(4-trifluoromethoxyphenyl)-4,5,6,7-tetrahydro-thieno[3,2-c]pyridin-5-yl] methanone; or a pharmaceutically acceptable salt thereof, or an optical isomer or mixture of optical isomers thereof, or a tautomeric form thereof.

37. The pharmaceutical composition of claim 1, wherein the compound is:
(+)-[4-(4-Methoxyphenyl)-4,5,6,7-tetrahydro-thieno[3,2-c]pyridin-5-yl]-(4-trifluoromethylphenyl)-methanone;
[4-(4-Trifluoromethylphenyl)-4,5,6,7-tetrahydro-thieno [3,2-c]pyridin-5-yl]-(4-dimethylaminophenyl)-methanone;
[4-(4-Chlorophenyl)-4,5,6,7-tetrahydro-thieno[3,2-c]pyridin-5-yl]-(1 H-indol-5-yl)-methanone;
(1 H-Indol-5-yl)-[4-(4-trifluoromethoxyphenyl)-4,5,6,7-tetrahydro-thieno[3,2-c]pyridin-5-yl]-methanone;
[4-(4-Chlorophenyl)-4,5,6,7-tetrahydro-thieno[3,2-c]pyridin-5-yl]-(4-fluorophenyl)-methanone;
[4-(4-Trifluoromethoxyphenyl)-4,5,6,7-tetrahydro-thieno[3,2-c]pyridin-5-yl]-(4-fluorophenyl)-methanone;
(3,4-Dimethoxyphenyl)-[4-(4-trifluoromethoxyphenyl)-4,5,6,7-tetrahydro-thieno [3,2-c]pyridin-5-yl] methanone;
(3-Chloro-4-methoxyphenyl)-[4-(4-trifluoromethoxyphenyl)-4,5,6,7-tetrahydro-thieno[3,2-c]pyridin-5-yl]methanone;
(4-Ethoxyphenyl)-[4-(4-trifluoromethoxyphenyl)-4,5,6,7-tetrahydro-thieno[3,2-c]pyridin-5-yl ]methanone;
(4-Methylphenyl)-[4-(4-trifluoromethoxyphenyl)-4,5,6,7-tetrahydro-thieno[3,2-c]pyridin-5-yl ]methanone;
3-(4-Methoxyphenyl)-1-[4-(4-trifluoromethoxyphenyl)-4,5,6,7-tetrahydro-thieno [3,2-c]pyridin-5-yl] propenone;
(1 H-Benzimidazol-5-yl)-[4-(4-trifluoromethoxyphenyl)-4,5,6,7-tetrahydro-thieno[3,2-c ]pyridin-5-yl] methanone;
(4-Methoxyphenyl)-[4-(4-trifluoromethoxyphenyl)-4,5,6,7-tetrahydro-thieno[3,2-c]pyridin-5-yl]- methanone;
[4-(4-Trifluoromethoxyphenyl)-4,5,6,7-tetrahydro-thieno[3,2-c]pyridin-5-yl]-(4-methoxyphenyl)-methanone;
[4-(4-Trifluoromethylphenyl)-4,5,6,7-tetrahydro-thieno[3,2-c]pyridin-5-yl]-(4-methylsulfanylphenyl)-methanone;
4-[4-(4-Trifluoromethylphenyl)-4,5,6,7-tetrahydro-thieno[3,2-c]pyridine-5-carbonyl]benzoic acid methyl ester;
(4-Hydroxymethylphenyl)-[4-(4-trifluoromethylphenyl)-4,5,6,7-tetrahydro-thieno[3,2-c ]pyridin-5-yl] methanone;
(4-Acetoxyphenyl)-[4-(4-trifluoromethylphenyl)-4,5,6,7-tetrahydro-thieno[3,2-c]pyridin-5-yl ]methanone;
(4-Cyanophenyl)-[4-(4-trifluoromethylphenyl)-4,5,6,7-tetrahydro-thieno[3,2-c]pyridin-5-yl ]methanone;
1-{4-[4-(4-Trifluoromethylphenyl)-4,5,6,7-tetrahydro-thieno[3,2-c]pyridine-5-carbonyl ]phenyl }ethanone;
3-(5-Methylfuran-2-yl)-1-[4-(4-trifluoromethylphenyl)-4,5,6,7-tetrahydro-thieno[3,2-c ]pyridin-5-yl] propenone;
3-Furan-3-yl-1-[4-(4-trifluoromethylphenyl)-4,5,6,7-tetrahydro-thieno[3,2-c]pyridin-5-yl ]propenone;
3-Thiophen-3-yl-1-[4-(4-trifluoromethylphenyl)-4,5,6,7-tetrahydro-thieno[3,2-c]pyridin-5-yl ]propenone;
(4-Methylsulfanylphenyl)-[4-(4-trifluoromethoxyphenyl)-4,5,6,7-tetrahydro-thieno[3,2-c ]pyridin-5-yl]methanone;
(4-Dimethylaminophenyl)-[4-(4-trifluoromethoxypheny2)-4,5,6,7-tetrahydro-thieno[3,2-c ]pyridin-5-yl]methanone;
(4-Hydroxymethylphenyl)-[4-(4-trifluoromethoxyphenyl)-4,5,6,7-tetrahydro-thieno(3,2-c ]pyridin-5-yl]methanone;
3-Furan-3-yl-1-[4-(4-trifluoromethoxyphenyl)-4,5,6,7-tetrahydro-thieno[3,2-c]pyridin-5-yl ]propenone;
[4-(4-Chlorophenyl)-4,5,6,7-tetrahydro-thieno[3,2-c]pyridin-5-yl]-(4-hydroxyphenyl) methanone;
(4-Hydroxymethylphenyl)-(4-phenyl-4,5,6,7-tetrahydro-thieno[3,2-c]pyridin-5-yl) methanone;
[4-(4-Dimethylaminophenyl)-4,5,6,7-tetrahydro-thieno[3,2-c]pyridin-5-yl)-(4-hydroxymethylphenyl)-methanone;
(4-Chlorophenyl)-(4-phenyl-4,5,6,7-tetrahydro-thieno[3,2-c]pyridin-5-yl)methanone;
[4-(4-Dimethylaminophenyl)-4,5,6,7-tetrahydro-thieno[3,2-c]pyridin-5-yl]-(4-methoxyphenyl)-methanone;
(4-Dimethylaminophenyl)-(4-phenyl-4,5,6,7-tetrahydro-thieno[3,2-c]pyridin-5-yl)-methanone;
(4-Dimethylaminophenyl)-[4-(4-dimethylaminophenyl)-4,5,6,7-tetrahydro-thieno[3,2-c ]pyridin-5-yl]-methanone;

3-Furan-3-yl-1-(4-phenyl-4,5,6,7-tetrahydro-thieno[3,2-c]pyridin-5-yl)-propenone;

[4-(4-Chlorophenyl)-4,5,6,7-tetrahydro-thieno[3,2-c]pyridin-5-yl]-(4-hydroxyphenyl)-methanone;

(1-Benzoimidazol-5-yl)-[4-(4-trifluoromethoxyphenyl)-4,5,6,7-tetrahydro-thieno[3,2-c]pyridin-5-yl]methanone, more polar enantiomer;

3-(4-Fluorophenyl)-1-[4-(4-trifluoromethylphenyl)-4,5,6,7-tetrahydro-thieno[3,2-c]pyridin-5-yl]propenone; or a pharmaceutically acceptable salt thereof, or an optical isomer or mixture of optical isomers thereof, or a tautomeric form thereof.

38. The pharmaceutical composition of claim 1 in the form of an oral dosage unit or a parenteral dosage unit.

39. The pharmaceutical composition of claim 38 wherein the compound is present in an amount in a range from about 0.05 to 1000 mg.

40. A method of treating or preventing a disease of the endocrine system, comprising administering to a subject in need thereof an effective amount of a compound of formula I

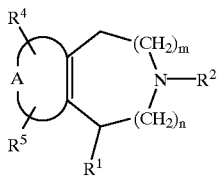

wherein

A together with the double bond of formula I is thiophene, $R^1$ is optionally substituted $C_{1-6}$-alkyl or optionally substituted aryl, $R^2$ is optionally substituted $C_{1-6}$-alkyl, optionally substituted aralkyl, or —$COR^3$, wherein $R^3$ is optionally substituted $C_{1-6}$-alkyl, optionally substituted aralkyl, or optionally substituted aryl, $R^4$ and $R^5$ independently are hydrogen, halogen, perhalomethyl, optionally substituted $C_{1-6}$-alkyl, hydroxy, optionally substituted $C_{1-6}$-alkoxy, nitro, cyano, amino, optionally substituted mono- or optionally substituted di-$C_{1-6}$-alkylamino, acylamino, $C_{1-6}$-alkoxycarbonyl, carboxy or carbamoyl, n is 0, and m is 1, or a pharmaceutically acceptable salt thereof, or an optical isomer or mixture of optical isomers thereof, or a tautomeric form thereof.

41. The method of claim 40, wherein the disease is diabetes.

42. The method of claim 41, wherein the disease is NIDDM.

43. The method of claim 40, wherein the disease is hyperglycemia or hypoglycemia.

44. The method of claim 40, wherein $R^1$ is phenyl, phenyl substituted with one or more halogen, perhalomethyl, perhalomethoxy, $C_{1-6}$-alkoxy, or 2,3-dihydrobenzofuran; and $R^2$ is —$COR^3$ wherein $R^3$ is phenyl, 3-methoxyphenyl, 4-methoxyphenyl, 4-chlorophenyl, 4-trifluoromethylphenyl, 4-(2-dimethylaminoethoxy)phenyl, 4-(2-morpholin-4-ylethoxy)phenyl, 4-methylphenyl, 3,4-dimethoxyphenyl, 4-ethoxyphenyl, 4-fluorophenyl, 4-trifluoromethylphenyl, dimethylaminophenyl, 4-(2-carboxyethenyl)phenyl, 4-(2-dimethylaminoethoxy)phenyl, 4-(2-morpholin-4-ylethoxy)phenyl, 1 H-indol-5-yl, 3-chloro-4-methoxyphenyl, or 1 H-benzimidazol-5-yl.

45. A pharmaceutical composition comprising a pharmaceutically acceptable carrier or diluent and a compound of formula I

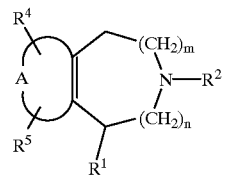

wherein

A together with the double bond of formula I is benzene, $R^1$ is optionally substituted $C_{1-6}$-alkyl or optionally substituted aryl, $R^2$ is optionally substituted $C_{1-6}$-alkyl, optionally substituted aralkyl, or —$COR^3$, wherein $R^3$ is optionally substituted $C_{1-6}$-alkyl, optionally substituted aralkyl, or optionally substituted aryl, $R^4$ and $R^5$ independently are hydrogen, halogen, perhalomethyl, optionally substituted $C_{-6}$-alkyl, hydroxy, optionally substituted $C_{1-6}$-alkoxy, nitro, cyano, amino, optionally substituted mono- or optionally substituted di-$C_{1-6}$-alkylamino, acylamino, $C_{1-6}$-alkoxycarbonyl, carboxy or carbamoyl, is 0, and m is 1, or a pharmaceutically acceptable salt thereof, or an optical isomer or mixture of optical isomers thereof, or a tautomeric form thereof, wherein the compound is selected from the group consisting of:

[7-Chloro-1-(2,3-dihydrobenzofuran-7-yl)-8-methoxy-1,2,4,5-tetrahydrobenzo[d]azepin-3-yl]-[4-(2-dimethylaminoethoxy)-phenyl]-methanone;

(1-Benzyl-1,2,3,4-tetrahydro-isoquinolin-2-yl)-(4-methoxyphenyl)methanone;

(1-Benzyl-1,2,3,4-tetrahydro-isoquinolin-2-yl)-(4-chlorophenyl)methanone;

(1 H-Benzoimidazol-5-yl)-(1-benzyl-1,2,3,4-tetrahydro-isoquinolin-2-yl)methanone;

1-(1-Benzyl-1,2,3,4-tetrahydro-isoquinolin-2-yl)-3-furan-3-ylpropenone;

1-(1-Benzyl-1,2,3,4-tetrahydro-isoquinolin-2-yl)-3-(4-methoxyphenyl)propenone;

1-(1-Benzyl-1,2,3,4-tetrahydro-isoquinolin-2-yl)-3-(4-methoxyphenyl)propan-1-one;

1-(1-Benzyl-1,2,3,4-tetrahydro-isoquinolin-2-yl)-2-(4-methoxyphenyl)ethanone;

(5-Chlorothiophen-2-yl)-[1-(4-trifluoromethoxyphenyl)-1,2,3,4-tetrahydroisoquinolin-2-yl]-methanone;

(4-Chlorophenyl)-[1-(4-trifluoromethoxyphenyl)-1,2,3,4-tetrahydroisoquinolin-2-yl]-methanone;

(4-Methoxyphenyl)-[1-(4-trifluoromethoxyphenyl)-1,2,3,4-tetrahydroisoquinolin-2-yl]-methanone;

3-(4-Methoxyphenyl)-1-[1-(4-trifluoromethoxyphenyl)-1,2,3,4-tetrahydroisoquinolin-2-yl]propenone; and 3-Furan-3-yl-1-[1-(4-trifluoromethoxyphenyl)-1,2,3,4-tetrahydroisoquinolin-2-yl]propenone.

* * * * *